US007026156B1

(12) United States Patent
Clark et al.

(10) Patent No.: US 7,026,156 B1
(45) Date of Patent: Apr. 11, 2006

(54) DIAGNOSTIC AND PROTECTIVE ANTIGEN GENE SEQUENCES OF ICHTHYOPHTHIRIUS

(75) Inventors: Theodore G. Clark, Ithaca, NY (US); Harry W. Dickerson, Jr., Athens, GA (US); Tian-Long Lin, Fujian (CN)

(73) Assignees: The University of Georgia Research Foundation, Inc., Athens, GA (US); Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/497,967

(22) Filed: Feb. 4, 2000

Related U.S. Application Data

(60) Provisional application No. 60/131,121, filed on Apr. 27, 1999, provisional application No. 60/118,634, filed on Feb. 4, 1999, provisional application No. 60/124,905, filed on Mar. 17, 1999, provisional application No. 60/122,372, filed on Mar. 2, 1999.

(51) Int. Cl.
*C12N 1/20* (2006.01)
*C12N 15/00* (2006.01)
*C12N 5/00* (2006.01)
*A61K 31/70* (2006.01)
*C07H 21/02* (2006.01)

(52) U.S. Cl. ............................ 435/252.3; 435/320.1; 435/325; 514/44; 536/23.1; 536/23.5

(58) Field of Classification Search ............... 536/23.1, 536/23.5; 435/6, 7.22, 252.3, 320.1, 325; 530/387.9; 514/44
See application file for complete search history.

(56) References Cited

U.S. PATENT DOCUMENTS

| 4,309,416 | A | | 1/1982 | Gratzek et al. |
| 5,302,527 | A | * | 4/1994 | Birkett et al. ............. 435/254.5 |
| 5,661,032 | A | | 8/1997 | Miller et al. |
| 5,695,965 | A | | 12/1997 | Stuart et al. |
| 5,780,448 | A | | 7/1998 | Davis |
| 6,087,124 | A | | 7/2000 | Steinbrück et al. |

FOREIGN PATENT DOCUMENTS

| EP | 0773 295 A2 | 5/1997 |
| WO | WO 81/00812 | 4/1981 |
| WO | WO 90/14428 | 11/1990 |
| WO | WO 98/01572 | 1/1998 |

OTHER PUBLICATIONS

Clark et al (PNAS 1992 vol. 89 pp 6363-6367).*
Ellis et al., "Vaccines," Chapter 29, pp. 568-575, published by W.B. Saunders Company (Philadelphia) 1998.
Hai et al., "Germ-line knockout heterokaryons of an essential α-tubulin gene enable high-frequency gene replacement and a test of gene transfer from somatic to germ-line nuclei in *Tetrahymena thermophila*," *Proc. Natl. Acad. Sci. USA*, 94:1310-1315 (1997).
Nossal, "Vaccines,"*Fundamental Immunology, Fourth Edition*, Ed. W. Paul, Chapter 42, pp. 1387-1425 (Lippincott-Raven, Philadelphia, 1999).
Paoletti, "Applications of pox virus vectors to vaccination: An update," *Proc. Natl. Acad. Sci. USA*, 93:11349-11353 (1996).
Sanford et al., "An Improved, Helium-Driven Biolistic Device," *Technique*, 3(1):3-16 (1991).
Alexander, "A New Immobilization Test for *Tetrahymena pyriformis*," *Trans. Amer. Microsc. Soc.*, 86(4):421-427 (1967).
Al-Qahtani et al., "A 5' untranslated region which directs accurate and robust translation by prokaryotic and mammalian ribosomes," *Nuc. Acids Res.*, 24(6):1173-1174 (1996).
Areerat, *The Immune Response of Channel Catfish, Ictalurus punctatus (Rafinesque), to Ichthyophthirius multifiliis*, Master's thesis, Auburn University, 47 pages (1974).
Berg et al., "The Galvanization of Biology: A Growing Appreciation for the Roles of Zinc," *Science*, 271:1081-1085 (1996).
Blomberg et al., "Regulatory Sequences for the Amplification and Replication of the Ribosomal DNA Minichromosome in *Tetrahymena thermophila*," *Mol. Cell. Biol.*, 17 (12):7237-7247 (1997).
Bolduc et al., "β-Tubulin mutants of the unicellular green alga *Chlamydomonas reinhardtii*," *Proc. Natl. Acad. Sci. USA.* 85(1):131-135 (1988).
Boothroyd et al., eds., *Molecular Approaches to Parasitology*, John Wiley & Sons, New York, Title page, publication page and table of contents only, 4 pages (1995).
Brosius et al., "Gene Organization and Primary Structure of a Ribosomal RNA Operon from *Escherichia coli*," *J. Mol. Biol.*, 148(2):107-127 (1981).
Brunk et al., "Analysis of Nuclei from Exponentially Growing and Conjugated *Tetrahymena thermophila* Using the Flow Microfluorimeter," *Exp. Cell Res.*, 162:390-400 (1986).
Brunk et al., "Characterization of the promoter region of *Tetrahymena* genes," *Nuc. Acids. Res.*, 18(2):323-329 (1990).

(Continued)

*Primary Examiner*—Mark Navarro
(74) *Attorney, Agent, or Firm*—Mueting Raasch & Gebhardt, P.A.

(57) ABSTRACT

A novel i-antigen protein from *Ichthyophthirius multifiliis* is effective to induce a protective immune response in fish. The invention includes antigenic and membrane-targeting sequences of i-antigen proteins, nucleic acid molecules that encode antigenic or membrane-targeting portions of i-antigen proteins, DNA and protein subunit vaccines, methods of inducing an immune response in fish and methods for detection and characterization of *I. multifiliis*.

15 Claims, 27 Drawing Sheets

OTHER PUBLICATIONS

Brunk, "Ciliates display promise for foreign gene expression," *Nature Biotechnology, 17*:424-425 (May, 1999).

Burkart et al., "Immunization of channel catfish, *Ictalurus punctatus* Rafinesque, against *Ichthyophthirius multifiliis* (Fouquet) killed versus live vaccines," *J. Fish Dis., 13*:401-410 (1990).

Caras et al., "Cloning of decay-accelerating factor suggest novel use of splicing to generate two proteins," *Nature, 325*:545-549 (1987).

Cara et al., "Signal Peptide for Protein Secretion Directing Glycophospholipid Membrane Anchor Attachment," *Science, 243*(4895):1196-1198 (1989).

Caron et al., "Molecular Basis of Surface Antigen Variation in Patramecia," *Ann. Rev. Microbiol., 43*:23-42 (1989).

Caruthers, "New Methods for Chemically Synthesizing Deoxyoligonucleotides,," *Methods of DNA and RNA Sequencing*, Weissman, ed., Praeger Publishers, New York, Title Page, publication page and pp. 1-22 (1983).

Cassidy-Hanley et al., "Germline and Somatic Transformation of Mating *Tetrahymena thermophila* by Particle Bombardment," *Genetics, 146*:135-147 (1997).

Catterall et al., "Nucleotide sequence homology at 12 intron-exon junctions in the chick ovalbumin gene," *Nature, 275* (5680):510-513 (1978).

Chen et al., "A *Giardia duodenalis* gene encoding a protein with multiple repeats of a toxin homologue," *Parasitol., 111*(4):423-431 (1995).

Clark et al., "In vitro response of *Ichthyophthirius multifiliis* to sera from immune channel catfish," *J. Fish Biol., 31* (Supplement A):203-208 (1987).

Clark et al., "Immune Response of Channel Catfish to Ciliary Antigens of *Ichthyophthirius multifiliis*" Devel. Comp. Immunol., 12(3):581-594 (1988).

Clark et al., "Differential Expression of Membrane Antigen Genes in *I. Multifiliis*, a Protozoan Pathogen of Fish," Abstract and Poster, Annual Meeting on Molecular Parasitology, Woods Hole, MA, Sep. 9-12, 7 pages (1990).

Clark et al., "Development expression of surface antigen genes in the parasitic ciliate *Ichthyophthirius multifiliis*," *Proc. Natl. Acad. Sci. USA, 89*:6363-6367 (1992).

Clark et al., "Surface Immobilization Antigens of *Ichthyophthirius multifiliis*: Their Role in Protective Immunity," *Ann. Rev. Fish Dis., 5*:113-131 (1995).

Clark et al., "Surface antigen cross-linking triggers forced exit of a protozoan parasite from its host," *Proc. Natl. Acad. Sci. USA, 93*(13):6825-6829 (1996).

Clark et al., "Antibody-mediated Effects on Parasite Behavior: Evidence of a Novel Mechanism of Immunity against a Parasitic Protist," *Parasitol. Today, 13*(12):477-480 (1997).

Clark, "Molecular Approaches to the Control of Ichthyophthirius Infection," Abstract, Grant for Oct. 25, 1997 through Jun. 30, 2002, Cooperating Schools of Veterinary Medicine GEOV, proj. No. NYCV-433-391 (Available on-line on or before Jul. 19, 1998).

Clark et al., "The gene for an abundant parasite coat protein predicts tandemly repetitive metal binding domains," *Genes, 229*(1-2):91-100 (Mar. 18, 1999).

Cohen et al., "Expression of a Ciliate Gene in *Escherichia coli* Using a Suppressor tRNA to Read the UAA and UAG Glutamine Codons," *J. Mol. Biol., 216*:189-194 (1990).

Cross et al., "Ichthyophthiriasis in carp, *Cyprinus carpio* L.: fate of parasites in immunized fish," *J. Fish Dis., 15*:497-505 (1992).

Cupples et al., "Isolation and characterization of the actin gene from *Tetrahymena thermophila*," *Proc. Natl. Acad. USA, 83*(14):5160-5164 (1986).

Deak et al., "Sequence, codon usage and cysteine periodicity of the SerH1 gene and in the encoded surface protein of *Tetrahymena thermophila*," *Gene, 164*:163-166 (1995).

Dempsey et al., "C3d of Complement as a Molecular Adjuvant: Bridging Innate and Acquired Immunity," *Science, 271*:348-350 (1996).

Deng et al., "Site-Directed Mutagenesis of Virtually Any Plasmid by Eliminating a Unique Site," *Anal. Biochem.,* 200:81-88 (1992).

Dickerson et al., "*Ichthyophthirius multifiliis* Has Membrane-Associated Immobilization Antigens," *J. Protozool., 36*(2):159-164 (1989).

Dickerson et al., "Molecular Approaches to the Prevention of Ichthyophthirius Infection," Abstract, Grant for Sep. 1, 1992 through Aug. 31, 1996, Competitive Research Grants Office (NRI) GEOV, grant No. 92-37204-7838 (Available on-line on or before Jul. 19, 1998).

Dickerson et al., "Serotypic Variation Among Isolates of *Ichthyophthirius multifiliis* Based on Immobilization," *J. Euk. Microbiol., 40*(6):816-820 (1993).

Dickerson et al., "Vaccination against Ich," *Aquaculture, 127*(2-3):278-280 (1994).

Dickerson et al., "Molecular Approaches Toward the Control of Ichthyophthirius Infection," CRIS report, NRI competitive grant No. 95-37204-2139, Sep. 1, 1995 to Aug. 31, 2000, 5 pages (1995) (Available on-line on or before Jul. 19, 1998).

Dickerson et al., "Immune Response of Fishes to Ciliates," *Ann. Rev. Fish Dis., 6*:107-120 (1996).

Dickerson et al., "Display of an Ichthyophthirius I-Antigen on the Surface of Transformed Tetrahymena thermophila for Use as a Novel Vaccine in Fish," Abstract, Ann. Meeting, Conference of Research Workers in Animal Diseases, Nov. 8-10, Chicago (1998).

Englund, "The Structure and Biosynthesis of Glycosyl Phosphatidylinositol Protein Anchors," *Ann. Rev. Biochem., 62*:121-138 (1993).

Ferguson, "What Can GPI Do for You?" *Parasitol. Today, 10*(2):48-52 (1994).

Frohman, "RACE: Rapid Amplification of cDNA Ends," *PCR Protocols: A Guide to Methods and Applications*, Innis, et al., eds., Academic Press, San Diego, Title page, publication page, table of contents and pp. 28-38 (1990).

Frohman, "RACE: Rapid Amplification of Complementary DNA Ends for Generation of Full-Length Complementary DNAs: Thermal RACE," *Meth. Enzymol., 218*:340-356 (1993).

Gaertig et al., "Perspectives on Tubulin Isotype Function and Evolution Based on the Observation that *Tetrahymena thermophila* Microtubules Contain a Single α- and β-Tubulin," *Cell Mot. Cytoskel., 25*:243-253 (1993).

Gaertig et al., "Electroporation-mediated replacement of a positively and negatively selectable β-tubulin gene in *Tetrahymena thermophila*," *Proc. Natl., Acad. Sci. USA, 91*:4549-4553 (1994).

Gaertig et al., "High frequency vector-mediated transformation and gene replacement in *Tetrahymena*," *Nuc. Acids Res., 22*(24):5391-5398 (1994).

Gaertig et al., "Acetylation of Lysine 40 in α-tubulin is Not Essential in *Tetrahymena thermophila*," *J. Cell. Biol., 129* (5):1301-1310 (1995).

Gaertig, "New approaches for gene knockout, transgene expression and surface display in the ciliate *Tetrahymena thermophilia,*" *Jap. J. of Protozool.*, 32(1):11-19 (Mar. 13, 1999).

Gaertig et al., "Surface display of a parasite antigen in the ciliate *Tetrahymena thermophila,*" *Nature Biotechnology*, 17(5):462-465 (May, 1999).

Gall, ed., *The Molecular Biology of Ciliated Protozoa*, Academic Press, Inc., Orlando, Title page, publication page and table of contents only, 4 pages (1986).

Garg et al., "Delivery by *Trypanosoma cruzi* of Proteins into the MHC Class 1 Antigen Processing and Presentation Pathway," *J. Immunol.*, 158:3293-3302 (1997).

Glover, ed., *DNA Cloning, vol. I: a practical approach*, IRL Press, Oxford, Title page, publication page and table of contents only, 8 pages (1985).

Glover, ed., *DNA Cloning, vol. II: a practical approach*, IRL Press, Oxford, Title page, publication page and table of contents only, 7 pages (1985).

Gorovsky, "Macro- and Micronuclei of *Tetrahymena pyriformis*: A Model System for Studying the Structure and Function of Eukaryotic Nuclei," *J. Protozool.*, 20(1):19-25 (1973).

Goven et al., "Protection of channel catfish, *Ictalurus punctatus* Rafinesque, against *Ichthyophthirius multifiliis* Fouquet by immunization," *J. Fish Biol.*, 17:311-316 (1980).

Gower et al., "Alternative Splicing Generates a Secreted Form of N-CAM in Muscle and Brain," *Cell*, 55(6):955-964 (1988).

Grossman et al., eds., *Methods in Enzymology vol. 65, Nucleic Acids Part I*, Academic Press Inc., New York, Title page, publication page and table of contents only, 8 pages (1980).

Gubler et al., "Second-Strand cDNA Synthesis: mRNA Fragments as Primers," *Meth. Enzymol.*, 152:330-335 (1987).

Haddad et al., "Analysis of exocytosis mutants indicates close coupling between regulated secretion and transcription activation in *Tetrahymena,*" *Proc. Natl. Acad. Sci. USA*, 94(20):10675-10680 (1997).

Hames et al., eds., *Nucleic acid hybridization: a practical approach*, IRL Press, Oxford, Title page, publication page and table of contents only, 8 pages (1985).

He et al., "Protection of goldfish against *Ichthyophthirius multifiliis* by immunization with a recombinant vaccine," *Aquacult.*, 158:1-10 (1997).

Hedrick et al., "Passive Transfer of Sera with Antivirus Neutralizing Activity from Adult Channel Catfish Protects Juveniles from Channel Catfish Virus Disease," *Trans. Amer. Fish Soc.*, 116:277-281 (1987).

Hines et al., "Ichthyophthiriasis in the mirror carp *Cyprinus carpio* (L.) V. Acquired immunity," *J. Fish Biol.*, 6:373-378 (1974).

Hopp et al., "A Short Polypeptide Marker Sequence Useful for Recombinant Protein Identification and Purification," *Biotechnology*, 6:1204-1210 (1988).

Hünseler et al., "Genetic Characterization of the Secretory Mutant MS-1 of *Tetrahymena thermophila*: Vacuolarization and Block in Secretion of Lysosomal Hydrolases Are Caused by a Single Gene Mutation," *Dev. Genet.*, 13:167-173 (1992).

Innis et al., "Expression, Glycosylation, and Secretion of an *Aspergillus* Glucoamylase by *Saccharomyces cerevisiae,*" *Science*, 228:21-26 (1985).

Jones et al., "Oral Delivery of Micro-Encapsulated DNA Vaccines," *Dev. Biol. Stand.*, 92:149-155 (1998).

Kahn et al., "Transformation of *Tetrahymena thermophila* by microinjection of a foreign gene," *Proc. Natl. Acad. Sci. USA*, 90(20):9295-9299 (1993).

Kavenoff et al., "Chromosome-Sized DNA Molecules from *Drosophila,*" *Chromosoma*, 41:1-27 (1973).

Kiy et al., "Continuous high-cell-density fermentation of the ciliated protozoon *Tetrahymena* in a perfused bioreactor," *Appl. Microbiol. Biotechnol.*, 38:141-146 (1992).

Krieg et al., "CpG motifs in bacterial DNA trigger direct B-cell activation." *Nature*, 374:546-549 (1995).

Krieg et al., "The role of CpG dinucleotides in DNA vaccines," *Trends Microbiol.*, 6(1):23-27 (1998).

Krug et al., "First-Strand cDNA Synthesis Primed with Oligo(dT)," *Meth. Enzymol.*, 152:316-325 (1987).

La Flamme et al., "Expression of mammalian cytokines by *Trypanosoma cruzi* indicates unique signal sequence requirements and processing," *Mol. Biochem. Parasitol.*, 75:25-31 (1995).

Lambris et al., "Third Component of Trout Complement," *J. Immunol.*, 151(11):6123-6134 (1993).

Lee et al., "Missense Mutations at Lysine 350 in β2-Tubulin Confer Altered Sensitivity to Microtubule Inhibitors in *Chlamydomonas,*" *Plant Cell*, 2(11):1051-1057 (1990).

Leong et al., "DNA-polycation nanospheres as non-viral gene delivery vehicles," *J. Controlled Release*, 53:183-193 (1998).

Lin et al., "Purification and Partial Characterization of Immobilization Antigens from *Ichthyophthirius multifiliis,*" *J. Protozool.*, 39(4):457-463 (1992).

Lin et al., "Passive Immunization of Channel Catfish (*Ictalurus punctatus*) against the Ciliated Protozoan Parasite *Ichthyophthirius multifiliis* by Use of Murine Monoclonal Antibodies," *Infect. Immun.*, 64(10):4085-4090 (1996).

Løvlie et al., "Molecular evidence for somatic recombination in the ribosomal DNA of *Tetrahymena thermophila,*" *Proc. Natl . Acad. Sci. USA*, 85:5156-5160 (1988).

MacRae, "Tubulin post-translational modifications: Enzymes and their mechanisms of action," *Eur. J. Biochem.*, 244:265-278 (1997).

Martindale, "Codon Usage in *Tetrahymena* and Other Ciliates," *J. Protozool.*, 36(1):29-34 (1989).

Miller, *Experiments in Molecular Genetics*, Cold Spring Harbor Laboratory, Cold Spring Harbor, New York, Title page, publication page and table of contents only, 8 pages (1972).

Nash et al., "Variant-specific surface proteins of *Giardia lamblia* are zinc-binding proteins," *Proc. Natl. Acad. Sci. USA*, 90(12):5489-5493 (1993).

Nielsen et al., "Identification of prokaryotic and eukaryotic signal peptides and prediction of their cleavage sites," *Prot. Engin.*, 10:1-15 (1996).

Old et al., *Principles of Gene Manipulation, An Introduction to Genetic Engineering*, University of California Press, Berkeley, Title page, publication page and table of contents only, 3 pages (1981).

Pan et al., "Tandem repeats of the 5' non-transcribed spacer of *Tetrahymena* rDNA function as a high copy number autonomous replicons in the macronucleus but do not prevent rRNA gene dosage regulation," *Nuc. Acids Res.*, 23(9):1561-1569 (1995).

Pan et al., "Replication of an rRNA Gene Origin Plasmid in the *Tetrahymena thermophila* Macronucleus is Prevented by Transcription through the Origin from an RNA Polymerase I Promoter," *Mol. Cell. Biol.*, 15(6):3372-3381 (1995).

Parker, *Studies on the Natural History of Ichthyophthirius multifiliis Fouquet 1876, an Ectoparastic Ciliate of Fish*, Ph.D. Dissertation, The University of Maryland, College Park, MD, 94 pages (1965).

Peters-Regehr et al., "Primary Structure and Origin of a Predator Released Protein that Induces Defensive Morphological Changes in *Euplotes*," *Europ. J. Protistol.*, 33:389-395 (1997).

Prat et al., "Nucleotide Sequence of the *Parmecium primaurelia* G Surface Protein, a Huge Protein with a Highly Periodic Structure," *J. Mol. Biol.*, 189(1):47-60 (1986).

Preer, "Surface Antigens of *Paramecium*," *The Molecular Biology of Ciliated Protozoa*, Gall, ed., Academic Press, Orlando, Title page, publication page, table of contents and pp. 301-339 (1986).

Prescott, "The DNA of Ciliated Protozoa," *Microbiol. Rev.*, 58(2):233-267 (1994).

Raftery et al, "Systematic alterations in the anticodon arm make tRNA$^{\text{Glu}}$-Su$_{\text{OC}}$ a more efficient suppressor," *EMBO J.*, 6(5):1499-1506 (1987).

Redeker et al., "Polyglycylation of Tubulin: A Post-translational Modification in Axonemal Microtubules," *Science*, 266:1688-1691 (1994).

Reisner et al., "Concerning the Tertiary Structure of the Soluble Surface Proteins of Paramecium," *Biochemistry*, 8(11):4637-4644 (1969).

Reymond et al., "Anchoring of an Immunogenic *Plasmodium falciparum* Circumsporozoite Protein on the Surface of *Dictyostelium discoideum*," *J. Biol. Chem.*, 270(21):12941-12947 (1995).

Roy et al., "Oral gene delivery with chitosan-DNA nanoparticles generates immunologic protection in a murine model of peanut allergy," *Nature Med.*, 5(4):387-391 (Apr., 1999).

Rusch et al., "Protein transport via amino-terminal targeting sequences: common themes in diverse systems (Review)," *Mol. Membr. Biol.*, 12(4):295-307 (1995).

Rusconi et al., "The anticodon is the signal sequence for mitochondrial import of glutamine tRNA in *Tetrahymena*," *Genes Dev.*, 10(22):2870-2880 (1996).

Sambrook et al., *Molecular Cloning: A Laboratory Manual*, Second Edition, Books 1-3, Cold Spring Harbor Laboratory Press, Cold Spring Harbor, New York, Title page and table of contents only, 29 pages (1989).

Saraste et al., "P-loop—a common motif in ATP- and GTP-binding proteins," *Trends Biochem. Sci.*, 15:430-434 (1990).

Schleif et al., *Practical Methods in Molecular Biology*, Springer-Verlag, New York, Title page, publication page and table of contents only, 7 pages (1981).

Seeber et al., "Analysis of *Toxoplasma gondii* stably transfected with a transmembrane variant of its major surface protein, SAG1," *J. Cell Sci.*, 111:23-29 (1998).

Setlow et al., eds., *Genetic Engineering: Principles and Methods, vol. 1*, Plenum Press, New York, Title page, publication page and table of contents only, 4 pages (1979).

Smith et al., "Characterization of the T, L, I, S, M and P Cell Surface (Immobilization) Antigens of *Tetrahymena thermophila*: Molecular Weights, Isoforms, and Cross-Reactivity of Antisera," *J. Protozool.*, 39(3):420-428 (1992).

Spangler et al., "The Nucleotide Sequence of the 17 S Ribosomal RNA Gene of *Tetrahymena thermophila* and the Identification of Point Mutations Resulting in Resistance to the Antibiotics Paromomycin and Hygromycin," *J. Biol. Chem.*, 260(10):6334-6340 (1985).

Stemmer et al., "Single-step assembly of a gene and entire plasmid from large numbers of oligodeoxyribonucleotides," *Gene*, 164:49-53 (1995).

Suggs et al., "Use of synthetic oligonucleotides as hybridization probes: Isolation of cloned cDNA sequences for human $\beta_2$-microglobulin," *Proc. Natl. Acad. Sci. USA*, 78(11):6613-6617 (1981).

Sundermann et al., "Recognition of Prey by Suctoria: The Role of Cilia," *J. Protozool.*, 33(4):473-475 (1986).

Sunyer et al., "Multiple forms of complement C3 in trout that differ in binding to complement activators," *Proc. Natl. Acad. Sci. USA*, 93:8546-8551 (1996).

Tobin et al., "Transfected *Leishmania* Expressing Biologically Active IFN-γ," *J. Immunol.*, 150(11):5059-5069 (1993).

Tondravi et al., "Transformation of *Tetrahymena thermophila* by microinjection of ribosomal RNA genes," *Proc. Natl. Acad. Sci. USA*, 83:4369-4373 (1986).

Tondravi et al., "Molecular Characterization of SerH3, a *Tetrahymena thermophila* Gene Encoding a Temperature-Regulated Surface Antigen," *Mol. Cell. Biol.*, 10(11):6091-6096 (1990).

Viele et al., "Adoptive transfer of immunity against *Vibrio anguillarum* in rainbow trout, *Salmo gairdneri* Richardson, vaccinated by the immersion method," *J. Fish Biol.*, 17:379-386 (1980).

Williams et al., "Recombinant glycoprotein production in the slime mould *Dictyostelium discoideum*," *Curr. Opin. Biotechnol.*, 6:538-542 (1995).

Wirtz et al., "Inducible Gene Expression in Trypanosomes Mediated by a Prokaryotic Repressor," *Science*, 268:1179-1183 (1995).

Woo, "Immunization Against Parasitic Diseases of Fish," *Dev. Biol. Stand.*, 90:233-241 (1997).

Wu, ed., *Methods in Enzymology vol. 68 Recombinant DNA*, Academic Press Inc, New York, Title page, publication page and table of contents only, 6 pages (1979).

Wu et al., eds., *Methods in Enzymology vol. 100 Recombinant DNA Part B*, Academic Press Inc. New York, Title page, publication page and table of contents only, 5 pages (1983).

Wu et al., eds., *Methods in Enzymology vol. 101 Recombinant DNA Part C*, Academic Press Inc, New York, Title page, publication page and table of contents only, 6 pages (1983).

Xu et al., "Analysis of the Soluble and Membrane-bound Immobilization Antigens of *Ichthyophthirius multifiliis*," *J. Euk. Microbiol.*, 42(5):558-564 (1995).

Yao et al., "Accurate Processing and Amplification of Cloned Germ Line Copies of Ribosomal DNA Injected into Developing Nuclei of *Tetrahymena thermophila*," *Mol. Cell. Biol.*, 9(3):1092-1099 (1989).

Yao et al., "Transformation of *Tetrahymena* to cycloheximide resistance with a ribosomal protein gene through sequence replacement," *Proc. Natl. Acad. Sci. USA*, 88(21):9493-9497 (1991).

Young et al., "Efficient isolation of genes by using antibody probes," *Proc. Natl. Acad. Sci. USA*, 80:1194-1198 (1983).

Yu et al., "Circular ribosomal DNA plasmids transform *Tetrahymena thermophila* by homologous recombinant with endogenous macronuclear ribosomal DNA," *Proc. Natl. Acad. Sci. USA*, 85:5151-5155 (1988).

Yu et al., "Transformation of *Tetrahymena thermophila* with a mutated circular ribosomal DNA plasmid vector," *Poc. Natl. Acad. Sci. USA*, 86:8487-8491 (1989).

Zhang et al., "Cysteine-Dependent Zinc Building by Membrane Proteins of *Giardia lamblia*," *Infect. Immun.*, *61*(2):520-524 (1993).

GU, "Analysis of the Expression and Function of β-tubulin in *Tetrahymena thermophila*," Dissertation by Long Gu. Dept. of Biology, The College Arts and Sciences, Univ. of Rochester, Rochester, New York (1995) pp. i-xx and 1-167.

* cited by examiner

Fig. 1

G5 Wild-type

SEQ ID NO: 44

```
         10         20         30         40         50         60         70         80         90        100        110        120
ATGAAAAATA ATATTTTAGT AATAITTGATT ATTTCATTAT TTATCAATTA AATTAAATCT GCTAATTGTC CTGTTGGAAC TGAAACTAAC ACAGCCGGAT AAGTTGATGA TCTAGGAACT
        130        140        150        160        170        180        190        200        210        220        230        240
CCTGCAAATT GTGTTAATTG TTAGAAAAAC TTTTATTATA ATAATGCTGC TGCTTTCGTT CCTGGTGCTA ACCTTGTCCA GTACGTGTAC TAAAAAAAG ATGCTGGTGC TTAACCAAAT
        250        260        270        280        290        300        310        320        330        340        350        360
CCACCTGCTA CTGCTAATTT AGTCACATAA TGTAACGTTA AATGCCCTGC TGGTACCGGA ATTGCAGGTG GAGCAACAGA TTATCAGCA AATCACAG AATGTGTTAA TTGTAGAATT
        370        380        390        400        410        420        430        440        450        460        470        480
AATTTTTATA ATGAAAATGC TCCAAATTTT AATGCAGGTG CTAGTACATG CACAGCTTGT CCGGTAAACA GAGTTGGTGG TGCATTGACT GCTGGTAATG CCGGTACCAT AGTCGCATAA
        490        500        510        520        530        540        550        560        570        580        590        600
TGTAACGTCG CATGTCCTAC TGGTACTGCA CTTGATGATG GAGTAACTAC TGATTATGTT AGATCATTCA CAGAATGTGT TAAATGTATA CTTAACTTTT ACTATAATGG TAATAATGGT
        610        620        630        640        650        660        670        680        690        700        710        720
AATACTCCTT TCAATCCAGG TAAAAGTTAA TGCACCACCT GTCCGGCAAT TAAACCTGCT AATGTTGCTT AAGCTACTTT AGGTAATGAT GCTACAATAA CCGCATAATG TAACGTTGCA
        730        740        750        760        770        780        790        800        810        820        830        840
TGCCCTGATG GTACTATAAG TGCTGCTGGA GTAAATAATT GGGTAGCACA AAACACTGAA TGTACTAATT GTGCTCCTAA CTTTTACACT AATAATGCTC CTAATTTCAA TCCAGGTAAT
        850        860        870        880        890        900        910        920        930        940        950        960
AGTACATGCC TACCTTGCCC AGCAATATAA GATTATGGTG CTGAAGGCAC TGCAGGTGGT GCCGCTACTT TAGCCAAATA ATGTAATATT GCATGCCCTG ATGGTACTGC AATTGCTAGT
        970        980        990       1000       1010       1020       1030       1040       1050       1060       1070       1080
GGAGCAACTA ATTATGTAAT ATTATAAACA GAATGTCTGC ATTGTGCTGC TAACTTTTAT TTTGATGGTA ATAATTTCTA GGCAGGAAGT AGTAGATGCA AAGCATGTCC AGCAAATAAA
       1090       1100       1110       1120       1130       1140       1150       1160       1170       1180       1190       1200
GTTTAAGGCG CTGTAGCAAC TGCAGGTGGT ACTGCTACTT TAATTGCATA ATGTGCCCTT GAATGCCCTG CTGTACTGT ACTCACCGAT GGAACAACAT CTACTTATAA ATAAGCAGCA
       1210       1220       1230       1240       1250       1260       1270       1280       1290       1300       1310       1320
TCTGAATGTG TTAAATGTGC TGCCAACTTG TATACTACAA AATAAAACTGA TTGGGTAGCA GGTATTGATA CATGCTACTAG TTGTAATAAA AATTAACTT CTGGCCCTGA AGCTAATTTA
       1330       1340       1350       1360       1370       1380       1390       1400       1410       1420       1430       1440
CCTGAATCTG CTAAAAAAA TATATAAATGT GATTCGCTA AATTTTTATC AATTTCCTTA TTATTGATT CTTATTATTT ATTATGATGA
```

Coding region: nucleotides 1-1404

*Fig. 2a*

G5 SYNTHETIC

SEQ ID NO: 102

```
         10         20         30         40         50         60         70         80         90        100        110        120
ATGAAGAACA ACATCCTGGT GATCCTGATC ATCTCTCTGT TCATCAACCA GATCAAGTCT GCTAACTGTC CTGTCGGAAC CGGAGACCAAC ACCGCTGGAC AGGTGGAGGA CCTGGAACC
        130        140        150        160        170        180        190        200        210        220        230        240
CCTGCTAACT GTGTGAACTG TCAGAAGAAC TTCTACTACA ACAACGCTGA CAAACGCTGC CCTTCTCGTG CCTGGAGCTT CTACTGTGTG CAGAAGAAGG ACGCTGAAGC TCAGCCTAAC
        250        260        270        280        290        300        310        320        330        340        350        360
CCTGCTGCTA CCGCTAACCT GGTGACCCAG TGTAACGTGA AGTGTCCTGC TGGAACCGCT ATCGCTGAGA CTACGCTGCT ATCATCACCG AGTGTGTGAA CTGTCCATC
        370        380        390        400        410        420        430        440        450        460        470        480
AACTTCTACA ACGAGAACGC TCCTAACTTC CCTGTGAACT CTTCTACCTG TACCGCTTGT CCTGTGAACT GCGTGGGAGG AGTGCTGAAC GCTGGAAACG CTGCTACCAT CGTGGCTCAG
        490        500        510        520        530        540        550        560        570        580        590        600
TGTAACGTGG CTTGTCCTAC CGGAACCGCT CTGGACGACG GAGTGACCAC CGACTACGTG CCTGTCTTCA CGGCTCTTTCA GAAGTGTCGC CTGAACTTCT ACTACAACGG AAACAACGA
        610        620        630        640        650        660        670        680        690        700        710        720
AACACCCCTT TCAACCTGG AAAGTCTCAG TGTACCCCTT GTCCTGCTAT CAAGCCTGCT AACGTGGCTC AGGCTACCCT GGGAAACGAC GCTACCATCA CCGCTCAGTG TAACGTGGCT
        730        740        750        760        770        780        790        800        810        820        830        840
TGTCCTGACG GAACCATCTC TGCTGCTACA GTGAACAACT GGGTGCCTCA GAACACCGAG TGTACCAACT CTTCTACAAC AACAAGGCTC CTAACTTCAA CCCTGAAAC
        850        860        870        880        890        900        910        920        930        940        950        960
TCTACCTGTC TGCCTTGTCC TGCTAACAAG GACTACGGAG CTGAGGTAC GCTGGAGGA GTGTAAGCA GCTGCTACCG GTGTAACATC GCTTGTCCTG ACGGAACCGC TATCGCTTCT
        970        980        990       1000       1010       1020       1030       1040       1050       1060       1070       1080
GGAGCTACCA ACTACGTGAT CCTGCAGACA GAGTGTCTGA ACTGTCTAC TAACTTCTAC TTCGACGGAA ACAACTTCCA GGCTGGATCT TCTCGTGTCC TGCTAACAAG
       1090       1100       1110       1120       1130       1140       1150       1160       1170       1180       1190       1200
GTGCAGGGAG CTTGGCTAC CCCTGGAGGA ACCGCTACCC TGATCGCTCA GTGTGCTCA CTGTCTCTG GAGTCTCCTG CTGAACCGAC GCTAACCACCT CTACCTACAA GCAGGCTGCT
       1210       1220       1230       1240       1250       1260       1270       1280       1290       1300       1310       1320
TCTGAGTGTG TGAAGTGTC TGCTAACTTC TACACCACCA AGCAGACCGA CTGGGTGGCT GGAATCGACA CCTGTAACCTC TTGTAACGAAG AAGCTGACCT CTGGAGCTGA GGCTAACCTG
       1330       1340       1350       1360       1370       1380       1390       1400       1410
CCTGAGTCTG CTAAGAAGAA CATCCAGTGT GACTTCGCTA ACTTCCTGTC TATCTCTCTG CTGCTGATCT CTTACTACCT GCTGTAATAA
```

Coding region: nucleotides 1–1404

Fig. 2b

Sequence Alignment of 48 kD G1 i-antigen
and 55 kD G5 i-antigen protein sequences

| | | | | SEQ ID NO | Conserved regions |
|---|---|---|---|---|---|
| SEQ ID NO: 6 | G1 | 1 | MKYNILLILISLFINELRAVPCPDGTQT-QAG-LTDVGAADLGTCVNCRPNFYN---- | 90 | MKYNILLILISLFIN |
| SEQ ID NO: 7 | G5 | 1 | MKNNILVILIISLFINQIKSANCPVGTETNTAGVDDLGTP--ANCVNCQKNFYYNNAAA | 91 | MKNNILVILIISLFIN |
| | | |  *  *.:::. **  ::*: *:. .*.. :**  | | |
| | G1 | 55 | --GGAA------QGEANGNQP------------------------------- | | |
| | G5 | 59 | FVPGASTCTPCPQKKDAGAQPNPPATANLVTQCNVKCPAGTAIAGGATDYAAIITECVNC | | |
| | | | *:                                                  | | |
| | G1 | 68 | ---F-----AAN-NAARGICVPCQINRVGSVTNAGDLATLATQCSTQCPTGTALDDGVT DV | 92 | CPTGTALDDGVT |
| | G5 | 119 | RINFYNENAPNFNAGASTCTACPVNRVGGALTAGNAATIVAQCNVACPTGTALDDGVT TD | | |
| | | | **.: :.:. *  :****  * ::*: ** ::*:   .::***********    | | |
| | G1 | 120 | FDRSAAQCVKCKPNFYYNGGSPQGEAPGVQVFAAGAAAAGVAAVTSQCVPCQLNK--NDS | 93 | CVKCKPNFYYNG |
| | G5 | 179 | YVRSFTECVKCRLNFYYNGNN--GNTP----FNPGK-------SQCTPCPAIKPANVA | 94 | CVKCRLNFYYNG |
| | | | :.**:*: ****  ******.  *. *   *::      . *  **. :  * .    | | |
| | G1 | 178 | PATAGAQANLATQCSNQCPTGTVLDDGVTLVFNTSATLCVKCRPNFYYNGGSPQGEAPGV | | |
| | G5 | 224 | QATLGNDATITAQCNVACPDGTISAAGVN-NWVAQNTECTNCAPNFYNNN-----AP-- | | |
| | | | *** :.  ** ** :.:** ** :.:*.   * *:.   * .***** .        | | |
| | G1 | 238 | QVFAAGAAAAGVAAVTSQCVPCQINKND-SPATAGAQANLATQCSTQCPTGTAIQDGVTL | | |
| | G5 | 295 | -NFNPG------NSTCLPCPANKDYGAEATAGAGAATLAKQCNIACPDGTAIASGATN | | |
| | | | . * .       .:  :: *:    *** :.*    ****:.... : | | |
| | G1 | 297 | VFSNSSTQCSQCIANYFFNG-NFEAGKSQCLKCPVSKTTPAHAP-GNTATQATQCLTT CP | 95 | CPAGTVLDDGT |
| | G5 | 325 | -YVILQTECLNCAANFYFDGNNFQAGSSRCKACPANKVQGAVATAGGTATLIAQCALE CP | 96 | CPAGTVLTDGT |
| | | | : :: :**..* ** :*:* :.*:**.   .* . *. **::*  **   *  | | |
| | G1 | 355 | AGTVLDDGT TNFVASATECTKCSAGFFASKTTGF TAGTDTCTECTKKLTSGA TAKVYAE | 97 | AGTDTCTECTKKLTSGATA |
| | G5 | 384 | AGTVLTDGT STYKQAASECVKCAANFYTTKQTDWV AGIDTCTSCNKKLTSGA EANLPES | 98 | AGIDTCTSCNKKLTSGAEA |
| | | | ** : :.: :.:.::.*:::*::::  **:* *****  :   .   | | |
| | G1 | 415 | ATQKVQCAST FAKFLSISLLFISFYLL | 99 | FAKFLSISLLFISFYLL |
| | G5 | 444 | AKKNIQCD--- FANFLSISLLLISYYLL | 100 | FANFLSISLLLISYYLL |
| | | | *.::.:**   ** ************: | | |

Sequence Alignment of 48 kD G1 i-antigen
and 55 kD G5 i-antigen nucleotide sequences

```
G1  SEQ ID NO: 1  ATGAAATATAATATTTTATTAATTTTAATTATTTCTTTATTTATTAATGAATTAAGAGCT
G5  SEQ ID NO: 3  ATGAAAAATAATATTTTAGTAATATTGATTATTTCATTATTTATCAATTAAATTAAATCT
                  *****  ************  ****  **  ********  ********  *** | ** * * * **

G1                GTTCCATGTCCTGATGGTACTTAGACTCA---AGCTGGAT----TGACTGATGTAGGTGC
G5                GCTAATTGTCCTGTTGGAACTGAAACTAACACAGCCGGATAAGTTGA-TGATCTAGGAAC
                  * *  *******  ***  ***  *  ***  *    ***  ****    ***  ****  ****  *

G1                TGCTGATCTTGGTACTTGTGTTAATTGC-AGACCTAATTTTTACTATAATGGTGGTGCTG
G5                TCCT------GCAAATTGTGTTAATTGTTAGAAA-AACTTTTATTATAATAATGCTGCTG
                  *  **     *  *  *************  ***  ** *****  ******  **  *****

G1                CTTAAGGAGAAGCTAATGGTAATTAACCTTTCGCAGCAAATAATGCTGCTAGAGGTATAT
G5                CTT------------------------TCGTTCC------TGGTGCTAG---TACGT
                  ***                         ***   *       ** ******    **  *

G1                GTGTACCATG-CCA-AATAAACAGA-GTAGGCTCTGTTACCAA-TGCAGGTG--ACTTAG
G5                GTACACCTTGTCCATAAAAAAAAGATGCTGGTGCT-TAACCAAATCCACCTGCTACT--G
                  **  ***  **  ***  **   ***  ***  *  **  **  *  ******  *  **  **  ***   *

G1                CTACTTTAGCCACATAATGCAGTACTTAATGTCCTACTGGCACTGCACTTGATGATGGAG
G5                CTAATTTAGTCACATAATGTAACGTTAAATGCCCTGCTGGTACCGCAATTGCAGGTGGAG
                  ***  *****  *********  *   *  ****  ***  ****  **  ***  ***    *  *****

G1                TGACAGATGTTTTTG--ATAGATCAGCCGCATAATGTGTTAAATGCAAACCTAACTTTTA
G5                CAACAGATTATGCAGCAATA-ATCA----CAGAATGTGTTAATTGTAGAATTAATTTTTA
                  ******   *    *  ***  ****  **  **********  **  *  *   ***  *****

G1                CTATAATGGTGGTTCTCCTTAAGGTGAAGCTCCTGGCGTTTAAGTTTTTGCTGCTGGTGC
G5                ---TAATGA-----------AA----ATGCTCC---------AAATTTTAA---------
                     *****         **    *  *****            *  ****

G1                TGCCGCTGCAGGTGTTGCTGCCGTTACTAGTTAATGTGTACCTTGCCAACTAAACAAAAA
G5                ------TGCAGGTG-----------CTAGTACATGCACAGCTTGTCCGGTAAACAGAGT
                        ********      *****  ***  *  ****  *  ******  *

G1                CGATTCTCCTGCCACTGCAGGT---GCCTAAGCTAATTTAGCCACATAATGTAGCAATTA
G5                TGGTGGTGCATTGACTGCTGGTAATGCC---GCTACCATAGTCGCATAATGTAACGTCGC
                  *  *   *  *    *****  ***  ***    ***   ****   ***  *********  *
```

```
G1  ATGTCCTACTGGCACTGTACTTGATGATGGAGTGACACTTGTTTTTAATACATCAGCCAC
G5  ATGTCCTACTGGTACTGCACTTGATGATGGAGTAACTACTGATTATGTTAGATCATTCAC
    ********** **** ***************** ** ** ** *  ** ****  ***

G1  ATTATGTGTTAAATGCAGACCTAACTTTTACTATAATGGT------GGTT---CTCCTTA
G5  AGAATGTGTTAAATGTAGACTTAACTTTTACTATAATGGTAATAATGGTAATACTCCTTT
    *  *********** **** ********************      ***   ******

G1  ------AGGTGAA------------------------------GCTCCTGGCGTTTA
G5  CAATCCAGGTAAAAGTTAATGCACACCTTGTCCGGCAATTAAACCTGCTAATGTTGCTTA
          **** **                               ***  **  * ***

G1  AG----TTT--------------------------------TTGC------TGCTGG
G5  AGCTACTTTAGGTAATGATGCTACAATAACCGCATAATGTAACGTTGCATGCCCTGATGG
    **    ***                                ****     **  ***

G1  TGCT------GCCGCTGCAG---------GTGTTGC------------------------
G5  TACTATAAGTGCTGCTGGAGTAAATAATTGGGTAGCACAAAACACTGAATGTACTAATTG
    * **      ** **** **         * ** **

G1  ------------------------------------TGCCGTTACTAGTTAATGTGT
G5  TGCTCCTAACTTTTACAATAATAATGCTCCTAATTTCAATCCAGGTAATAGTACATGCCT
                                        *  *  **  ****  *** * *

G1  ACCTTGCCAAATAAACAAAAACGATTCTCCTG---CCACTGCAGGTGCCTAAGCTAATTT
G5  ACCTTGCCCAGCAAATAAAGATTATGGTGCTGAAGCCACTGCAGGTGGTGCCGCTACTTT
    ******** *  *** *    **** * * *    *************  *** ** ***

G1  AGCCACATAATGCAGTACTTAATGTCCAACTGGCACTGCAATT-CAAGACGGAGTGACAC
G5  AGCCAAATAATGTAATATTGCATGCCCTGATGGTACTGCAATTGCTAGT-GGAGCAAC--
    ***** ****** *  * *   ** *  * ** ********** *  **  ****  **

G1  TTGTTTTTAGTAAT-TCATCCACATAATGTTCTTAAT-GCATTGCTAATTACTTTTTTAA
G5  -TAATTAT-GTAATATTATAAACAGAATGT-CTAAATTGTGCTGCTAACTTTTATTTTGA
     *  **   ****  * **  ** ***** *** **  *  *****  ***** ****

G1  TGGTAAT---TTCGAAGCAGGTAAAAGTTAATGTTTAAAG--TGTCCAGTAAGTAAAACT
G5  TGGTAATAATTTCTAGGCAGGAAGTAGTAGATGC--AAAGCATGTCCAGCAAATAAAGTT
    *******   *** *  ***** * * ***      ****  ****** **  *** **

G1  A------CTCCAGCACATGCTCCAGGTAATACTGCTACTTAAGCCACATAATGT----TT
G5  TAAGGCGCTGTAGCAA---CTGCAGGTGGTACTGCTACTTTAATTGCATAATGTGCCCTT
     *   *  *****       ********* ********* *  * ********    **

G1  GACCACATGTCCTGCTGGTACAGTACTTGATGATGGAACATCAACTAATTTTGTAGCTTC
G5  GA----ATGCCCTGCTGGTACTGTACTCACCGATGGAACAACATCTACTTATAAATAAGC
    **    *** *********** *****    ********* ** *** * *  * *  *

G1  CGCAACTGAATGTACTAAATGTTCTGCTGGCTTTTTTGCATCAAAAACAACTGGTTTTAC
G5  AGCATCTGAATGTGTTAAATGTGCTGCCAACTTTTATACTACAAAATAAACTGATTGGGT
     ***  ******** ****** ****    ***** * ** ***** ****** *

G1  AGCAGGTACTGATACATGTACTGAATGTACTAAAAAATTAACTTCTGGTGCCACAGCTAA
G5  AGCAGGTATTGATACATGTACTAGTTGTAATAAAAAATTAACTTCTGGCGCTGAAGCTAA
    ********  *********** * * *** ******************  *   *****

G1  AGTATATGCTGAAGCTACTCAAAAAG---TATAATGCGCCTCCACTACTTTCGCTAAATT
G5  TTTAC---CTGAATCTGCTAAAAAAAATATATATAATGTG---------ATTTCGCTAATTT
     * *    ****  ** **  ****    ***** **          ********  **

G1  TTTATCGATTTCCTTATTATTTATTTCTTTCTATTTATTG
G5  TTTATCAATTTCCTTATTATTGATTTCTTATTATTTATTA
    ****** **************  ****** ***** ***
```

𝓕𝓲𝓰. 3b₂

55 KD i-antigen protein

```
              10         20         30         40         50         60
SEQ ID NO: 7  MKNNILVILI ISLFINQIKS ANCPVGTETN TAGQVDDLGT PANCVNCQKN FYYNNAAAFV 70         80         90        100        110        120
              PGASTCTPCP QKKDAGAQPN PPATANLVTQ CNVKCPAGTA IAGGATDYAA IITECVNCRI 130        140        150        160        170        180
              NFYNENAPNF NAGASTCTAC PVNRVGGALT AGNAATIVAQ CNVACPTGTA LDDGVTTDYV 190        200        210        220        230        240
              RSFTECVKCR LNFYYNGNNG NTPFNPGKSQ CTPCPAIKPA NVAQATLGND ATITAQCNVA 250        260        270        280        290        300
              CPDGTISAAG VNNWVAQNTE CTNCAPNFYN NNAPNFNPGN STCLPCPANK DYGAEATAGG 310        320        330        340        350        360
              AATLAKQCNI ACPDGTAIAS GATNYVILQT ECLNCAANFY FDGNNFQAGS SRCKACPANK 370        380        390        400        410        420
              VQGAVATAGG TATLIAQCAL ECPAGTVLTD GTTSTYKQAA SECVKCAANF YTTKQTDWVA 430        440        450        460        470        480
              GIDTCTSCNK KLTSGAEANL PESAKKNIQC DFANFLSISL LLISYYLL**  ..........
```

*Fig. 4*

48 KDa G1 i-antigen repeats

```
SEQ ID NO:         10              20              30              40              50              60              70              80              90
      8    CPDFTQTQAS LTTMVGAADLG TCVNCRPNFY YNGGAAQGEA NGNOPFAANN           CVPCQLNFRV GSVTVAGDIA  TLATQCST Q
      9    CPTGTALDDG VTLVEDIGAA QCVKCKPNFY YNGGSPQGEA FGVQMFAAGA AAAGVAAVTS QCVPCQLNFN DSPATAGAQA  NLATQCSN Q
     10    CPTGTVTDDG VTLVENTISAT LCVKCRPNFY YNGGSPQGEA FGVQMFAAGA AAAGVAAVTS QCVPCQLNFN DSPATAGAQA  NLATQCST Q
     11    CPTGTAIQDG VTLVFSNSST QCSQCPANYF FNGN----    FPA      GK           S QCLKCPVSFT -TPAFAPGNT -ATATQCIT T
     12    CRATLVIDDG TSTNFVASAT ECIKCSAGFF ASKITG-FTA GTD                    TQTECTKKLT SGATAKVTA EATQKVQCAS T
                 *          *          *                                          *                      *
```

*Fig. 5a*

55 kDa G5 i-antigen repeats

```
SEQ ID NO:
     55  1  CPVGTETNTAGQVDDLGTPANCVNCQKNFYTNNAA----AFMPGASTCTPCPQKKDAGAQPNPPATANLVT--QCNVK
     56  2  CPAGTAIGG--AIDYAAIITECVNCRINFYNENAP----NFNAGASTCTECPVNEVGGALTAGNAATIV--AQCNVA
     57  3  CPIGTALDDGVTTDYVRSFTECVKCRLNFYYNGNGNTPFNPGKSQCTPCPAIKPANVAQATIGNDATITAQCNVA
     58  4  CPDGTIISAAGVNNWVAQN--TECINCAPNFYWNNAP----NFNPGNSTCIPCPANKDYGAEATAGAATLAK--QCNTA
     59  5  CPDGTAIISGATNYVILQ--LTECINCAANFYFDGN----NEQAGSSRCKACPANKVQGAVATAGGTATLI-AQCALE
     60  6  CPAGTVLTDGTTLSTVKQAASECVKCAANFYTTKQ----TDWVAGIDTCTSCNKKLITSGAEANLPESAKKNI-QCDFFA
             *                    *                  *                                    *
```

```
SEQ ID NO: 61  i-ag    20 AVFCPDGTQTQAG-LTDVGAADLGTCVNC-RPNFYYNGGAAQG---EANGNQP-PAANNAAR---GICVP---CQINRVGSVTNAGDLATL
SEQ ID NO: 62  vspA6-S1 61 AVDCQ-----GSAGYYTDDSVSDAKECKCKCNAPCTACAGTADKCTKCDANGAAPYLKKTNPSDPTGTCVSAVDCPG-SAGYYT---DDSVSD
                          ** ::       ::***:******:. *:*  :* : *:*..: .**  ** :  .:** *    .**.. *:*: :: *::      .:

i-ag     ATQCSTQCPTGTALDDGVTDVFDRSAAQCVKCKPN----FYYNGGSPQ-GE------APGVQVFAAGAAAAGVAAVTSQCVEQLNKNDSPA
               vspA6-S1 AKECK-KCAEGQKPNTAGTQCFSCSDANCERCQNDVCARCSTGAPPENGKCPAATPGCHSSCDGCTENAMTNQADRCNCRCKEGRYLKFS
                          :*.  .*. *    .*.*:*. *:: ** .*:*  .**  *   .*       :    . :   :    :   .    *: * i-ag     TAGAQANLATQCSNQCPTGTVLDDGVTLVFNTSATTCVKCRPNFYYNGGSPQGEAPGVQVFAAGAAAAGVAAVTSQCVEQINKNDSPAT
               vspA6-S1 SAAGQSGTCLT-AEECTSDTTH--FTKEKAGDSKGMCLECS-----DATHGIAGCKK---CAL----KTLSGEAESTVCSEC-TDKWLTPS-
                          :*.*: .. *  *: * **    :*:  .*.   * :*.     ** .* ** :   **     .*.*:.*:. ** :*  **:

i-ag     AGAQANLATQCSTQCPTGTAIQDGVTLVFSNSSTQCSQCTANYFPNGNFEAGKSQCLKCPVSKTTPAHAPGNTATQATCCLTTCP---AGT
               vspA6-S1 -G----N---HCLDNCPAGTYPND--NNLCTSCHDT-CBEC-----NGN---ADRAECTPC-----YPGYSLLYGSCTAG/CVEGCTGAPGA
                          *     :   .* ::**:** ::   :.* :*:*  *.**      .*     :.*: *      *  ::  ..* *: *:  *: *.

i-ag     VLDDGTSTNFVASATECTKCSAGPP-------ASKTTGFT---AGTD-ICTECKKLTSGATAKVY--AEATQKVQCASTTPAK 428
               vspA6-S1 NCADGQCTADVGGAKYCRQCKDGYAPIDGICTAVAAAGRTNVCTAADGTPCAGEYT-LMSGGCYGVAKLPGKSVCTLASNGK 459
                          : **:.**::..*:: * *. *   .*    : ::** .   ::*: ** *:   .:*.  :  *: .:..*  :*:..*
```

Fig. 8

| SEQ ID NO: | Primers for synthesis of G5 synthetic gene. |
|---|---|
| 70 | 3201:<br>ATG GGA ATT CAA ATG AAG AAC AAC ATC CTG GTG ATC CTG ATC ATC TCT CTG TTC ATC AAC CAG ATC AAG TCT GCT AAC TGT CCT GTG GGA ACC GAG ACC AAC ACC GCT GGA CAG GTG |
| 71 | 3202:<br>CTC CAG GCA CGA AAG CAG CAG CGT TGT TGT AGT AGA AGT TCT TCT GAC AGT TCA CAC AGT TAG CAG GGG TTC CCA GGT CGT CCA CCT GTC CAG CGG TGT TGG TC |
| 72 | 3203:<br>CGC TGC TGC TTT CGT GCC TGG AGC TTC TAC CTG TAC CCC TTG TCC TCA GAA GAA GGA CGC TGG AGC TCA GCC TAA CCC TCC TGC TAC CGC TAA CCT GGT G |
| 73 | 3204:<br>GAT GAT AGC AGC GTA GTC GGT AGC TCC TCC AGC GAT AGC GGT TCC AGC AGG ACA CTT CAC GTT ACA CTG GGT CAC CAG GTT AGC GGT AGC AGG AG |
| 74 | 3205:<br>GCT ACC GAC TAC GCT GCT ATC ATC ACC GAG TGT GTG AAC TGT CGC ATC AAC TTC TAC AAC GAG AAC GCT CCT AAC TTC AAC GCT GGA GCT TCT ACC TGT ACC GCT TGT CCT GTG AAC CGC GTG GGA GGA GCT CTG ACC |
| 75 | 3206:<br>GGT GAA AGA GCG CAC GTA GTC GGT GGT CAC TCC GTC GTC CAG AGC GGT TCC GGT AGG ACA AGC CAC GTT ACA CTG AGC CAC GAT GGT AGC AGC GTT TCC AGC GGT CAG AGC TCC TCC CAC GCG |
| 76 | 3207:<br>GAC TAC GTG CGC TCT TTC ACC GAG TGT GTG AAG TGT CGC CTG AAC TTC TAC TAC AAC GGA AAC AAC GGA AAC ACC CCT TTC AAC CCT GGA AAG TCT CAG |
| 77 | 3208:<br>GTG ATG GTA GCG TCG TTT CCC AGG GTA GCC TGA GCC ACG TTA GCA GGC TTG ATA GCA GGA CAA GGG GTA CAC TGA GAC TTT CCA GGG TTG AAA GG |
| 78 | 3209:<br>GGG AAA CGA CGC TAC CAT CAC CGC TCA GTG TAA CGT GGC TTG TCC TGA CGG AAC CAT CTC TGC TGC TGG AGT GAA CAA CTG GGT GGC TCA GAA C |
| 79 | 3210:<br>CAG ACA GGT AGA GTT TCC AGG GTT GAA GTT AGG AGC GTT GTT GTT GTA GAA GTT AGG AGC ACA GTT GGT ACA CTC GGT GTT CTG AGC CAC CCA GTT GTT C |
| 80 | 3211:<br>CCC TGG AAA CTC TAC CTG TCT GCC TTG TCC TGC TAA CAA GGA CTA CGG AGC TGA GGC TAC CGC TGG AGG AGC TGC TAC CCT GGC TAA GC |
| 81 | 3212:<br>GGT CTG CAG GAT CAC GTA GTT GGT AGC TCC AGA AGC GAT AGC GGT TCC GTC AGG ACA AGC GAT GTT ACA CTG CTT AGC CAG GGT AGC AGC |
| 82 | 3213:<br>CAA CTA CGT GAT CCT GCA GAC CGA GTG TCT GAA CTG TGC TGC TAA CTT CTA CTT CGA CGG AAA CAA CTT CCA GGC TGG ATC TTC TCG CTG TAA GG |
| 83 | 3214:<br>GAG CGA TCA GGG TAG CGG TTC CTC CAG CGG TAG CCA CAG CTC CCT GCA CCT TGT TAG CAG GAC AAG CCT TAC AGC GAG AAG ATC CAG CCT GG |
| 84 | 3215:<br>GAA CCG CTA CCC TGA TCG CTC AGT GTG CTC TGG AGT GTC CTG CTG GAA CCG TGC TGA CCG ACG GAA CCA CCT CTA CCT ACA AGC AGG CTG CTT C |
| 85 | 3216:<br>GGT GTC GAT TCC AGC CAC CCA GTC GGT CTG CTT GGT GGT GTA GAA GTT AGC AGC ACA CTT CAC ACA CTC AGA AGC AGC CTG CTT GTA GGT AG |
| 86 | 3217:<br>GGG TGG CTG GAA TCG ACA CCT GTA CCT CTT GTA ACA AGA AGC TGA CCT CTG GAG CTG AGG CTA ACC TGC CTG AGT CTG CTA AGA AGA ACA TC |
| 87 | 3218:<br>GAG GGA TCC TTA TTA CAG CAG GTA GTA AGA GAT CAG CAG CAG AGA GAT AGA CAG GAA GTT AGC GAA GTC ACA CTG GAT GTT CTT CTT AGC AGA CT |

*Fig. 12*

G5 proline mutant

```
                     10        ↓ 20        30         40         50         60
SEQ ID NO: 53  ATGAAGAACA ACATCCCGGT GATCCTGATC ATCTCTCTGT TCATCAACCA GATCAAGTCT 70         80         90        100        110        120
               GCTAACTGTC CTGTGGGAAC CGAGACCAAC ACCGCTGGAC AGGTGGACGA CCTGGGAACC 130        140        150        160        170        180
               CCTGCTAACT GTGTGAACTG TCAGAAGAAC TTCTACTACA CAACGCTGC TGCTTTCGTG 190        200        210        220        230        240
               CCTGGAGCTT CTACCTGTAC CCCTTGTCCT CAGAAGAAGG ACGCTGGAGC TCAGCCTAAC 250        260        270        280        290        300
               CCTCCTGCTA CCGCTAACCT GGTGACCCAG TGTAACGTGA AGTGTCCTGC TGGAACCGCT 310        320        330        340        350        360
               ATCGCTGGAG GAGCTACCGA CTACGCTGCT ATCATCACCG AGTGTGTGAA CTGTCGCATC 370        380        390        400        410        420
               AACTTCTACA ACGAGAACGC TCCTAACTTC AACGCTGGAG CTTCTACCTG TACCGCTTGT 430        440        450        460        470        480
               CCTGTGAACC GTGTGGGAGG AGCTCTGACC GCTGGAAACG CTGCTACCAT CGTGGCTCAG 490        500        510        520        530        540
               TGTAACGTGG CTTGTCCTAC CGGAACCGCT CTGGACGACG GAGTGACCAC CGACTACGTG 550        560        570        580        590        600
               CGCTCTTTCA CCGAGTGTGT GAAGTGTCGC CTGAACTTCT ACTACAACGG AAACAACGGA 610        620        630        640        650        660
               AACACCCCTT TCAACCCTGG AAAGTCTCAG TGTACCCCTT GTCCTGCTAT CAAGCCTGCT 670        680        690        700        710        720
               AACGTGGCTC AGGCTACCCT GGGAAACGAC GCTACCATCA CCGCTCAGTG TAACGTGGCT 730        740        750        760        770        780
               TGTCCTGACG GAACCATCTC TGCTGCTGGA GTGAACAACT GGGTGGCTCA GAACACCGAG 790        800        810        820        830        840
               TGTACCAACT GTGCTCCTAA CTTCTACAAC AACAACGCTC TAACTTCAA CCCTGGAAAC 850        860        870        880        890        900
               TCTACCTGTC TGCCTTGTCC TGCTAACAAG GACTACGGAG CTGAGGCTAC CGCTGGAGGA 910        920        930        940        950        960
               GCTGCTACCC TGGCTAAGCA GTGTAACATC GCTTGTCCTG ACGGAACCGC TATCGCTTCT 970        980        990       1000       1010       1020
               GGAGCTACCA ACTACGTGAT CCTGCAGACC GAGTGTCTGA ACTGTGCTGC TAACTTCTAC 1030       1040       1050       1060       1070       1080
               TTCGACGGAA ACAACTTCCA GGCTGGATCT TCTCGCTGTA AGGCTTGTCC TGCTAACAAG 1090       1100       1110       1120       1130       1140
               GTGCAGGGAG CTGTGGCTAC CGCTGGAGGA ACCGCTACCC TGATCGCTCA GTGTGCTCTG 1150       1160       1170       1180       1190       1200
               GAGTGTCCTG CTGGAACCGT GCTGACCGAC GGAACCACCT CTACCTACAA GCAGGCTGCT 1210       1220       1230       1240       1250       1260
               TCTGAGTGTG TGAAGTGTGC TGCTAACTTC TACACCACCA AGCAGACCGA CTGGGTGGCT
```

Fig. 13a proline mutant

```
         1270        1280        1290        1300        1310        1320
    GGAATCGACA  CCTGTACCTC  TTGTAACAAG  AAGCTGACCT  CTGGAGCTGA  GGCTAACCTG 1330        1340        1350        1360        1370        1380
    CCTGAGTCTG  CTAAGAAGAA  CATCCAGTGT  GACTTCGCTA  ACTTCCTGTC  TATCTCTCTG 1390        1400        1410        1420        1430        1440
    CTGCTGATCT  CTTACTACCT  GCTG......  ..........  ..........  ..........
```

*Fig. 13b*

G5 proline mutant protein

```
              ↓    10         20         30         40         50         60
SEQ ID NO: 54 MKNNIPVILI ISLFINQIKS ANCPVGTETN TAGQVDDLGT PANCVNCQKN FYYNNAAAFV 70         80         90        100        110        120
              PGASTCTPCP QKKDAGAQPN PPATANLVTQ CNVKCPAGTA IAGGATDYAA IITECVNCRI 130        140        150        160        170        180
              NFYNENAPNF NAGASTCTAC PVNRVGGALT AGNAATIVAQ CNVACPTGTA LDDGVTTDYV 190        200        210        220        230        240
              RSFTECVKCR LNFYYNGNNG NTPFNPGKSQ CTPCPAIKPA NVAQATLGND ATITAQCNVA 250        260        270        280        290        300
              CPDGTISAAG VNNWVAQNTE CTNCAPNFYN NNAPNFNPGN STCLPCPANK DYGAEATAGG 310        320        330        340        350        360
              AATLAKQCNI ACPDGTAIAS GATNYVILQT ECLNCAANFY FDGNNFQAGS SRCKACPANK 370        380        390        400        410        420
              VQGAVATAGG TATLIAQCAL ECPAGTVLTD GTTSTYKQAA SECVKCAANF YTTKQTDWVA 430        440        450        460        470        480
              GIDTCTSCNK KLTSGAEANL PESAKKNIQC DFANFLSISL LLISYYLL.. ..........
```

*Fig. 14*

Serum: anti-live TG1 (1:20)

Serum: anti-live Tneo (1:20) (negative control)

SEQUENCE LISTING

<160> NUMBER OF SEQ ID NOS: 102

<210> SEQ ID NO 1
<211> LENGTH: 1326
<212> TYPE: DNA
<213> ORGANISM: Ichthyophthirius multifiliis

<400> SEQUENCE: 1

| | |
|---|---|
| atgaaatata atattttatt aattttaatt atttctttat ttattaatga attaagagct | 60 |
| gttccatgtc ctgatggtac ttagactcaa gctggattga ctgatgtagg tgctgctgat | 120 |
| cttggtactt gtgttaattg cagacctaat ttttactata atggtggtgc tgcttaagga | 180 |
| gaagctaatg gtaattaacc tttcgcagca ataatgctg ctagaggtat atgtgtacca | 240 |
| tgccaaataa acagagtagg ctctgttacc aatgcaggtg acttagctac tttagccaca | 300 |
| taatgcagta cttaatgtcc tactggcact gcacttgatg atggagtgac agatgttttt | 360 |
| gatagatcag ccgcataatg tgttaaatgc aaacctaact tttactataa tggtggttct | 420 |
| ccttaaggtg aagctcctgg cgtttaagtt tttgctgctg gtgctgccgc tgcaggtgtt | 480 |
| gctgccgtta ctagttaatg tgtaccttgc aactaaaca aaaacgattc tcctgccact | 540 |
| gcaggtgcct aagctaattt agccacataa tgtagcaatt aatgtcctac tggcactgta | 600 |
| cttgatgatg gagtgacact tgttttaat acatcagcca cattatgtgt aaatgcaga | 660 |
| cctaactttt actataatgg tggttctcct taaggtgaag ctcctggcgt ttaagttttt | 720 |
| gctgctggtg ctgccgctgc aggtgttgct gccgttacta gttaatgtgt accttgccaa | 780 |
| ataaacaaaa acgattctcc tgccactgca ggtgcctaag ctaatttagc cacataatgc | 840 |
| agtacttaat gtccaactgg cactgcaatt caagacggag tgacacttgt ttttagtaat | 900 |
| tcatccacat aatgttctta atgcattgct aattactttt ttaatggtaa tttcgaagca | 960 |
| ggtaaaagtt aatgtttaaa gtgtccagta agtaaaacta ctccagcaca tgctccaggt | 1020 |
| aatactgcta cttaagccac ataatgtttg accacatgtc ctgctggtac agtacttgat | 1080 |
| gatggaacat caactaattt tgtagcttcc gcaactgaat gtactaaatg ttctgctggc | 1140 |
| tttttttgcat caaaaacaac tggttttaca gcaggtactg atacatgtac tgaatgtact | 1200 |
| aaaaaattaa cttctggtgc cacagctaaa gtatatgctg aagctactca aaaagtataa | 1260 |
| tgcgcctcca ctactttcgc taaattttta tcgatttcct tattatttat ttctttctat | 1320 |
| ttattg | 1326 |

<210> SEQ ID NO 2
<211> LENGTH: 2486
<212> TYPE: DNA
<213> ORGANISM: Ichthyophthirius multifiliis

<400> SEQUENCE: 2

| | |
|---|---|
| aaattaaaaa atgttttat ttaataatat tttttcacgt gtaattatta ttattttttt | 60 |
| tttaaataaa ttataaaaaa taaaaagtag aaaaatatcc ataataaaat ataaaataaa | 120 |
| tttaaaaatt atttatgatt tgttttaga aataaggtt ttatttataa taatgaattc | 180 |
| ttaaaataat gaatcgatat tatataaatt tttatttttt ataaaatatt gaattaccta | 240 |
| aaataatata aatttatgaa atattattta aaataataag ttatagaata aatttatttt | 300 |
| tatttctaat ttttttata attattaaaa aaaaaaaaa aatctattac tattttgcat | 360 |
| ttacaaacga tagaaaaaac taaaatttat aatattatta aaaaaaaaaa tataaataat | 420 |
| aataataaaa atatgaaata taatattta ttaattttaa ttatttcttt atttattaat | 480 |
| gaattaagag ctgttccatg tcctgatggt acttagactc aagctggatt gactgatgta | 540 |
| ggtgctgctg atcttggtac ttgtgttaat tgcagaccta atttttacta atggtggt | 600 |
| gctgcttaag gagaagctaa tggtaattaa cctttcgcag caaataatgc tgctagaggt | 660 |
| atatgtgtac catgccaaat aaacagagta ggctctgtta ccaatgcagg tgacttagct | 720 |
| actttagcca cataatgcag tacttaatgt cctactggca ctgcacttga tgatggagtg | 780 |

-continued

| | |
|---|---|
| acagatgttt tgatagatc agccgcataa tgtgttaaat gcaaacctaa cttttactat | 840 |
| aatggtggtt ctccttaagg tgaagctcct ggcgtttaag ttttttgctgc tggtgctgcc | 900 |
| gctgcaggtg ttgctgccgt tactagttaa tgtgtacctt gccaactaaa caaaaacgat | 960 |
| tctcctgcca ctgcaggtgc ctaagctaat ttagccacat aatgtagcaa ttaatgtcct | 1020 |
| actggcactg tacttgatga tggagtgaca cttgttttta atacatcagc cacattatgt | 1080 |
| gttaaatgca gacctaactt ttactataat ggtggttctc cttaaggtga agctcctggc | 1140 |
| gtttaagttt ttgctgctgg tgctgccgct gcaggtgttg ctgccgttac tagttaatgt | 1200 |
| gtaccttgcc aaataaacaa aaacgattct cctgccactg caggtgccta agctaattta | 1260 |
| gccacataat gcagtactta atgtccaact ggcactgcaa ttcaagacgg agtgacactt | 1320 |
| gttttttagta attcatccac ataatgttct taatgcattg ctaattactt ttttaatggt | 1380 |
| aatttcgaag caggtaaaag ttaatgttta aagtgtccag taagtaaaac tactccagca | 1440 |
| catgctccag gtaatactgc tacttaagcc acataatgtt tgaccacatg tcctgctggt | 1500 |
| acagtacttg atgatggaac atcaactaat tttgtagctt ccgcaactga atgtactaaa | 1560 |
| tgttctgctg gcttttttgc atcaaaaaca actggtttta cagcaggtac tgatacatgt | 1620 |
| actgaatgta ctaaaaaatt aacttctggt gccacagcta agtatatgc tgaagctact | 1680 |
| caaaaagtat aatgcgcctc cactactttc gctaaatttt tatcgatttc cttattattt | 1740 |
| atttcttttct atttattgtg atgaataaaa taattcatat tatttttattt ttttatttta | 1800 |
| tgtttataaa ttaaaaaata gataaaattt aaaatatatt aaaaataatt ttttatataa | 1860 |
| attatcaatt aacaactaac taacaaaata caattaaaat cttttatagaa ggttttttctt | 1920 |
| tataatattt taaggattaa tttacaaatt ttaattaaag taacattttta tcatttaaaa | 1980 |
| tcttattaaa ataaatacat aaattctagt tgattcttttt ttaatattaa tttaaaatta | 2040 |
| gaataaaaaa atatgtttta agtaaataaa agaagaaatt taatttaatt tatttatatt | 2100 |
| taatttaata tttatttaat ttattttcga atatttattt atcaaacttt taaaactaaa | 2160 |
| aatttattaa gtctaattta aactatatat attatattat tttgtattct ttttttttatt | 2220 |
| cataatcata aatacagaat ttttttatatt ttgagttgtg catattattt tatgaatgtt | 2280 |
| atcacttata tatgcgtatg taattttattg tatctcattc agggcttaag cttgtaaaat | 2340 |
| aataatattc aatatatttg ttaagggaaa ggttaggcaa actaaactaa attttttaac | 2400 |
| aaaaatatat caattacaaa aatatttatt tataaatgaa tgaataaaaa tagtattttt | 2460 |
| atttatttat aacactaaaa gaattc | 2486 |

<210> SEQ ID NO 3
<211> LENGTH: 1404
<212> TYPE: DNA
<213> ORGANISM: Ichthyophthirius multifiliis

<400> SEQUENCE: 3

| | |
|---|---|
| atgaaaaata atattttagt aatattgatt atttcattat ttatcaatta aattaaatct | 60 |
| gctaattgtc ctgttggaac tgaaactaac acagccggat aagttgatga tctaggaact | 120 |
| cctgcaaatt gtgttaattg ttagaaaaac ttttattata ataatgctgc tgctttcgtt | 180 |
| cctggtgcta gtacgtgtac accttgtcca taaaaaaaag atgctggtgc ttaaccaaat | 240 |
| ccacctgcta ctgctaattt agtcacataa tgtaacgtta aatgccctgc tggtaccgca | 300 |
| attgcaggtg gagcaacaga ttatgcagca ataatcacag aatgtgttaa ttgtagaatt | 360 |

```
aatttttata atgaaaatgc tccaaatttt aatgcaggtg ctagtacatg cacagcttgt      420
ccggtaaaca gagttggtgg tgcattgact gctggtaatg ccgctaccat agtcgcataa      480
tgtaacgtcg catgtcctac tggtactgca cttgatgatg gagtaactac tgattatgtt      540
agatcattca cagaatgtgt taaatgtaga cttaactttt actataatgg taataatggt      600
aatactcctt tcaatccagg taaaagttaa tgcacacctt gtccggcaat taaacctgct      660
aatgttgctt aagctacttt aggtaatgat gctacaataa ccgcataatg taacgttgca      720
tgccctgatg gtactataag tgctgctgga gtaaataatt gggtagcaca aaacactgaa      780
tgtactaatt gtgctcctaa cttttacaat aataatgctc ctaatttcaa tccaggtaat      840
agtacatgcc taccttgccc agcaaataaa gattatggtg ctgaagccac tgcaggtggt      900
gccgctactt tagccaaata atgtaatatt gcatgccctg atggtactgc aattgctagt      960
ggagcaacta attatgtaat attataaaca gaatgtctaa attgtgctgc taacttttat     1020
tttgatggta ataatttcta ggcaggaagt agtagatgca aagcatgtcc agcaaataaa     1080
gtttaaggcg ctgtagcaac tgcaggtggt actgctactt taattgcata atgtgcccttt    1140 gaatgccctg ctggtactgt actcaccgat ggaacaacat ctactataa ataagcagca     1200 tctgaatgtg ttaaatgtgc tgccaacttt tatactacaa ataaactga ttgggtagca     1260 ggtattgata catgtactag ttgtaataaa aaattaactt ctggcgctga agctaattta     1320
cctgaatctg ctaaaaaaaa tatataatgt gatttcgcta atttttatc aatttcctta     1380 ttattgattt cttattattt atta                                            1404

<210> SEQ ID NO 4
<211> LENGTH: 100
<212> TYPE: DNA
<213> ORGANISM: Ichthyophthirius multifiliis

<400> SEQUENCE: 4
taaagtatat gctgaagcta ctcaaaaagt ataatgcgcc tccactactt tcgctaaatt      60
tttatcgatt tccttattat ttatttcttt ctatttattg                           100

<210> SEQ ID NO 5
<211> LENGTH: 1404
<212> TYPE: DNA
<213> ORGANISM: Artificial Sequence
<220> FEATURE:
<223> OTHER INFORMATION: Description of Artificial Sequence:  synthetic
      55kD i-antigen coding region

<400> SEQUENCE: 5
atgaagaaca acatcctggt gatcctgatc atctctctgt tcatcaacca gatcaagtct       60
gctaactgtc ctgtgggaac cgagaccaac accgctggac aggtggacga cctgggaacc      120
cctgctaact gtgtgaactg tcagaagaac ttctactaca caacgctgc tgctttcgtg       180 cctggagctt ctacctgtac cccttgtcct cagaagaagg acgctggagc tcagcctaac      240
cctcctgcta ccgctaacct ggtgacccag tgtaacgtga agtgtcctgc tggaaccgct      300
atcgctggag gagctaccga ctacgctgct atcatcaccg agtgtgtgaa ctgtcgcatc      360
aacttctaca acgagaacgc tcctaacttc aacgctggag cttctacctg taccgcttgt      420
cctgtgaacc gcgtgggagg agctctgacc gctggaaacg ctgctaccat cgtggctcag      480
tgtaacgtgg cttgtcctac cggaaccgct ctggacgacg gagtgaccac cgactacgtg      540
cgctctttca ccgagtgtgt gaagtgtcgc ctgaacttct actacaacgg aaacaacgga      600
```

```
aacaccccctt tcaaccctgg aaagtctcag tgtaccccctt gtcctgctat caagcctgct    660
aacgtggctc aggctaccct gggaaacgac gctaccatca ccgctcagtg taacgtggct    720
tgtcctgacg gaaccatctc tgctgctgga gtgaacaact gggtggctca gaacaccgag    780
tgtaccaact gtgctcctaa cttctacaac aacaacgctc taacttcaa ccctggaaac    840 tctacctgtc tgccttgtcc tgctaacaag gactacggag ctgaggctac cgctggagga    900
gctgctaccc tggctaagca gtgtaacatc gcttgtcctg acggaaccgc tatcgcttct    960
ggagctacca actacgtgat cctgcagacc gagtgtctga actgtgctgc taacttctac   1020
ttcgacggaa caacttcca ggctggatct tctcgctgta aggcttgtcc tgctaacaag   1080
gtgcagggag ctgtggctac cgctggagga accgctaccc tgatcgctca gtgtgctctg   1140
gagtgtcctg ctggaaccgt gctgaccgac ggaaccacct ctacctacaa gcaggctgct   1200
tctgagtgtg tgaagtgtgc tgctaacttc tacaccacca gcagaccga ctgggtggct   1260 ggaatcgaca cctgtacctc ttgtaacaag aagctgacct ctggagctga ggctaacctg   1320
cctgagtctg ctaagaagaa catccagtgt gacttcgcta acttcctgtc tatctctctg   1380
ctgctgatct cttactacct gctg                                          1404

<210> SEQ ID NO 6
<211> LENGTH: 442
<212> TYPE: PRT
<213> ORGANISM: Ichthyophthirius multifiliis

<400> SEQUENCE: 6

Met Lys Tyr Asn Ile Leu Leu Ile Leu Ile Ile Ser Leu Phe Ile Asn
 1               5                  10                  15

Glu Leu Arg Ala Val Pro Cys Pro Asp Gly Thr Gln Thr Gln Ala Gly
             20                  25                  30

Leu Thr Asp Val Gly Ala Ala Asp Leu Gly Thr Cys Val Asn Cys Arg
         35                  40                  45

Pro Asn Phe Tyr Tyr Asn Gly Gly Ala Ala Gln Gly Glu Ala Asn Gly
     50                  55                  60

Asn Gln Pro Phe Ala Ala Asn Asn Ala Ala Arg Gly Ile Cys Val Pro
 65                  70                  75                  80

Cys Gln Ile Asn Arg Val Gly Ser Val Thr Asn Ala Gly Asp Leu Ala
                 85                  90                  95

Thr Leu Ala Thr Gln Cys Ser Thr Gln Cys Pro Thr Gly Thr Ala Leu
            100                 105                 110

Asp Asp Gly Val Thr Asp Val Phe Asp Arg Ser Ala Ala Gln Cys Val
        115                 120                 125

Lys Cys Lys Pro Asn Phe Tyr Tyr Asn Gly Gly Ser Pro Gln Gly Glu
    130                 135                 140

Ala Pro Gly Val Gln Val Phe Ala Ala Gly Ala Ala Ala Gly Val
145                 150                 155                 160

Ala Ala Val Thr Ser Gln Cys Val Pro Cys Gln Leu Asn Lys Asn Asp
                165                 170                 175

Ser Pro Ala Thr Ala Gly Ala Gln Asn Leu Ala Thr Gln Cys Ser
            180                 185                 190

Asn Gln Cys Pro Thr Gly Thr Val Leu Asp Asp Gly Val Thr Leu Val
        195                 200                 205

Phe Asn Thr Ser Ala Thr Leu Cys Val Lys Cys Arg Pro Asn Phe Tyr
    210                 215                 220

Tyr Asn Gly Gly Ser Pro Gln Gly Glu Ala Pro Gly Val Gln Val Phe
```

```
                225                 230                 235                 240
Ala Ala Gly Ala Ala Ala Gly Val Ala Val Thr Ser Gln Cys
            245                 250                 255
Val Pro Cys Gln Ile Asn Lys Asn Asp Ser Pro Ala Thr Ala Gly Ala
            260                 265                 270
Gln Ala Asn Leu Ala Thr Gln Cys Ser Thr Gln Cys Pro Thr Gly Thr
            275                 280                 285
Ala Ile Gln Asp Gly Val Thr Leu Val Phe Ser Asn Ser Ser Thr Gln
            290                 295                 300
Cys Ser Gln Cys Ile Ala Asn Tyr Phe Phe Asn Gly Asn Phe Glu Ala
305                 310                 315                 320
Gly Lys Ser Gln Cys Leu Lys Cys Pro Val Ser Lys Thr Thr Pro Ala
            325                 330                 335
His Ala Pro Gly Asn Thr Ala Thr Gln Ala Thr Gln Cys Leu Thr Thr
            340                 345                 350
Cys Pro Ala Gly Thr Val Leu Asp Asp Gly Thr Ser Thr Asn Phe Val
            355                 360                 365
Ala Ser Ala Thr Glu Cys Thr Lys Cys Ser Ala Gly Phe Phe Ala Ser
370                 375                 380
Lys Thr Thr Gly Phe Thr Ala Gly Thr Asp Thr Cys Thr Glu Cys Thr
385                 390                 395                 400
Lys Lys Leu Thr Ser Gly Ala Thr Ala Lys Val Tyr Ala Glu Ala Thr
            405                 410                 415
Gln Lys Val Gln Cys Ala Ser Thr Thr Phe Ala Lys Phe Leu Ser Ile
            420                 425                 430
Ser Leu Leu Phe Ile Ser Phe Tyr Leu Leu
            435                 440
```

<210> SEQ ID NO 7
<211> LENGTH: 468
<212> TYPE: PRT
<213> ORGANISM: Ichthyophthirius multifiliis

<400> SEQUENCE: 7

```
Met Lys Asn Asn Ile Leu Val Ile Leu Ile Ser Leu Phe Ile Asn
1               5                   10                  15
Gln Ile Lys Ser Ala Asn Cys Pro Val Gly Thr Glu Thr Asn Thr Ala
            20                  25                  30
Gly Gln Val Asp Asp Leu Gly Thr Pro Ala Asn Cys Val Asn Cys Gln
            35                  40                  45
Lys Asn Phe Tyr Tyr Asn Asn Ala Ala Ala Phe Val Pro Gly Ala Ser
        50                  55                  60
Thr Cys Thr Pro Cys Pro Gln Lys Lys Asp Ala Gly Ala Gln Pro Asn
65                  70                  75                  80
Pro Pro Ala Thr Ala Asn Leu Val Thr Gln Cys Asn Val Lys Cys Pro
                85                  90                  95
Ala Gly Thr Ala Ile Ala Gly Gly Ala Thr Asp Tyr Ala Ala Ile Ile
            100                 105                 110
Thr Glu Cys Val Asn Cys Arg Ile Asn Phe Tyr Asn Glu Asn Ala Pro
            115                 120                 125
Asn Phe Asn Ala Gly Ala Ser Thr Cys Thr Ala Cys Pro Val Asn Arg
        130                 135                 140
Val Gly Gly Ala Leu Thr Ala Gly Asn Ala Ala Thr Ile Val Ala Gln
145                 150                 155                 160
```

```
Cys Asn Val Ala Cys Pro Thr Gly Thr Ala Leu Asp Asp Gly Val Thr
                165                 170                 175
Thr Asp Tyr Val Arg Ser Phe Thr Glu Cys Val Lys Cys Arg Leu Asn
            180                 185                 190
Phe Tyr Tyr Asn Gly Asn Asn Gly Asn Thr Pro Phe Asn Pro Gly Lys
        195                 200                 205
Ser Gln Cys Thr Pro Cys Pro Ala Ile Lys Pro Ala Asn Val Ala Gln
    210                 215                 220
Ala Thr Leu Gly Asn Asp Ala Thr Ile Thr Ala Gln Cys Asn Val Ala
225                 230                 235                 240
Cys Pro Asp Gly Thr Ile Ser Ala Ala Gly Val Asn Asn Trp Val Ala
                245                 250                 255
Gln Asn Thr Glu Cys Thr Asn Cys Ala Pro Asn Phe Tyr Asn Asn Asn
            260                 265                 270
Ala Pro Asn Phe Asn Pro Gly Asn Ser Thr Cys Leu Pro Cys Pro Ala
        275                 280                 285
Asn Lys Asp Tyr Gly Ala Glu Ala Thr Ala Gly Gly Ala Ala Thr Leu
    290                 295                 300
Ala Lys Gln Cys Asn Ile Ala Cys Pro Asp Gly Thr Ala Ile Ala Ser
305                 310                 315                 320
Gly Ala Thr Asn Tyr Val Ile Leu Gln Thr Glu Cys Leu Asn Cys Ala
                325                 330                 335
Ala Asn Phe Tyr Phe Asp Gly Asn Asn Phe Gln Ala Gly Ser Ser Arg
            340                 345                 350
Cys Lys Ala Cys Pro Ala Asn Lys Val Gln Gly Ala Val Ala Thr Ala
        355                 360                 365
Gly Gly Thr Ala Thr Leu Ile Ala Gln Cys Ala Leu Glu Cys Pro Ala
370                 375                 380
Gly Thr Val Leu Thr Asp Gly Thr Thr Ser Thr Tyr Lys Gln Ala Ala
                385                 390                 395                 400
Ser Glu Cys Val Lys Cys Ala Ala Asn Phe Tyr Thr Thr Lys Gln Thr
            405                 410                 415
Asp Trp Val Ala Gly Ile Asp Thr Cys Thr Ser Cys Asn Lys Lys Leu
        420                 425                 430
Thr Ser Gly Ala Glu Ala Asn Leu Pro Glu Ser Ala Lys Lys Asn Ile
    435                 440                 445
Gln Cys Asp Phe Ala Asn Phe Leu Ser Ile Ser Leu Leu Leu Ile Ser
450                 455                 460
Tyr Tyr Leu Leu
465

<210> SEQ ID NO 8
<211> LENGTH: 83
<212> TYPE: PRT
<213> ORGANISM: Ichthyophthirius multifiliis

<400> SEQUENCE: 8

Cys Pro Asp Gly Thr Gln Thr Gln Ala Gly Leu Thr Asp Val Gly Ala
 1               5                  10                  15
Ala Asp Leu Gly Thr Cys Val Asn Cys Arg Pro Asn Phe Tyr Tyr Asn
            20                  25                  30
Gly Gly Ala Ala Gln Gly Glu Ala Asn Gly Asn Gln Pro Phe Ala Ala
        35                  40                  45
Asn Asn Ala Ala Arg Gly Ile Cys Val Pro Cys Gln Ile Asn Arg Val
    50                  55                  60
```

-continued

Gly Ser Val Thr Asn Ala Gly Asp Leu Ala Thr Leu Ala Thr Gln Cys
65                  70                  75                  80

Ser Thr Gln

<210> SEQ ID NO 9
<211> LENGTH: 89
<212> TYPE: PRT
<213> ORGANISM: Ichthyophthirius multifiliis

<400> SEQUENCE: 9

Cys Pro Thr Gly Thr Ala Leu Asp Asp Gly Val Thr Asp Val Phe Asp
1               5                   10                  15

Arg Ser Ala Ala Gln Cys Val Lys Cys Lys Pro Asn Phe Tyr Tyr Asn
            20                  25                  30

Gly Gly Ser Pro Gln Gly Glu Ala Pro Gly Val Gln Val Phe Ala Ala
        35                  40                  45

Gly Ala Ala Ala Gly Val Ala Ala Val Thr Ser Gln Cys Val Pro
    50                  55                  60

Cys Gln Leu Asn Lys Asn Asp Ser Pro Ala Thr Ala Gly Ala Gln Ala
65                  70                  75                  80

Asn Leu Ala Thr Gln Cys Ser Asn Gln
                85

<210> SEQ ID NO 10
<211> LENGTH: 89
<212> TYPE: PRT
<213> ORGANISM: Ichthyophthirius multifiliis

<400> SEQUENCE: 10

Cys Pro Thr Gly Thr Val Leu Asp Asp Gly Val Thr Leu Val Phe Asn
1               5                   10                  15

Thr Ser Ala Thr Leu Cys Val Lys Cys Arg Pro Asn Phe Tyr Tyr Asn
            20                  25                  30

Gly Gly Ser Pro Gln Gly Glu Ala Pro Gly Val Gln Val Phe Ala Ala
        35                  40                  45

Gly Ala Ala Ala Gly Val Ala Ala Val Thr Ser Gln Cys Val Pro
    50                  55                  60

Cys Gln Ile Asn Lys Asn Asp Ser Pro Ala Thr Ala Gly Ala Gln Ala
65                  70                  75                  80

Asn Leu Ala Thr Gln Cys Ser Thr Gln
                85

<210> SEQ ID NO 11
<211> LENGTH: 69
<212> TYPE: PRT
<213> ORGANISM: Ichthyophthirius multifiliis

<400> SEQUENCE: 11

Cys Pro Thr Gly Thr Ala Ile Gln Asp Gly Val Thr Leu Val Phe Ser
1               5                   10                  15

Asn Ser Ser Thr Gln Cys Ser Gln Cys Ile Ala Asn Tyr Phe Phe Asn
            20                  25                  30

Gly Asn Phe Glu Ala Gly Lys Ser Gln Cys Leu Lys Cys Pro Val Ser
        35                  40                  45

Lys Thr Thr Pro Ala His Ala Pro Gly Asn Thr Ala Thr Gln Ala Thr
    50                  55                  60

Gln Cys Leu Thr Thr

<210> SEQ ID NO 12
<211> LENGTH: 72
<212> TYPE: PRT
<213> ORGANISM: Ichthyophthirius multifiliis

<400> SEQUENCE: 12

Cys Pro Ala Gly Thr Val Leu Asp Asp Gly Thr Ser Thr Asn Phe Val
 1               5                  10                  15

Ala Ser Ala Thr Glu Cys Thr Lys Cys Ser Ala Gly Phe Phe Ala Ser
            20                  25                  30

Lys Thr Thr Gly Phe Thr Ala Gly Thr Asp Thr Cys Thr Glu Cys Thr
        35                  40                  45

Lys Lys Leu Thr Ser Gly Ala Thr Ala Lys Val Tyr Ala Glu Ala Thr
    50                  55                  60

Gln Lys Val Gln Cys Ala Ser Thr
65                  70

<210> SEQ ID NO 13
<211> LENGTH: 14
<212> TYPE: PRT
<213> ORGANISM: Ichthyophthirius multifiliis

<400> SEQUENCE: 13

Phe Leu Ser Ile Ser Leu Leu Phe Ile Ser Phe Tyr Leu Leu
 1               5                  10

<210> SEQ ID NO 14
<211> LENGTH: 23
<212> TYPE: PRT
<213> ORGANISM: Ichthyophthirius multifiliis

<400> SEQUENCE: 14

Gln Cys Ala Ser Thr Thr Phe Ala Lys Phe Leu Ser Ile Ser Leu Leu
 1               5                  10                  15

Phe Ile Ser Phe Tyr Leu Leu
            20

<210> SEQ ID NO 15
<211> LENGTH: 20
<212> TYPE: PRT
<213> ORGANISM: Ichthyophthirius multifiliis

<400> SEQUENCE: 15

Met Lys Asn Asn Ile Leu Val Ile Leu Ile Ile Ser Leu Phe Ile Asn
 1               5                  10                  15

Gln Ile Lys Ser
            20

<210> SEQ ID NO 16
<211> LENGTH: 14
<212> TYPE: PRT
<213> ORGANISM: Ichthyophthirius multifiliis

<400> SEQUENCE: 16

Phe Leu Ser Ile Ser Leu Leu Leu Ile Ser Tyr Tyr Leu Leu
 1               5                  10

<210> SEQ ID NO 17
<211> LENGTH: 20
<212> TYPE: PRT

-continued

<213> ORGANISM: Ichthyophthirius multifiliis

<400> SEQUENCE: 17

Gln Cys Asp Phe Ala Asn Phe Leu Ser Ile Ser Leu Leu Ile Ser
 1               5                  10                  15

Tyr Tyr Leu Leu
            20

<210> SEQ ID NO 18
<211> LENGTH: 33
<212> TYPE: PRT
<213> ORGANISM: Ichthyophthirius multifiliis

<400> SEQUENCE: 18

Lys Val Tyr Ala Glu Ala Thr Gln Lys Val Gln Cys Ala Ser Thr Thr
 1               5                  10                  15

Phe Ala Lys Phe Leu Ser Ile Ser Leu Leu Phe Ile Ser Phe Tyr Leu
            20                  25                  30

Leu

<210> SEQ ID NO 19
<211> LENGTH: 60
<212> TYPE: DNA
<213> ORGANISM: Ichthyophthirius multifiliis

<400> SEQUENCE: 19
atgaaaaata atattttagt aatattgatt atttcattat ttatcaatta aattaaatct     60

<210> SEQ ID NO 20
<211> LENGTH: 60
<212> TYPE: DNA
<213> ORGANISM: Ichthyophthirius multifiliis

<400> SEQUENCE: 20
taatgtgatt tcgctaattt tttatcaatt tccttattat tgatttctta ttatttatta     60

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: antisense
      primer

<400> SEQUENCE: 21
agcagcacct acatcagtca atcc                                            24

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: universal
      primer

<400> SEQUENCE: 22
gtaaaacgac ggccagt                                                    17

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: EPBdT18

```
                                  primer

<400> SEQUENCE: 23
gcgaattctg caggatccaa acttttttt ttttttttt                             40

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence:  forward
      primer

<400> SEQUENCE: 24
gtgtcgacag caggtactga tacatg                                          26

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:  forward
      primer

<400> SEQUENCE: 25
cgaaaacagt ggtggtagta cctt                                            24

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:  reverse
      primer

<400> SEQUENCE: 26
gcgaattctg caggatccaa ac                                              22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 27
agcagcacca acatcagtca aacc                                            24

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:  forward
      primer

<400> SEQUENCE: 28
atggtaatta acctttcgca gcaaataa                                        28

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:  reverse
      primer
```

<400> SEQUENCE: 29
ggtctgcatt taacacataa                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: reverse
      primer

<400> SEQUENCE: 30
agatacatca gtatacgaaa                                                    20

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: primary
      structure motif
<221> NAME/KEY: UNSURE
<222> LOCATION: (2)..(3)
<223> OTHER INFORMATION: amino acid

<400> SEQUENCE: 31

Cys Xaa Xaa Cys
  1

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: primary
      structure motif
<221> NAME/KEY: UNSURE
<222> LOCATION: (2)..(4)
<223> OTHER INFORMATION: amino acid

<400> SEQUENCE: 32

Cys Xaa Xaa Xaa Cys
  1               5

<210> SEQ ID NO 33
<211> LENGTH: 53
<212> TYPE: PRT
<213> ORGANISM: Artificial Sequence
<220> FEATURE:
<223> OTHER INFORMATION: Description of Artificial Sequence: repeating
      primary structure motif
<221> NAME/KEY: UNSURE
<222> LOCATION: (2)..(3)
<223> OTHER INFORMATION: amino acid
<221> NAME/KEY: UNSURE
<222> LOCATION: (5)..(24)
<223> OTHER INFORMATION: amino acid
<221> NAME/KEY: UNSURE
<222> LOCATION: (26)..(28)
<223> OTHER INFORMATION: amino acid
<221> NAME/KEY: UNSURE
<222> LOCATION: (30)..(49)
<223> OTHER INFORMATION: amino acid
<221> NAME/KEY: UNSURE
<222> LOCATION: (51)..(52)
<223> OTHER INFORMATION: amino acid

<400> SEQUENCE: 33

Cys Xaa Xaa Cys Xaa Xaa Xaa Xaa Xaa Xaa Xaa Xaa Xaa Xaa Xaa Xaa

-continued

```
              1               5              10              15
Xaa Xaa Xaa Xaa Xaa Xaa Xaa Xaa Cys Xaa Xaa Xaa Cys Xaa Xaa Xaa
             20              25              30
Xaa Xaa Xaa Xaa Xaa Xaa Xaa Xaa Xaa Xaa Xaa Xaa Xaa Xaa Xaa
         35              40              45
Xaa Cys Xaa Xaa Cys
     50
```

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: i-antigen
      P-loop domain
<221> NAME/KEY: UNSURE
<222> LOCATION: (2)..(5)

<400> SEQUENCE: 34

```
Gly Xaa Xaa Xaa Xaa Gly Lys Ser
  1               5
```

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: sense
      primer

<400> SEQUENCE: 35
atgaaataya ayattttatt aatt                                          24

<210> SEQ ID NO 36
<211> LENGTH: 8
<212> TYPE: PRT
<213> ORGANISM: Ichthyophthirius multifiliis

<400> SEQUENCE: 36

```
Met Lys Tyr Asn Ile Leu Leu Thr
  1               5
```

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: antisense
      primer

<400> SEQUENCE: 37
aaataataar gaaatmgata aaaa                                          24

<210> SEQ ID NO 38
<211> LENGTH: 8
<212> TYPE: PRT
<213> ORGANISM: Ichthyophthirius multifiliis

<400> SEQUENCE: 38

```
Phe Leu Ser Ile Ser Leu Leu Phe
  1               5
```

<210> SEQ ID NO 39
<211> LENGTH: 26
<212> TYPE: DNA

```
<213> ORGANISM: Artificial Sequence
<220> FEATURE:
<223> OTHER INFORMATION: Description of Artificial Sequence: antisense
      primer

<400> SEQUENCE: 39
tgctcgagaa tctgttgctc cacctg                                          26

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence: forward
      primer

<400> SEQUENCE: 40
ccagtgagca gagtgacgag gactcgagct caagccccccc cccccccccc cc            52

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: forward
      primer

<400> SEQUENCE: 41
gaggactcga gctcaagc                                                   18

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: reverse
      primer

<400> SEQUENCE: 42
aactcgagta ccagcagggc atttaac                                         27

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 43
cacaccttgt ccggcaatta aac                                             23

<210> SEQ ID NO 44
<211> LENGTH: 1410
<212> TYPE: DNA
<213> ORGANISM: Ichthyophthirius multifiliis

<400> SEQUENCE: 44
atgaaaaata atattttagt aatattgatt atttcattat ttatcaatta aattaaatct     60
gctaattgtc ctgttggaac tgaaactaac acagccggat aagttgatga tctaggaact    120
cctgcaaatt gtgttaattg ttagaaaaac ttttattata ataatgctgc tgctttcgtt    180
cctggtgcta gtacgtgtac accttgtcca taaaaaaaag atgctggtgc ttaaccaaat    240
ccacctgcta ctgctaattt agtcacataa tgtaacgtta aatgcccgtgc tggtaccgca    300 attgcaggtg gagcaacaga ttatgcagca ataatcacag aatgtgttaa ttgtagaatt    360
```

-continued

```
aatttttata atgaaaatgc tccaaatttt aatgcaggtg ctagtacatg cacagcttgt      420
ccggtaaaca gagttggtgg tgcattgact gctggtaatg ccgctaccat agtcgcataa      480
tgtaacgtcg catgtcctac tggtactgca cttgatgatg gagtaactac tgattatgtt      540
agatcattca cagaatgtgt taaatgtaga cttaactttt actataatgg taataatggt      600
aatactcctt tcaatccagg taaaagttaa tgcacacctt gtccggcaat taaacctgct      660
aatgttgctt aagctacttt aggtaatgat gctacaataa ccgcataatg taacgttgca      720
tgccctgatg gtactataag tgctgctgga gtaaataatt gggtagcaca aaacactgaa      780
tgtactaatt gtgctcctaa cttttacaat aataatgctc ctaatttcaa tccaggtaat      840 agtcatgcc taccttgccc agcaaataaa gattatggtg ctgaagccac tgcaggtggt       900
gccgctactt tagccaaata atgtaatatt gcatgccctg atggtactgc aattgctagt      960
ggagcaacta attatgtaat attataaaca gaatgtctaa attgtgctgc taactttat    1020 tttgatggta ataatttcta ggcaggaagt agtagatgca aagcatgtcc agcaaataaa    1080
gtttaaggcg ctgtagcaac tgcaggtggt actgctactt taattgcata atgtgccctt    1140
gaatgccctg ctggtactgt actcaccgat ggaacaacat ctacttataa ataagcagca    1200
tctgaatgtg ttaaatgtgc tgccaacttt tatactacaa aataaactga ttgggtagca    1260
ggtattgata catgtactag ttgtaataaa aaattaactt ctggcgctga agctaattta    1320
cctgaatctg ctaaaaaaaa tatataatgt gatttcgcta attttttatc aatttccta     1380 ttattgattt cttattattt attatgatga                                     1410
```

<210> SEQ ID NO 45
<211> LENGTH: 33
<212> TYPE: DNA
<213> ORGANISM: Artificial Sequence
<220> FEATURE:
<223> OTHER INFORMATION: Description of Artificial Sequence: forward
      primer

<400> SEQUENCE: 45
ccgaattctc tggyactgca cttgatgatg gag                                  33

<210> SEQ ID NO 46
<211> LENGTH: 8
<212> TYPE: PRT
<213> ORGANISM: Ichthyophthirius multifiliis

<400> SEQUENCE: 46

Gly Thr Ala Leu Asp Asp Gly Val
  1               5

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: reverse
      primer

<400> SEQUENCE: 47
gtggatccag tacatgttac artacctgc                                       29

<210> SEQ ID NO 48
<211> LENGTH: 7
<212> TYPE: PRT
<213> ORGANISM: Ichthyophthirius multifiliis -continued

<400> SEQUENCE: 48

Ala Gly Thr Asp Thr Cys Thr
1 5

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: reverse primer

<400> SEQUENCE: 49
gtggatccrc cagaagttaa ttttttakta c 31

<210> SEQ ID NO 50
<211> LENGTH: 9
<212> TYPE: PRT
<213> ORGANISM: Ichthyophthirius multifiliis

<400> SEQUENCE: 50

Cys Thr Lys Lys Leu Thr Ser Gly Ala
1 5

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: reverse primer

<400> SEQUENCE: 51
gtggatccaa ggaaatygat aaaaawttag cg 32

<210> SEQ ID NO 52
<211> LENGTH: 9
<212> TYPE: PRT
<213> ORGANISM: Ichthyophthirius multifiliis

<400> SEQUENCE: 52

Phe Ala Lys Phe Leu Ser Ile Ser Leu
1 5

<210> SEQ ID NO 53
<211> LENGTH: 1404
<212> TYPE: DNA
<213> ORGANISM: Artificial Sequence
<220> FEATURE:
<223> OTHER INFORMATION: Description of Artificial Sequence: synthetic G5 proline mutant i-antigen

<400> SEQUENCE: 53
atgaagaaca acatcccggt gatcctgatc atctctctgt tcatcaacca gatcaagtct 60
gctaactgtc ctgtgggaac cgagaccaac accgctggac aggtggacga cctgggaacc 120
cctgctaact gtgtgaactg tcagaagaac ttctactaca acaacgctgc tgctttcgtg 180
cctggagctt ctacctgtac cccttgtcct cagaagaagg acgctggagc tcagcctaac 240
cctcctgcta ccgctaacct ggtgacccag tgtaacgtga agtgtcctgc tggaaccgct 300
atcgctggag gagctaccga ctacgctgct atcatcaccg agtgtgtgaa ctgtcgcatc 360
aacttctaca acgagaacgc tcctaacttc aacgctggag cttctacctg taccgcttgt 420

-continued

```
cctgtgaacc gtgtgggagg agctctgacc gctggaaacg ctgctaccat cgtggctcag     480
tgtaacgtgg cttgtcctac cggaaccgct ctggacgacg gagtgaccac cgactacgtg     540
cgctctttca ccgagtgtgt gaagtgtcgc ctgaacttct actacaacgg aaacaacgga     600
aacacccctt tcaaccctgg aaagtctcag tgtaccccct tgtcctgcta tcaagcctgct    660 aacgtggctc aggctaccct gggaaacgac gctaccatca ccgctcagtg taacgtggct     720
tgtcctgacg gaaccatctc tgctgctgga gtgaacaact gggtggctca gaacaccgag     780
tgtaccaact gtgctcctaa cttctacaac aacaacgctc ctaacttcaa ccctggaaac     840
tctacctgtc tgccttgtcc tgctaacaag gactacggag ctgaggctac cgctggagga     900
gctgctaccc tggctaagca gtgtaacatc gcttgtcctg acggaaccgc tatcgcttct     960
ggagctacca actacgtgat cctgcagacc gagtgtctga actgtgctgc taacttctac    1020
ttcgacggaa caacttcca ggctggatct ctcgctgta aggcttgtcc tgctaacaag      1080
gtgcagggag ctgtggctac cgctggagga accgctaccc tgatcgctca gtgtgctctg    1140
gagtgtcctg ctggaaccgt gctgaccgac ggaaccacct ctacctacaa gcaggctgct    1200
tctgagtgtg tgaagtgtgc tgctaacttc tacaccacca gcagaccga ctgggtggct     1260 ggaatcgaca cctgtacctc ttgtaacaag aagctgacct ctggagctga ggctaacctg    1320
cctgagtctg ctaagaagaa catccagtgt gacttcgcta acttcctgtc tatctctctg    1380
ctgctgatct cttactacct gctg                                           1404
```

<210> SEQ ID NO 54
<211> LENGTH: 468
<212> TYPE: PRT
<213> ORGANISM: Artificial Sequence
<220> FEATURE:
<223> OTHER INFORMATION: Description of Artificial Sequence: synthetic
G5 proline mutant antigen protein

<400> SEQUENCE: 54

```
Met Lys Asn Asn Ile Pro Val Ile Leu Ile Ile Ser Leu Phe Ile Asn
  1               5                  10                  15

Gln Ile Lys Ser Ala Asn Cys Pro Val Gly Thr Glu Thr Asn Thr Ala
             20                  25                  30

Gly Gln Val Asp Asp Leu Gly Thr Pro Ala Asn Cys Val Asn Cys Gln
         35                  40                  45

Lys Asn Phe Tyr Tyr Asn Asn Ala Ala Ala Phe Val Pro Gly Ala Ser
     50                  55                  60

Thr Cys Thr Pro Cys Pro Gln Lys Lys Asp Ala Gly Ala Gln Pro Asn
 65                  70                  75                  80

Pro Pro Ala Thr Ala Asn Leu Val Thr Gln Cys Asn Val Lys Cys Pro
                 85                  90                  95

Ala Gly Thr Ala Ile Ala Gly Gly Ala Thr Asp Tyr Ala Ala Ile Ile
            100                 105                 110

Thr Glu Cys Val Asn Cys Arg Ile Asn Phe Tyr Asn Glu Asn Ala Pro
        115                 120                 125

Asn Phe Asn Ala Gly Ala Ser Thr Cys Thr Ala Cys Pro Val Asn Arg
    130                 135                 140

Val Gly Gly Ala Leu Thr Ala Gly Asn Ala Ala Thr Ile Val Ala Gln
145                 150                 155                 160

Cys Asn Val Ala Cys Pro Thr Gly Thr Ala Leu Asp Asp Gly Val Thr
                165                 170                 175

Thr Asp Tyr Val Arg Ser Phe Thr Glu Cys Val Lys Cys Arg Leu Asn
```

```
                180                 185                 190
Phe Tyr Tyr Asn Gly Asn Asn Gly Asn Thr Pro Phe Asn Pro Gly Lys
            195                 200                 205
Ser Gln Cys Thr Pro Cys Pro Ala Ile Lys Pro Ala Asn Val Ala Gln
        210                 215                 220
Ala Thr Leu Gly Asn Asp Ala Thr Ile Thr Ala Gln Cys Asn Val Ala
225                 230                 235                 240
Cys Pro Asp Gly Thr Ile Ser Ala Ala Gly Val Asn Asn Trp Val Ala
                245                 250                 255
Gln Asn Thr Glu Cys Thr Asn Cys Ala Pro Asn Phe Tyr Asn Asn Asn
            260                 265                 270
Ala Pro Asn Phe Asn Pro Gly Asn Ser Thr Cys Leu Pro Cys Pro Ala
        275                 280                 285
Asn Lys Asp Tyr Gly Ala Glu Ala Thr Ala Gly Gly Ala Ala Thr Leu
290                 295                 300
Ala Lys Gln Cys Asn Ile Ala Cys Pro Asp Gly Thr Ala Ile Ala Ser
305                 310                 315                 320
Gly Ala Thr Asn Tyr Val Ile Leu Gln Thr Glu Cys Leu Asn Cys Ala
                325                 330                 335
Ala Asn Phe Tyr Phe Asp Gly Asn Asn Phe Gln Ala Gly Ser Ser Arg
            340                 345                 350
Cys Lys Ala Cys Pro Ala Asn Lys Val Gln Gly Ala Val Ala Thr Ala
        355                 360                 365
Gly Gly Thr Ala Thr Leu Ile Ala Gln Cys Ala Leu Glu Cys Pro Ala
370                 375                 380
Gly Thr Val Leu Thr Asp Gly Thr Thr Ser Thr Tyr Lys Gln Ala Ala
385                 390                 395                 400
Ser Glu Cys Val Lys Cys Ala Ala Asn Phe Tyr Thr Thr Lys Gln Thr
                405                 410                 415
Asp Trp Val Ala Gly Ile Asp Thr Cys Thr Ser Cys Asn Lys Lys Leu
            420                 425                 430
Thr Ser Gly Ala Glu Ala Asn Leu Pro Glu Ser Ala Lys Lys Asn Ile
        435                 440                 445
Gln Cys Asp Phe Ala Asn Phe Leu Ser Ile Ser Leu Leu Leu Ile Ser
450                 455                 460
Tyr Tyr Leu Leu
465

<210> SEQ ID NO 55
<211> LENGTH: 72
<212> TYPE: PRT
<213> ORGANISM: Ichthyophthirius multifiliis

<400> SEQUENCE: 55

Cys Pro Val Gly Thr Glu Thr Asn Thr Ala Gly Gln Val Asp Asp Leu
1               5                   10                  15
Gly Thr Pro Ala Asn Cys Val Asn Cys Gln Lys Asn Phe Tyr Tyr Asn
            20                  25                  30
Asn Ala Ala Ala Phe Val Pro Gly Ala Ser Thr Cys Thr Pro Cys Pro
        35                  40                  45
Gln Lys Lys Asp Ala Gly Ala Gln Pro Asn Pro Ala Thr Ala Asn
    50                  55                  60
Leu Val Thr Gln Cys Asn Val Lys
65                  70
```

```
<210> SEQ ID NO 56
<211> LENGTH: 70
<212> TYPE: PRT
<213> ORGANISM: Ichthyophthirius multifiliis

<400> SEQUENCE: 56

Cys Pro Ala Gly Thr Ala Ile Ala Gly Gly Ala Thr Asp Tyr Ala Ala
 1               5                  10                  15

Ile Ile Thr Glu Cys Val Asn Cys Arg Ile Asn Phe Tyr Asn Glu Asn
            20                  25                  30

Ala Pro Asn Phe Asn Ala Gly Ala Ser Thr Cys Thr Ala Cys Pro Val
        35                  40                  45

Asn Arg Val Gly Gly Ala Leu Thr Ala Gly Asn Ala Ala Thr Ile Val
    50                  55                  60

Ala Gln Cys Asn Val Ala
65                  70

<210> SEQ ID NO 57
<211> LENGTH: 76
<212> TYPE: PRT
<213> ORGANISM: Ichthyophthirius multifiliis

<400> SEQUENCE: 57

Cys Pro Thr Gly Thr Ala Leu Asp Asp Gly Val Thr Thr Asp Tyr Val
 1               5                  10                  15

Arg Ser Phe Thr Glu Cys Val Lys Cys Arg Leu Asn Phe Tyr Tyr Asn
            20                  25                  30

Gly Asn Asn Gly Asn Thr Pro Phe Asn Pro Gly Lys Ser Gln Cys Thr
        35                  40                  45

Pro Cys Pro Ala Ile Lys Pro Ala Asn Val Ala Gln Ala Thr Leu Gly
    50                  55                  60

Asn Asp Ala Thr Ile Thr Ala Gln Cys Asn Val Ala
65                  70                  75

<210> SEQ ID NO 58
<211> LENGTH: 71
<212> TYPE: PRT
<213> ORGANISM: Ichthyophthirius multifiliis

<400> SEQUENCE: 58

Cys Pro Asp Gly Thr Ile Ser Ala Ala Gly Val Asn Asn Trp Val Ala
 1               5                  10                  15

Gln Asn Thr Glu Cys Thr Asn Cys Ala Pro Asn Phe Tyr Asn Asn Asn
            20                  25                  30

Ala Pro Asn Phe Asn Pro Gly Asn Ser Thr Cys Leu Pro Cys Pro Ala
        35                  40                  45

Asn Lys Asp Tyr Gly Ala Glu Ala Thr Ala Gly Gly Ala Ala Thr Leu
    50                  55                  60

Ala Lys Gln Cys Asn Ile Ala
65                  70

<210> SEQ ID NO 59
<211> LENGTH: 70
<212> TYPE: PRT
<213> ORGANISM: Ichthyophthirius multifiliis

<400> SEQUENCE: 59

Cys Pro Asp Gly Thr Ala Ile Ala Ser Gly Ala Thr Asn Tyr Val Ile
 1               5                  10                  15
```

```
Leu Gln Thr Glu Cys Leu Asn Cys Ala Ala Asn Phe Tyr Phe Asp Gly
         20                  25                  30

Asn Asn Phe Gln Ala Gly Ser Ser Arg Cys Lys Ala Cys Pro Ala Asn
         35                  40                  45

Lys Val Gln Gly Ala Val Ala Thr Ala Gly Gly Thr Ala Thr Leu Ile
     50                  55                  60

Ala Gln Cys Ala Leu Glu
 65              70

<210> SEQ ID NO 60
<211> LENGTH: 72
<212> TYPE: PRT
<213> ORGANISM: Ichthyophthirius multifiliis

<400> SEQUENCE: 60

Cys Pro Ala Gly Thr Val Leu Thr Asp Gly Thr Thr Ser Thr Tyr Lys
 1               5                  10                  15

Gln Ala Ala Ser Glu Cys Val Lys Cys Ala Ala Asn Phe Tyr Thr Thr
         20                  25                  30

Lys Gln Thr Asp Trp Val Ala Gly Ile Asp Thr Cys Thr Ser Cys Asn
         35                  40                  45

Lys Lys Leu Thr Ser Gly Ala Glu Ala Asn Leu Pro Glu Ser Ala Lys
     50                  55                  60

Lys Asn Ile Gln Cys Asp Phe Ala
 65              70

<210> SEQ ID NO 61
<211> LENGTH: 409
<212> TYPE: PRT
<213> ORGANISM: Ichthyophthirius multifiliis

<400> SEQUENCE: 61

Ala Val Pro Cys Pro Asp Gly Thr Gln Thr Gln Ala Gly Leu Thr Asp
 1               5                  10                  15

Val Gly Ala Ala Asp Leu Gly Thr Cys Val Asn Cys Arg Pro Asn Phe
         20                  25                  30

Tyr Tyr Asn Gly Gly Ala Ala Gln Gly Glu Ala Asn Gly Asn Gln Pro
         35                  40                  45

Phe Ala Ala Asn Asn Ala Ala Arg Gly Ile Cys Val Pro Cys Gln Ile
     50                  55                  60

Asn Arg Val Gly Ser Val Thr Asn Ala Gly Asp Leu Ala Thr Leu Ala
 65                  70                  75                  80

Thr Gln Cys Ser Thr Gln Cys Pro Thr Gly Thr Ala Leu Asp Asp Gly
             85                  90                  95

Val Thr Asp Val Phe Asp Arg Ser Ala Ala Gln Cys Val Lys Cys Lys
            100                 105                 110

Pro Asn Phe Tyr Tyr Asn Gly Gly Ser Pro Gln Gly Glu Ala Pro Gly
            115                 120                 125

Val Gln Val Phe Ala Ala Gly Ala Ala Ala Gly Val Ala Ala Val
        130                 135                 140

Thr Ser Gln Cys Val Pro Cys Gln Leu Asn Lys Asn Asp Ser Pro Ala
145                 150                 155                 160

Thr Ala Gly Ala Gln Ala Asn Leu Ala Thr Gln Cys Ser Asn Gln Cys
                165                 170                 175

Pro Thr Gly Thr Val Leu Asp Asp Gly Val Thr Leu Val Phe Asn Thr
            180                 185                 190
```

-continued

```
Ser Ala Thr Leu Cys Val Lys Cys Arg Pro Asn Phe Tyr Tyr Asn Gly
            195                 200                 205

Gly Ser Pro Gln Gly Glu Ala Pro Gly Val Gln Val Phe Ala Ala Gly
        210                 215                 220

Ala Ala Ala Ala Gly Val Ala Ala Val Thr Ser Gln Cys Val Pro Cys
225                 230                 235                 240

Gln Ile Asn Lys Asn Asp Ser Pro Ala Thr Ala Gly Ala Gln Ala Asn
                245                 250                 255

Leu Ala Thr Gln Cys Ser Thr Gln Cys Pro Thr Gly Thr Ala Ile Gln
            260                 265                 270

Asp Gly Val Thr Leu Val Phe Ser Asn Ser Thr Gln Cys Ser Gln
        275                 280                 285

Cys Ile Ala Asn Tyr Phe Phe Asn Gly Asn Phe Glu Ala Gly Lys Ser
290                 295                 300

Gln Cys Leu Lys Cys Pro Val Ser Lys Thr Thr Pro Ala His Ala Pro
305                 310                 315                 320

Gly Asn Thr Ala Thr Gln Ala Thr Gln Cys Leu Thr Cys Pro Ala
                325                 330                 335

Gly Thr Val Leu Asp Asp Gly Thr Ser Thr Asn Phe Val Ala Ser Ala
            340                 345                 350

Thr Glu Cys Thr Lys Cys Ser Ala Gly Phe Phe Ala Ser Lys Thr Thr
            355                 360                 365

Gly Phe Thr Ala Gly Thr Asp Thr Cys Thr Glu Cys Thr Lys Lys Leu
        370                 375                 380

Thr Ser Gly Ala Thr Ala Lys Val Tyr Ala Glu Ala Thr Gln Lys Val
385                 390                 395                 400

Gln Cys Ala Ser Thr Thr Phe Ala Lys
                405

<210> SEQ ID NO 62
<211> LENGTH: 399
<212> TYPE: PRT
<213> ORGANISM: Giardia lamblia virus

<400> SEQUENCE: 62

Ala Val Asp Cys Gln Gly Ser Ala Gly Tyr Tyr Thr Asp Asp Ser Val
1               5                   10                  15

Ser Asp Ala Lys Glu Cys Lys Lys Cys Asn Ala Pro Cys Thr Ala Cys
            20                  25                  30

Ala Gly Thr Ala Asp Lys Cys Thr Lys Cys Asp Ala Asn Gly Ala Ala
        35                  40                  45

Pro Tyr Leu Lys Lys Thr Asn Pro Ser Asp Pro Thr Gly Thr Cys Val
    50                  55                  60

Ser Ala Val Asp Cys Gln Gly Ser Ala Gly Tyr Tyr Thr Asp Asp Ser
65                  70                  75                  80

Val Ser Asp Ala Lys Glu Cys Lys Lys Cys Ala Glu Gly Gln Lys Pro
                85                  90                  95

Asn Thr Ala Gly Thr Gln Cys Phe Ser Cys Ser Asp Ala Asn Cys Glu
            100                 105                 110

Arg Cys Asp Gln Asn Asp Val Cys Ala Arg Cys Ser Thr Gly Ala Pro
        115                 120                 125

Pro Glu Asn Gly Lys Cys Pro Ala Ala Thr Pro Gly Cys His Ser Ser
    130                 135                 140

Cys Asp Gly Cys Thr Glu Asn Ala Met Thr Asn Gln Ala Asp Lys Cys
```

```
                145                 150                 155                 160
Thr Gly Cys Lys Glu Gly Arg Tyr Leu Lys Pro Glu Ser Ala Ala Gly
                    165                 170                 175

Gln Ser Gly Thr Cys Leu Thr Ala Glu Glu Cys Thr Ser Asp Thr Thr
                180                 185                 190

His Phe Thr Lys Glu Lys Ala Gly Asp Ser Lys Gly Met Cys Leu Pro
            195                 200                 205

Cys Ser Asp Ala Thr His Gly Ile Ala Gly Cys Lys Lys Cys Ala Leu
        210                 215                 220

Lys Thr Leu Ser Gly Glu Ala Glu Ser Thr Val Val Cys Ser Glu Cys
225                 230                 235                 240

Thr Asp Lys Trp Leu Thr Pro Ser Gly Asn Ala Cys Leu Asp Asn Cys
                245                 250                 255

Pro Ala Gly Thr Tyr Pro Asn Asp Asn Asn Leu Cys Thr Ser Cys His
                260                 265                 270

Asp Thr Cys Ala Glu Cys Asn Gly Asn Ala Asp Arg Ala Ser Cys Thr
            275                 280                 285

Ala Cys Tyr Pro Gly Tyr Ser Leu Leu Tyr Gly Ser Cys Thr Ala Gly
        290                 295                 300

Thr Cys Val Lys Glu Cys Thr Gly Ala Phe Gly Ala Asn Cys Ala Asp
305                 310                 315                 320

Gly Gln Cys Thr Ala Asp Val Gly Gly Ala Lys Tyr Cys Ala Gln Cys
                325                 330                 335

Lys Asp Gly Tyr Ala Pro Ile Asp Gly Ile Cys Thr Ala Val Ala Ala
                340                 345                 350

Ala Gly Arg Thr Asn Val Cys Thr Ala Ala Asp Gly Thr Cys Thr Lys
            355                 360                 365

Cys Ala Gly Glu Tyr Thr Leu Met Ser Gly Gly Cys Tyr Gly Val Ala
        370                 375                 380

Lys Leu Pro Gly Lys Ser Val Cys Thr Leu Ala Ser Asn Gly Lys
385                 390                 395

<210> SEQ ID NO 63
<211> LENGTH: 5
<212> TYPE: PRT
<213> ORGANISM: Ichthyophthirius multifiliis

<400> SEQUENCE: 63

Val Asn Ile His Gln
  1               5

<210> SEQ ID NO 64
<211> LENGTH: 77
<212> TYPE: DNA
<213> ORGANISM: Ichthyophthirius multifiliis

<400> SEQUENCE: 64
gtaaatatcc attaatgaag cttcgaaaac agtggtggta gtaccttatt catgcttgaa      60
gtatttagaa tcaagag                                                    77

<210> SEQ ID NO 65
<211> LENGTH: 33
<212> TYPE: PRT
<213> ORGANISM: Ichthyophthirius multifiliis

<400> SEQUENCE: 65

Lys Val Tyr Ala Glu Ala Thr Gln Lys Val Gln Cys Ala Ser Thr Thr
```

```
            1               5              10              15
Phe Ala Lys Phe Leu Ser Ile Ser Leu Leu Phe Ile Ser Phe Tyr Leu
                20                  25                  30
Leu

<210> SEQ ID NO 66
<211> LENGTH: 202
<212> TYPE: DNA
<213> ORGANISM: Ichthyophthirius multifiliis

<400> SEQUENCE: 66
aaagtatatg ctgaagctac tcaaaaagta taatgcgcct ccactacttt cgctaaattt      60
ttatcgattt ccttattatt tatttctttc tatttattgt gatgaataaa ataattcata     120
ttattttatt tttttatttt atgtttataa attaaaaaat agataaaatt taaaatatat     180
taaaaataat tttttatata aa                                              202

<210> SEQ ID NO 67
<211> LENGTH: 199
<212> TYPE: DNA
<213> ORGANISM: Ichthyophthirius multifiliis

<400> SEQUENCE: 67
aaagtatatg ctgaagctac tcaaaaagta taatgcgcct ccactacttt cgctaaattt      60
ttatcgattt ccttattatt tatttctttc tatttattgt gattaataaa ataattcata     120
ttattttatt tttttatttt atgtttataa attaaaaaat agataaaatt taaaatatat     180
taaaaaaaaa aaaaaaaa                                                   199

<210> SEQ ID NO 68
<211> LENGTH: 162
<212> TYPE: DNA
<213> ORGANISM: Ichthyophthirius multifiliis

<400> SEQUENCE: 68
aaagtatatg ctgaagctac tcaaaaagta taatgcgcct ccactacttt cgctaaattt      60
ttatcgattt ccttattatt tatttctttc tatttattgt gatgaataaa ataattcata     120
ttattttatt tttttatttt atgtttataa attaaaaaat ag                        162

<210> SEQ ID NO 69
<211> LENGTH: 119
<212> TYPE: DNA
<213> ORGANISM: Ichthyophthirius multifiliis

<400> SEQUENCE: 69
aaagtatatg ctgaagctac tcaaaaagta taatgcgcct ccactacttt cgctaaattt      60
ttatcgattt ccttattatt tatttctttc tatttattgt gatgaataaa ataattcat     119

<210> SEQ ID NO 70
<211> LENGTH: 117
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 70
atgggaattc aaatgaagaa caacatcctg gtgatcctga tcatctctct gttcatcaac      60
cagatcaagt ctgctaactg tcctgtggga accgagacca caccgctgg acaggtg        117
```

<210> SEQ ID NO 71
<211> LENGTH: 104
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 71
ctccaggcac gaaagcagca gcgttgttgt agtagaagtt cttctgacag ttcacacagt    60
tagcaggggt tcccaggtcg tccacctgtc cagcggtgtt ggtc                   104

<210> SEQ ID NO 72
<211> LENGTH: 100
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 72
cgctgctgct ttcgtgcctg gagcttctac ctgtacccct tgtcctcaga agaaggacgc    60
tggagctcag cctaaccctc ctgctaccgc taacctggtg                        100

<210> SEQ ID NO 73
<211> LENGTH: 95
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 73
gatgatagca gcgtagtcgg tagctcctcc agcgatagcg gttccagcag gacacttcac    60
gttacactgg gtcaccaggt tagcggtagc aggag                             95

<210> SEQ ID NO 74
<211> LENGTH: 138
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 74
gctaccgact acgctgctat catcaccgag tgtgtgaact gtcgcatcaa cttctacaac    60
gagaacgctc ctaacttcaa cgctggagct tctacctgta ccgcttgtcc tgtgaaccgc   120
gtgggaggag ctctgacc                                                138

<210> SEQ ID NO 75
<211> LENGTH: 123
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 75
ggtgaaagag cgcacgtagt cggtggtcac tccgtcgtcc agagcggttc cggtaggaca    60
agccacgtta cactgagcca cgatggtagc agcgtttcca gcggtcagag ctcctcccac   120
gcg                                                                123

<210> SEQ ID NO 76
<211> LENGTH: 99
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 76
gactacgtgc gctctttcac cgagtgtgtg aagtgtcgcc tgaacttcta ctacaacgga      60
aacaacggaa acaccccttt caaccctgga aagtctcag                            99

<210> SEQ ID NO 77
<211> LENGTH: 95
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 77
gtgatggtag cgtcgtttcc cagggtagcc tgagccacgt tagcaggctt gatagcagga      60 caagggtac actgagactt tccaggttg aaagg                                  95

<210> SEQ ID NO 78
<211> LENGTH: 94
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 78
gggaaacgac gctaccatca ccgctcagtg taacgtggct tgtcctgacg gaaccatctc      60
tgctgctgga gtgaacaact gggtggctca gaac                                 94

<210> SEQ ID NO 79
<211> LENGTH: 100
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 79
cagacaggta gagtttccag ggttgaagtt aggagcgttg ttgttgtaga agttaggagc      60
acagttggta cactcggtgt tctgagccac ccagttgttc                           100

<210> SEQ ID NO 80
<211> LENGTH: 89
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 80
ccctggaaac tctacctgtc tgccttgtcc tgctaacaag gactacggag ctgaggctac      60
cgctggagga gctgctaccc tggctaagc                                       89

<210> SEQ ID NO 81
<211> LENGTH: 90

```
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 81
ggtctgcagg atcacgtagt tggtagctcc agaagcgata gcggttccgt caggacaagc    60
gatgttacac tgcttagcca gggtagcagc                                     90

<210> SEQ ID NO 82
<211> LENGTH: 95
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 82
caactacgtg atcctgcaga ccgagtgtct gaactgtgct gctaacttct acttcgacgg    60
aaacaacttc caggctggat cttctcgctg taagg                                95

<210> SEQ ID NO 83
<211> LENGTH: 92
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 83
gagcgatcag ggtagcggtt cctccagcgg tagccacagc tccctgcacc ttgttagcag    60
gacaagcctt acagcgagaa gatccagcct gg                                  92

<210> SEQ ID NO 84
<211> LENGTH: 94
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 84
gaaccgctac cctgatcgct cagtgtgctc tggagtgtcc tgctggaacc gtgctgaccg    60
acggaaccac ctctacctac aagcaggctg cttc                                94

<210> SEQ ID NO 85
<211> LENGTH: 92
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 85
ggtgtcgatt ccagccaccc agtcggtctg cttggtggtg tagaagttag cagcacactt    60
cacacactca gaagcagcct gcttgtaggt ag                                  92

<210> SEQ ID NO 86
<211> LENGTH: 92
<212> TYPE: DNA
<213> ORGANISM: Artificial Sequence
<220> FEATURE:
<223> OTHER INFORMATION: Description of Artificial Sequence:
```

-continued

```
          oligonucleotide primers

<400> SEQUENCE: 86
gggtggctgg aatcgacacc tgtacctctt gtaacaagaa gctgacctct ggagctgagg    60
ctaacctgcc tgagtctgct aagaagaaca tc                                  92

<210> SEQ ID NO 87
<211> LENGTH: 95
<212> TYPE: DNA
<213> ORGANISM: Artificial Sequence
<220> FEATURE:
<223> OTHER INFORMATION: Description of Artificial Sequence:
      oligonucleotide primers

<400> SEQUENCE: 87
gagggatcct tattacagca ggtagtaaga gatcagcagc agagagatag acaggaagtt    60
agcgaagtca cactggatgt tcttcttagc agact                               95

<210> SEQ ID NO 88
<211> LENGTH: 52
<212> TYPE: PRT
<213> ORGANISM: Artificial Sequence
<220> FEATURE:
<223> OTHER INFORMATION: Description of Artificial Sequence:  repeating
      primary structure motif
<221> NAME/KEY: UNSURE
<222> LOCATION: (2)..(3)
<223> OTHER INFORMATION: amino acid
<221> NAME/KEY: UNSURE
<222> LOCATION: (5)..(24)
<223> OTHER INFORMATION: amino acid
<221> NAME/KEY: UNSURE
<222> LOCATION: (26)..(28)
<223> OTHER INFORMATION: amino acid
<221> NAME/KEY: UNSURE
<222> LOCATION: (31)..(48)
<223> OTHER INFORMATION: amino acid
<221> NAME/KEY: UNSURE
<222> LOCATION: (50)..(51)
<223> OTHER INFORMATION: amino acid

<400> SEQUENCE: 88

Cys Xaa Xaa Cys Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Cys Xaa Xaa Xaa Cys Pro Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Cys Xaa Xaa Cys
    50

<210> SEQ ID NO 89
<211> LENGTH: 58
<212> TYPE: PRT
<213> ORGANISM: Artificial Sequence
<220> FEATURE:
<223> OTHER INFORMATION: Description of Artificial Sequence:  repeating
      primary structure motif
<221> NAME/KEY: UNSURE
<222> LOCATION: (2)..(3)
<223> OTHER INFORMATION: amino acid
<221> NAME/KEY: UNSURE
<222> LOCATION: (5)..(24)
<223> OTHER INFORMATION: amino acid
<221> NAME/KEY: UNSURE
<222> LOCATION: (27)..(29)
<223> OTHER INFORMATION: amino acid
<221> NAME/KEY: UNSURE
```

```
<222> LOCATION: (32)
<223> OTHER INFORMATION: amino acid
<221> NAME/KEY: UNSURE
<222> LOCATION: (35)..(54)
<223> OTHER INFORMATION: amino acid
<221> NAME/KEY: UNSURE
<222> LOCATION: (56)..(57)
<223> OTHER INFORMATION: amino acid

<400> SEQUENCE: 89

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Gln Cys Xaa Xaa Cys Pro Xaa
                20                  25                  30

Gly Thr Xaa Xaa Xaa Xaa Xaa Xaa Xaa Xaa Xaa Xaa Xaa Xaa Xaa
            35                  40                  45

Xaa Xaa Xaa Xaa Xaa Xaa Cys Xaa Xaa Cys
    50                  55

<210> SEQ ID NO 90
<211> LENGTH: 16
<212> TYPE: PRT
<213> ORGANISM: Ichthyophthirius multifiliis

<400> SEQUENCE: 90

Met Lys Tyr Asn Ile Leu Leu Ile Leu Ile Ile Ser Leu Phe Ile Asn
1               5                   10                  15

<210> SEQ ID NO 91
<211> LENGTH: 16
<212> TYPE: PRT
<213> ORGANISM: Ichthyophthirius multifiliis

<400> SEQUENCE: 91

Met Lys Asn Asn Ile Leu Val Ile Leu Ile Ile Ser Leu Phe Ile Asn
1               5                   10                  15

<210> SEQ ID NO 92
<211> LENGTH: 12
<212> TYPE: PRT
<213> ORGANISM: Ichthyophthirius multifiliis

<400> SEQUENCE: 92

Cys Pro Thr Gly Thr Ala Leu Asp Asp Gly Val Thr
1               5                   10

<210> SEQ ID NO 93
<211> LENGTH: 13
<212> TYPE: PRT
<213> ORGANISM: Ichthyophthirius multifiliis

<400> SEQUENCE: 93

Cys Val Lys Cys Lys Pro Asn Phe Tyr Tyr Asn Gly Gly
1               5                   10

<210> SEQ ID NO 94
<211> LENGTH: 12
<212> TYPE: PRT
<213> ORGANISM: Ichthyophthirius multifiliis

<400> SEQUENCE: 94

Cys Val Lys Cys Arg Leu Asn Phe Tyr Tyr Asn Gly
1               5                   10
```

```
<210> SEQ ID NO 95
<211> LENGTH: 11
<212> TYPE: PRT
<213> ORGANISM: Ichthyophthirius multifiliis

<400> SEQUENCE: 95

Cys Pro Ala Gly Thr Val Leu Asp Asp Gly Thr
 1               5                  10

<210> SEQ ID NO 96
<211> LENGTH: 11
<212> TYPE: PRT
<213> ORGANISM: Ichthyophthirius multifiliis

<400> SEQUENCE: 96

Cys Pro Ala Gly Thr Val Leu Thr Asp Gly Thr
 1               5                  10

<210> SEQ ID NO 97
<211> LENGTH: 19
<212> TYPE: PRT
<213> ORGANISM: Ichthyophthirius multifiliis

<400> SEQUENCE: 97

Ala Gly Thr Asp Thr Cys Thr Glu Cys Thr Lys Lys Leu Thr Ser Gly
 1               5                  10                  15

Ala Thr Ala

<210> SEQ ID NO 98
<211> LENGTH: 19
<212> TYPE: PRT
<213> ORGANISM: Ichthyophthirius multifiliis

<400> SEQUENCE: 98

Ala Gly Ile Asp Thr Cys Thr Ser Cys Asn Lys Lys Leu Thr Ser Gly
 1               5                  10                  15

Ala Glu Ala

<210> SEQ ID NO 99
<211> LENGTH: 17
<212> TYPE: PRT
<213> ORGANISM: Ichthyophthirius multifiliis

<400> SEQUENCE: 99

Phe Ala Lys Phe Leu Ser Ile Ser Leu Leu Phe Ile Ser Phe Tyr Leu
 1               5                  10                  15

Leu

<210> SEQ ID NO 100
<211> LENGTH: 17
<212> TYPE: PRT
<213> ORGANISM: Ichthyophthirius multifiliis

<400> SEQUENCE: 100

Phe Ala Asn Phe Leu Ser Ile Ser Leu Leu Leu Ile Ser Tyr Tyr Leu
 1               5                  10                  15

Leu

<210> SEQ ID NO 101
<211> LENGTH: 12
<212> TYPE: PRT
<213> ORGANISM: Artificial Sequence
<220> FEATURE:
```

-continued

```
<223> OTHER INFORMATION: Description of Artificial Sequence:  short
      linker sequence

<400> SEQUENCE: 101

Gly Ser Gly Gly Gly Gly Ser Gly Gly Gly Gly Ser
  1               5                  10

<210> SEQ ID NO 102
<211> LENGTH: 1410
<212> TYPE: DNA
<213> ORGANISM: Artificial Sequence
<220> FEATURE:
<223> OTHER INFORMATION: Description of Artificial Sequence:  synthetic
      55kD i-antigen coding region

<400> SEQUENCE: 102
atgaagaaca acatcctggt gatcctgatc atctctctgt tcatcaacca gatcaagtct     60
gctaactgtc ctgtgggaac cgagaccaac accgctggac aggtggacga cctgggaacc    120
cctgctaact gtgtgaactg tcagaagaac ttctactaca acaacgctgc tgctttcgtg    180
cctggagctt ctacctgtac cccttgtcct cagaagaagg acgctggagc tcagcctaac    240
cctcctgcta ccgctaacct ggtgacccag tgtaacgtga agtgtcctgc tggaaccgct    300
atcgctggag gagctaccga ctacgctgct atcatcaccg agtgtgtgaa ctgtcgcatc    360
aacttctaca acgagaacgc tcctaacttc aacgctggag cttctacctg taccgcttgt    420
cctgtgaacc gcgtgggagg agctctgacc gctggaaacg ctgctaccat cgtggctcag    480
tgtaacgtgg cttgtcctac cggaaccgct ctggacgacg gagtgaccac cgactacgtg    540
cgctctttca ccgagtgtgt gaagtgtcgc ctgaacttct actacaacgg aaacaacgga    600
aacacccctt tcaaccctgg aaagtctcag tgtacccctt gtcctgctat caagcctgct    660
aacgtggctc aggctaccct gggaaacgac gctaccatca ccgctcagtg taacgtggct    720
tgtcctgacg gaaccatctc tgctgctgga gtgaacaact gggtggctca gaacaccgag    780
tgtaccaact gtgctcctaa cttctacaac aacaacgctc ctaacttcaa ccctggaaac    840
tctacctgtc tgccttgtcc tgctaacaag gactacggag ctgaggctac cgctggagga    900
gctgctaccc tggctaagca gtgtaacatc gcttgtcctg acggaaccgc tatcgcttct    960
ggagctacca actacgtgat cctgcagacc gagtgtctga actgtgctgc taacttctac   1020
ttcgacggaa acaacttcca ggctggatct tctcgctgta aggcttgtcc tgctaacaag   1080
gtgcagggag ctgtggctac cgctggagga accgctaccc tgatcgctca gtgtgctctg   1140
gagtgtcctg ctggaaccgt gctgaccgac ggaaccacct ctacctacaa gcaggctgct   1200
tctgagtgtg tgaagtgtgc tgctaacttc tacaccacca agcagaccga ctgggtggct   1260
ggaatcgaca cctgtacctc ttgtaacaag aagctgacct ctggagctga ggctaacctg   1320
cctgagtctg ctaagaagaa catccagtgt gacttcgcta acttcctgtc tatctctctg   1380
ctgctgatct cttactacct gctgtaataa                                    1410
```

DIAGNOSTIC AND PROTECTIVE ANTIGEN GENE SEQUENCES OF ICHTHYOPHTHIRIUS

This application claims the benefit of U.S. Provisional Application Ser. No. 60/131,121, filed Apr. 27, 1999; U.S. Provisional Application 60/118,634, filed Feb. 4, 1999; U.S. Provisional Application 60/122,372, filed Mar. 2, 1999; and U.S. Provisional Application 60/124,905, filed Mar. 17, 1999, each of which is incorporated herein by reference in its entirety.

CROSS REFERENCE TO RELATED APPLICATIONS

This application incorporates the content of U.S. patent application Ser. No. 09/498,612, entitled "Recombinant Expression of Heterologous Nucleic Acids in Protozoa," filed Feb. 4, 2000.

STATEMENT OF GOVERNMENT RIGHTS

This invention was made with government support under grants from the United States Department of Agriculture (USDA) CSRS NRICGP, Grant No. 95-37204-2139. The U.S. government has certain rights in this invention.

BACKGROUND OF THE INVENTION

*Ichthyophthirius multifiliis* is a holotrichous ciliated protozoan which is an obligate parasite of freshwater fish. The life cycle of the parasite includes a free-living infectious stage (the theront or tomite) and an obligate fish-associated feeding stage (the trophont or trophozoite). The infective theront invades the skin and the gill epithelia, resulting in disturbances in respiratory and excretory functions. Once in epithelial tissue, the theront differentiates into the fish-associated feeding form known as a trophont. When the trophont is mature, it is released from the surface of the fish and secretes material forming a gelatinous cyst. Within the cyst, the mature trophont undergoes multiple cell divisions to produce hundreds of theronts, which are then released from the matrix to begin a new cycle of infection.

Protection from Disease Caused by *I. multifiliis*

Ichthyophthiriasis, the disease caused by this parasite, is commonly referred to as "Ich" or "white spot disease." Under conditions of intensive aquaculture, Ich frequently has a high morbidity and mortality, resulting in significant financial losses to fish producers.

Treatments are available for Ich-infected fish. However, the chemical treatments are effective only against the free-living theronts; there is no known agent for eliminating trophonts associated with the host. Furthermore, some of the chemotherapeutic agents used to treat Ich are suspected to leave residues in treated fish and to be carcinogenic. As a result, certain of the available treatments, e.g., malachite green, are not permitted for fish raised for human consumption. In addition, chemical treatments result in physiological stress to the infected fish beyond that resulting directly from the infection.

Those fish which survive infection by *I. multifiliis* are generally immune to further infection by the live parasite. Early reports suggested that fish (mirror carp) were successfully immunized by exposure to sublethal doses of the parasite (Hines et al., *J. Fish. Biol.* 6:373–378 (1974)) and by exposure to the live parasite in conjunction with chemical treatment. There have also been reports of at least partial protective immunity in fish vaccinated using the killed parasite. For example, a substantial decrease in the number of infective parasites on the body surface of goldfish which had been previously injected with killed theronts was observed when the fish were challenged with a measured dose of live theronts (Parker, *Studies on the Natural History of Ichthyophthirius multifiliis Fouquet 1876, an Ectoparasitic Ciliate of Fish*, Ph.D. Dissertation, The University of Maryland, College Park, Md. (1965)). Areerat ("The Immune Response of Channel Catfish, *Ictalurus punctatus* (Rafinesque), to *Ichthyophthirius multifiliis*", unpublished Master's thesis, Auburn University) reported that channel catfish injected with formalin-fixed trophonts were protected when challenged with a lethal dose of infective theronts. Goven et al. (*J. Fish Biol.* 17:311–316 (1980)) reported initial protection against lethal infection when fish were injected intraperitoneally with theront cilia. The experiment was discontinued when all control fish had died and the fate of the vaccinated fish was not followed further.

More recently, however, Burkhardt et al. (*J. Fish Dis.* 13:401–410 (1990)) reported that neither immersion exposure nor intraperitoneal injection with killed *I. multifiliis* theronts conferred protective immunity to challenge doses of live theronts, although there was a delay in mortality of the vaccinated fish was observed. Likewise, intraperitoneal injection with theront cilia preparations did not prevent mortality, only delayed it. Only intraperitoneal injection with live theronts was effective in preventing mortality after challenge with infective parasites. Those fish which had been injected with live theronts remained protected against infection for an extended time, as evidenced by their resistance to challenge infections at 3 and 13 months after the original injection. Attempted immunization with formalin-fixed trophonts led to some delay in mortality but had an unclear effect on ultimate mortality.

The mucus coating of an immune fish participates in protection from Ich infection. Hines et al. (*J. Fish. Biol.* 6:373–378 (1974)) showed that both sera and mucus from immune fish was capable of immobilizing the infective form of *I. multifiliis*. These authors also noted that fish recovering from Ich had a different distribution of the parasite than did newly infected fish. Newly infected fish exhibited parasites all over the body while a recovering fish exhibits parasites primarily at edges of the fish. These are the parts of the fish which are least well supplied with blood, and therefore, would be less well supplied with antibodies.

Clark et al. (*Devel. Comp. Immun.* 1–2:581–594 (1988)) studied the sera of channel catfish that had been rendered immune to further Ich infection by exposure to sublethal surface infection and treated with chemotherapy. The sera of these immune catfish contain antibodies which specifically bind to *I. multifiliis* cilia; little cross-reactivity was observed for cilia prepared from the free-living ciliate *Tetrahymena thermophila*. Whole *I. multifiliis* cilia and a ciliary membrane fraction gave similar reactions with the immune sera, but axoneme fractions showed little differential reaction in comparisons between immune and preimmune sera. However, attempts to identify the ciliary proteins with which the antibodies reacted using blots from SDS gel electropherograms were not successful. Sera from immune fish also immobilize the parasite in vitro, with an apparent positive correlation between specific antibodies and immobilization of theronts in vitro.

There were early reports that fish vaccinated with *Tetrahymena pyriformis* and with *T. thermophila* or with cilia prepared from *Tetrahymena* were protected from Ich infection (e.g., U.S. Pat. No. 4,309,416, Gratzek et al). It had been proposed that the ciliary membrane antigens from *Tetrahymena* showed cross-reactivity with those of *I. multifiliis*. However, more recent reports showed that attempted vaccination of channel catfish with *T. thermophila* Lwoff cilia did not protect the fish from subsequent challenge with *I. multifiliis* (Burkhardt et al., *J. Fish Dis.* 13:401–410 (1990)). It has been postulated that the previous cross-reactivity was due to the conserved axoneme proteins, rather than due to serologically related ciliary membrane proteins.

*I. multifiliis* i-antigens

A novel mechanism of humoral immunity against *I. multifiliis* was recently described. Rather than being killed on the host, a majority of parasites are forced to exit fish prematurely in response to antibody binding (M. Cross, *J. Fish Dis.*, 15:497–505 (1992))(T. Clark et al., *Parasitol. Today*, 13:477–480 (1997)). While the precise mechanism underlying this phenomenon is unknown, the target antigens responsible for premature exit have been identified as a class of abundant surface membrane proteins known as immobilization antigens, or i-antigens (T. Clark et al., *Annu. Rev. Fish Dis.*, 5:113–131 (1995)). Antibodies against these proteins rapidly immobilize cells in vitro.

I-antigens are common to a variety of hymenostomatid ciliates and have been intensively studied in *Paramecium* and *Tetrahymena* where their expression undergoes marked variation in response to environmental stimuli (F. Caron et al., *Annu. Rev. Microbiol.*, 43:23–42 (1989); Smith et al., *J. Protozool.*, 39:420–428 (1992)). Antigenic switching in these cells results from the differential expression of multiple i-antigen genes under defined sets of conditions and represents one of the most striking examples of antigenic shift in nature. To date, there is little evidence that this type of variation occurs in *Ichthyophthirius*; however, steady-state levels of i-antigen transcripts vary as much as 50 fold during transition from the host-associated trophont to the infective theront stage, and it is clear that the genes for these proteins are developmentally regulated through the parasite life cycle (T. Clark et al., *Proc. Nat. Acad. Sci. USA*, 89:6363–6367 (1992)). Furthermore, serotypic variants of the i-antigens have been described among geographic isolates of the parasite (H. Dickerson et al., *J. Euk. Microbiol.*, 40:816–820 (1993)).

Although i-antigens have gained considerable attention with regard to their mode of expression, their biological function remains obscure. In *Paramecium* and *Tetrahymena*, i-antigens are linked to the plasma membrane through a glycosylphosphatidylinositol (GPI) anchor, and in some cases, form a thick layer that coats the plasma and ciliary membranes (F. Caron et al., *Annu. Rev. Microbiol.*, 43:23–42 (1989)). This has led to speculation that their primary function is to shield the cell membrane from environmental insult; indeed, this fits a general model for the role of GPI-anchored proteins in lower eukaryotes. The fact that cross-linking of i-antigens at the surface of *Ichthyophthirius* elicits a physiological response in the parasite also suggests that these proteins may play a role in transmembrane signaling (T. Clark et al., *Parasitol. Today*, 13:477–480 (1997)). Consistent with this idea, i-antigen antibodies trigger mucocyst discharge in both *I. multifiliis* (T. Clark et al., *J. Fish Biol.*, 31(A):203–208 (1987)) and *Tetrahymena thermophila* (J. Alexander, *Trans. Amer. Microsc. Soc.*, 86:421–427 (1967)), as well as trichocyst discharge in *Paramecium* ssp.

The cDNA sequence associated with a 48 kD i-antigen from an isolate of *I. multifiliis* (G1 isolate, serotype A) was reported by Clark et al. (*Proc. Nat. Acad. Sci. USA*, 89:6363–6367 (1992)); serotyping was reported by Dickerson et al. (*Annu. Rev. Fish Dis.* 6:107–120 (1996)). A recombinant subunit vaccine derived from this cDNA sequence was reported by He et al. (*Aquaculture* 158: 1–10 (1997)). This subunit vaccine was engineered as a recombinant glutathione sulfotransferase (GST) fusion with a 105 amino acid fragment of the protein that the researchers identified as a potential antigenic epitope, corresponding to one of several tandemly repetitive amino acid sequence domains identified by Clark et al. (*Proc. Nat. Acad. Sci. USA*, 89:6363–6367 (1992)). The nucleotide sequence encoding the fusion construct was chemically synthesized and used for expression of the recombinant peptide in bacteria. Two amino acid substitutions relative to the native sequence were required in order to provide restriction sites in the corresponding DNA; moreover, protozoan glutamine codons TAA and TAG (which function as stop codons in *E. coli* and other conventional protein expression systems) were replaced by the universal glutamine codons CAG or CAA in order to allow expression of the fusion construct in *E. coli*. The fusion vaccine gave weak protection against an undefined isolate of *I. multifiliis*; 50% of the vaccinated fish were heavily infected with *I. multifiliis* upon challenge with the live parasite, compared to 75% of control fish.

The 48 kD i-antigen protein has been isolated from cultures of *I. multifiliis* (Clark et al., *Annu. Rev. Fish Dis.* 5:113–131 (1995); Lin et al., *J. Protozoology* 39:457–463 (1992)). In addition, a 55 kD i-antigen protein has been isolated from cultures of *I. multifiliis* and affinity purified and used in studies on passive immunity (T. L. Lin et al., *Inf. Immun.* 64:4085–4090 (1996)). Mouse monoclonal antibodies raised against this protein were effective to immobilize G5 isolates of *I. multifiliis*. However, a native i-antigen protein would be very difficult to obtain from *I. multifiliis* in large quantity because this obligate parasite cannot be easily cultured.

It is clear that an inexpensive and effective vaccine against Ich would be of great benefit to the aquaculture industry.

SUMMARY OF THE INVENTION

The present invention is directed to novel i-antigen polypeptides and nucleic acid molecules that encode them. Examples of novel i-antigen polypeptides include polypeptides having SEQ ID NO:6 and SEQ ID NO:7 derived from *I. multifiliis*. The nucleic acid molecule provided by the invention contains a polynucleotide fragment having a nucleotide sequence that encodes at least a portion of an i-antigen polypeptide, exemplified by nucleotide sequences SEQ ID NOs: 1, 3 and 5. In one embodiment, the polynucleotide fragment encodes at least a C-terminal portion of an i-antigen polypeptide having amino acid sequence SEQ ID NO:6; in another it encodes at least one terminal portion of an i-antigen polypeptide having amino acid sequence SEQ ID NO:7; in yet another it encodes at least an antigenic portion an i-antigen polypeptide having amino acid sequence SEQ ID NO:7. The nucleic acid molecule of the invention can take the form of a vector that is capable of expression in an organism or in a cell, preferably a fish and/or in a conventional protein expression system, including bacteria, such as *E. coli*, yeast, mammalian cell culture or insect cells. The invention includes a host cell transformed with the vector of the invention, and further includes an organism, preferably a fish, comprising a nucleic acid molecule of the invention. Also included is an antibody capable of binding at least one of the i-antigen polypeptides of the invention.

The invention further includes a composition for inducing an immune response in a fish comprising a nucleic acid molecule that has a nucleotide sequence that encodes an antigenic portion of an i-antigen polypeptide of the invention. Likewise, the invention includes a composition for inducing an immune response in a fish comprising an antigenic i-antigen polypeptide of the invention. The invention further includes a method for causing an immune response in the fish by administering an immunogenic composition as described, for example as a prophylactic or therapeutic vaccine. The composition preferably prevents or controls *I. multifiliis* infection in fish.

Also included in the invention is a method for detecting *Ichthyophthirius* in an aquaculture. A sample containing nucleic acid is obtained from an aquaculture fish or from water present in the aquaculture, then at least one primer oligonucleotide having a sequence complementary to at least a portion of SEQ ID NO:6 or SEQ ID NO:7 is added to the nucleic acid sample. A polymerase chain reaction amplification is conducted, and the amplified product is analyzed for the presence of a product amplified by the at least one oligonucleotide primer. Advantageously, the amplified product can then be used to formulate or customize a vaccine effective to treat or prevent *Ichthyophthirius* infection. The method thus optionally includes making a polynucleotide vaccine that contains at least a portion of the amplified product, or a protein subunit vaccine that includes an antigenic polypeptide encoded by the portion of the amplified product; and administering the vaccine to treat or prevent *Ichthyophthirius* infection in a fish or fish population.

Further, the invention provides a method for identifying an *I. multifiliis* serotype. A sample containing *I. multifiliis* nucleic acid is combined with at least one primer oligonucleotide that has a sequence complementary to a region of an *I. multifiliis* nucleotide sequence encoding an i-antigen that is unique to and selective for that serotype, then a polymerase chain reaction amplification is conducted. The reaction mixture is analyzed for the presence of a product amplified by the serotype-selective oligonucleotide primer.

BRIEF DESCRIPTION OF THE FIGURES

FIG. 1 shows the nucleotide sequence (SEQ ID NO:2) and the deduced amino acid sequence (SEQ ID NO:6) of the 48 kD i-antigen gene (IAG48[G1]); a guanine (G) nucleotide that marks the start of the 1.2 kb cDNA is indicated by the arrow; the adenosine (A) nucleotide in the gene's putative ATG start codon for the 48 kD i-antigen is assigned the number +1; a stretch of 14 mostly hydrophobic amino acids at the C-terminus of the deduced protein is boxed; the 3 small amino acids (Cys-Ala-Ser, denoted with asterisks) may represent the site at which cleavage and GPI-anchor addition occurs.

FIG. 2 shows nucleotide sequences for (a) the native G5 55 kD i-antigen coding region including stop codons (SEQ ID NO:44); and (b) a synthetic 55 kD i-antigen coding region, including stop codons (SEQ ID NO:102), useful as a DNA vaccine and in conventional protein expression systems.

FIG. 3 shows (a) an alignment of the deduced amino acid sequences of the genomic 48 kD (upper line) (SEQ ID NO:6) and 55 kD (lower line) (SEQ ID NO:7) i-antigens of *I. multifiliis*; where asterisks indicate identities between the two deduced protein sequences, double dots indicate highly homologous amino acids, and single dots indicate moderately homologous amino acids; boxes indicate conserved regions; and (b) an alignment of the nucleotide sequences of the coding regions of the IAG48 [G1] gene (upper line) (SEQ ID NO:1) and the IAG55[G5] gene (lower line) (SEQ ID NO:3) of *I. multifiliis*, where asterisks indicate identities between the two nucleotide sequences.

FIG. 4 shows the deduced amino acid sequence of the 55 kD i-antigen encoded by the IAG55 [G5] coding region in FIG. 2(a).

FIG. 5 shows an amino acid sequence alignment of five homologous tandemly repeated amino acid sequence domains of (a) the deduced 48 kD i-antigen genomic coding region and (b) the deduced 55 kD i-antigen coding region; amino acids that are shared by three or more repeats are boxed; asterisks denote cysteine residues conserved in all repeats.

FIG. 8 shows an amino acid sequence alignment of *I. multifiliis* and *Giardia* surface proteins; the IAG48[G1] (amino acids 20–428) (SEQ ID NO:61) and *Giardia lamblia* vspA6-S1 (amino acids 61–459) (SEQ ID NO:62) gene products were compared using CLUSTALW multiple sequence alignment software; common cysteine residues are boxed; the segment of the *Giardia* VSP shown here (accession no. Q24970) comprises 67% of the predicted protein.

FIG. 12 lists oligonucleotide primers used for DNA shuffling-based synthesis of a G5 synthetic i-antigen gene.

FIG. 14 shows the amino acid sequence of a synthetic G5 proline mutant i-antigen protein (L6P) (SEQ ID NO:54); the arrow indicates the position of the mutation.

Figure 6:
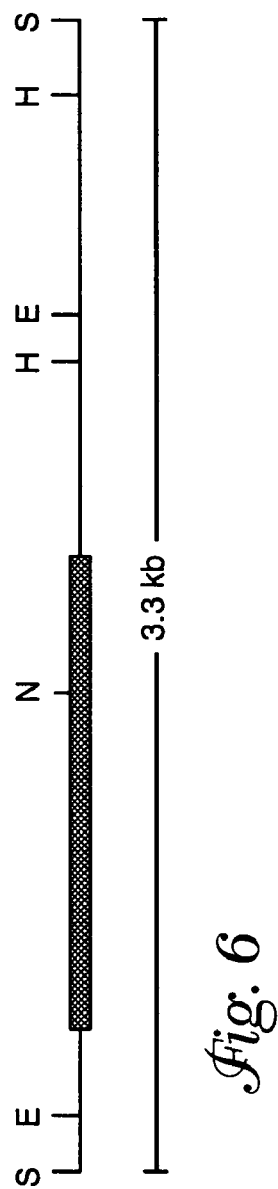
FIG. 6 is a restriction map of the cloned genomic DNA fragment encoding the 48 kD i-antigen; Swa I, (S); EcoR I, (E); Nsi, (N); and Hind III, (H); the filled portion indicates the coding region of the i-antigen gene.

Likewise, the invention includes a nucleic acid molecule comprising a polynucleotide fragment having a nucleotide sequence selected from the class of nucleotide sequences that encodes a polypeptide having at least a terminal portion of amino acid sequence SEQ ID NO:7. Preferably, the polynucleotide is at least about 20 nucleotides in length. A terminal portion of SEQ ID NO:7 can be an N-terminal portion or a C-terminal portion. An "N-terminal portion" of SEQ ID NO:7 includes at least one amino acid that is contiguous to, and located to the N-terminal side of, amino acid 21 (Ala21) in SEQ ID NO:7, and is exemplified by amino acids 1 (Met1) through 20 (Ser20) (SEQ ID NO:15). Preferably, an N-terminal portion of SEQ ID NO:7 includes at least about 6 contiguous amino acids from SEQ ID NO:15, more preferably at least about 10, even more preferably at least about 15. In a particularly preferred embodiment of this aspect of the invention, an N-terminal portion of SEQ ID NO:7 includes the first 20 amino acids of SEQ ID NO:7 (Met-Lys-Asn-Asn-Ile-Leu-Val-Ile-Leu-Ile-Ile-Ser-Leu-Phe-Ile-Asn-Gln-Ile-Lys-Ser, SEQ ID NO:15), which constitutes a novel membrane targeting sequence. A "C-terminal portion" of SEQ ID NO:7 includes at least one amino acid that is contiguous to, and located to the C-terminal side of amino acid 448 (Ile448) in SEQ ID NO:7, and is exemplified by amino acids 449 (Gln449) through 468 (Leu468) (SEQ ID NO:17). Preferably, a C-terminal portion of SEQ ID NO:7 includes at least about 6 contiguous amino acids from SEQ ID NO:17, more preferably at least about 14, even more preferably at least about 20. In a particularly preferred embodiment of this aspect of the invention, a C-terminal portion of SEQ ID NO:7 includes the last 14 amino acids of SEQ ID NO:7 (Phe-Leu-Ser-Ile-Ser-Leu-Leu-Leu-Ile-Ser-Tyr-Tyr-Leu-Leu, SEQ ID NO:16), which represents a novel hydrophobic signaling sequence for targeting to a ciliate membrane; more preferably the C-terminal portion includes the last 20 amino acids of SEQ ID NO:7 (Gln-Cys-Asp-Phe-Ala-Asn-Phe-Leu-Ser-Ile-Ser-Leu-Leu-Leu-Ile-Ser-Tyr-Tyr-Leu-Leu, SEQ ID NO:17).

It is envisioned the N-terminal and C-terminal membrane targeting sequences of SEQ ID NO:7, exemplified by SEQ ID NOs:15–17, can be fused to other proteins and used to direct secretion or membrane surface display of the proteins in other ciliates known to utilize GPI anchors, such as *Tetrahymena* and *Paramecium*. Additionally, the N-terminal membrane targeting sequence may be more generally applicable to other protein expression systems. Conservative substitutions of hydrophobic residues, such as substitutions of leucine, isoleucine, and phenylalanine with each other, are expected to be well tolerated within these signal sequences, and nucleotide sequence encoding SEQ ID Nos: 15–17 that have been modified with one or more of these conservative substitutions are also included in the invention.

Examples of the class of nucleotide sequences that encode a polypeptide having amino acid SEQ ID NO:7 are SEQ ID NOs:3 and 5. This class of nucleotide sequences is likewise large but finite, and the nucleotide sequence of each member of the class can also be readily determined by reference to the standard genetic code, as used in *E. coli*. Additional members of this class of nucleotide sequences, for use in ciliate expression systems, can be determined using the modified genetic code for ciliates, as described herein.

The nucleic acid molecule of the invention can be DNA, RNA, or a combination thereof, and can include any combination of naturally occurring, chemically modified or enzymatically modified nucleotides. The nucleic acid molecule can be equivalent to the polynucleotide fragment encoding an i-antigen protein, or it can include said polynucleotide fragment in addition to one or more additional nucleotides or polynucleotides. For example, the nucleic acid molecule of the invention can be a vector, such as an expression or cloning vector. A vector useful in the present invention can be circular or linear, single-stranded or double stranded, and can include DNA, RNA, or any modification or combination thereof. The vector can be a plasmid, a cosmid, or a viral vector, such as baculovirus. Preferably, the nucleic acid molecule of the invention takes the form of an expression vector that is capable of expression in an organism or in a cell of the organism, in culture or in vivo. An organism or cell in which the coding sequence of the vector can be expressed can be eukaryotic or prokaryotic, and can be, without limitation, a bacterium, a yeast, an insect, a protozoan, preferably a ciliate such as *Tetrahymena*, or animal, such as a fish or a mammal. Preferably, the vector is expressible in a fish and/or in a conventional protein expression system, including bacteria, such as *E. coli*, yeast, such as *Pischia pastoris*, mammalian cell culture or insect cells.

When the vector is intended for use in bacterial, yeast, mammalian or insect expression systems, the coding sequences of the vector are preferably engineered to utilized the conventional genetic code rather than the ciliate genetic code that is employed in the native *I. multifiliis* coding sequences. Thus, in preferred embodiments of these aspects of the invention, the nucleotide sequence of the polynucleotide fragment that encodes an i-antigen protein is altered such that each ciliate glutamine codon TAA and TAG in the nucleotide sequence derived from the *I. multifiliis* isolate is replaced with a universal glutamine codons, either CAG or CAA. Accordingly, a particularly preferred embodiment of the nucleic acid molecule of the invention includes a polynucleotide fragment having SEQ ID NO:5.

It should be understood that the nucleic acid molecule of the invention can be single-stranded or double-stranded, and further that a single-stranded nucleic acid molecule of the invention includes a polynucleotide fragment having a nucleotide sequence that is complementary to a nucleotide sequence that encodes an i-antigen protein or portion thereof according to the invention. As used herein, the term "complementary" refers to the ability of two single stranded polynucleotide fragments to base pair with each other, in which an adenine on one nucleic acid fragment will base pair to a thymine on the other, and a cytosine on one nucleic acid fragment will base pair to a guanine on the other. Two polynucleotide fragments are complementary to each other when a nucleotide sequence in one nucleic acid fragment can base pair with a nucleotide sequence in a second nucleic acid fragment. For instance, 5'-ATGC and 5'-GCAT are fully complementary, as are 5'-ATGC and 5'-GCAT.

Further, the single-stranded nucleic acid molecule of the invention also includes a polynucleotide fragment having a nucleotide sequence that is substantially complementary to a nucleotide sequence that encodes an i-antigen protein or portion thereof according to the invention, or to the complement of the nucleotide sequence that encodes an i-antigen or portion thereof. Substantially complementary polynucleotide fragments can include at least one base pair mismatch, such that at least one nucleotide present on a first polynucleotide fragment will not base pair to at least one nucleotide present on a second polynucleotide fragment, however the two polynucleotide fragments will still have the capacity to hybridize. For instance the middle nucleotide of each of the two DNA fragments 5'-AGCAAATAT and 5'-ATATATGCT will not base pair, but these two nucleic acid fragments are nonetheless substantially complementary as defined herein. Two polynucleotide fragments are substantially complementary if they hybridize under hybridization conditions exemplified by 2×SSC (SSC: 150 mM NaCl, 15 mM trisodium citrate, pH 7.6) at 55° C. Substantially complementary polynucleotide fragments for purposes of the present invention preferably share at least one region of at least about 50 nucleotides in length, which shared region has at least about 85% nucleotide identity, preferably at least about 90% nucleotide identity. More preferably, substantially complementary polynucleotide fragments share a plurality of regions of between about 50 nucleotides and about 150 nucleotides in length, which shared regions have at least about 85% nucleotide identity, preferably at least about 90% nucleotide identity. In a particularly preferred embodiment, the substantially complementary nucleotide sequence encodes at least one of SEQ ID NOs:90–100 as shown on FIG. 3(a). Locations and levels of nucleotide sequence identity between two nucleotide sequences can be readily determined using CLUSTALW multiple sequence alignment software.

The invention further includes a nucleic acid molecule comprising a polynucleotide fragment that hybridizes to at least a portion of the complement of either or both of SEQ ID NO:1 or SEQ ID NO:3, under standard hybridization conditions, provided that the polynucleotide fragment encodes a polypeptide comprising at least a membrane targeting portion or an antigenic portion of an i-antigen protein. A membrane targeting portion of an i-antigen protein is one that targets the polypeptide to either the endoplasmic recticulum (e.g., an N-terminal signal sequence) or to the plasma membrane (e.g., a GPI anchor sequence). Standard hybridization conditions are exemplified by 2×SSC(SSC: 150 mM NaCl, 15 mM trisodium citrate, pH 7.6) at 55° C.

The invention further includes a nucleotide molecule comprising a polynucleotide fragment encoding an antigenic analog or modification of a polypeptide represented by SEQ ID NO:6, or an antigenic fragment thereof that includes at least a C-terminal portion of SEQ ID NO:6; further, the invention includes a nucleotide molecule comprising a polynucleotide fragment encoding an antigenic analog, fragment, or modification of a polypeptide represented by SEQ ID NO:7, as described in more detail below.

Figure 1:
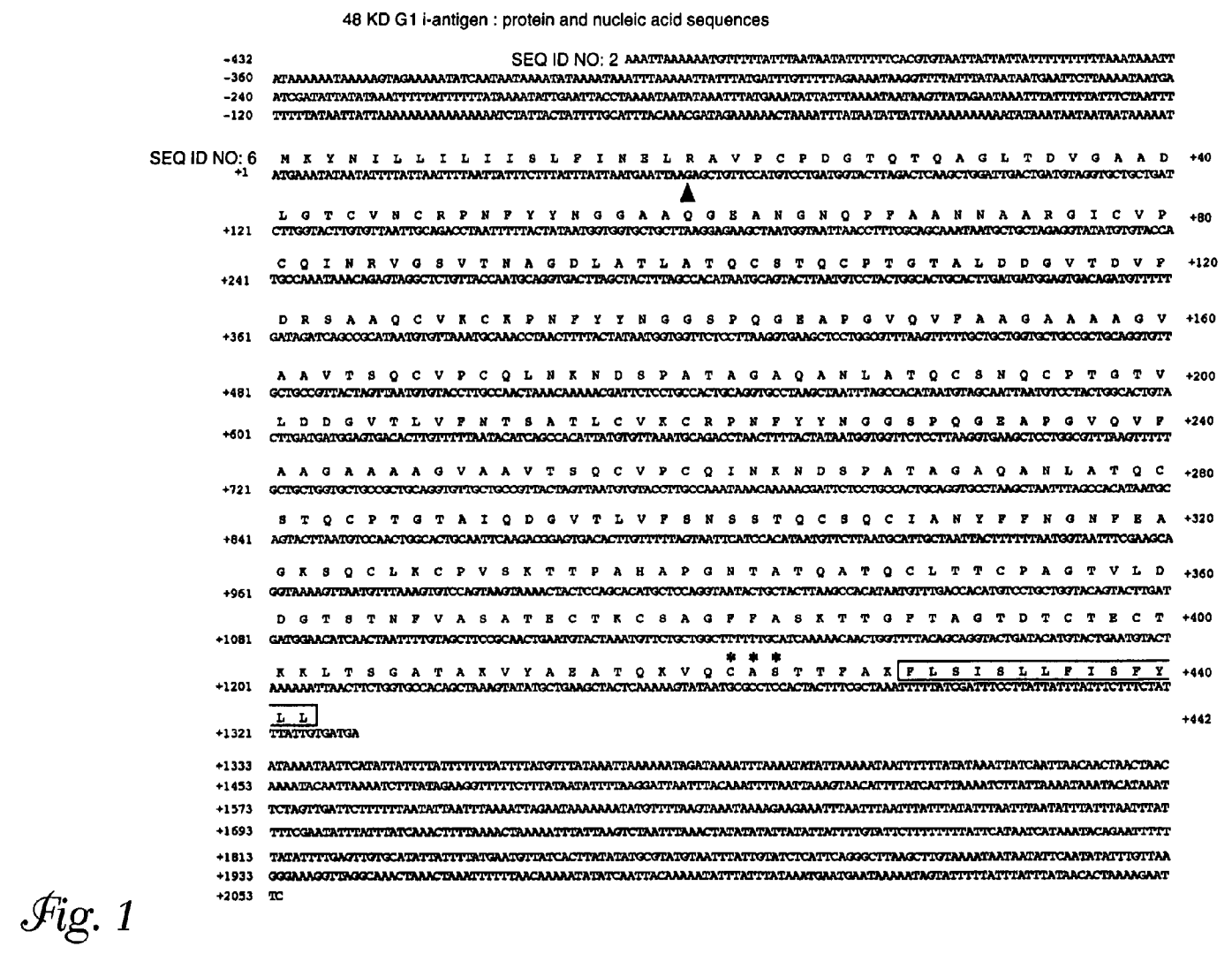
Figure 3B:
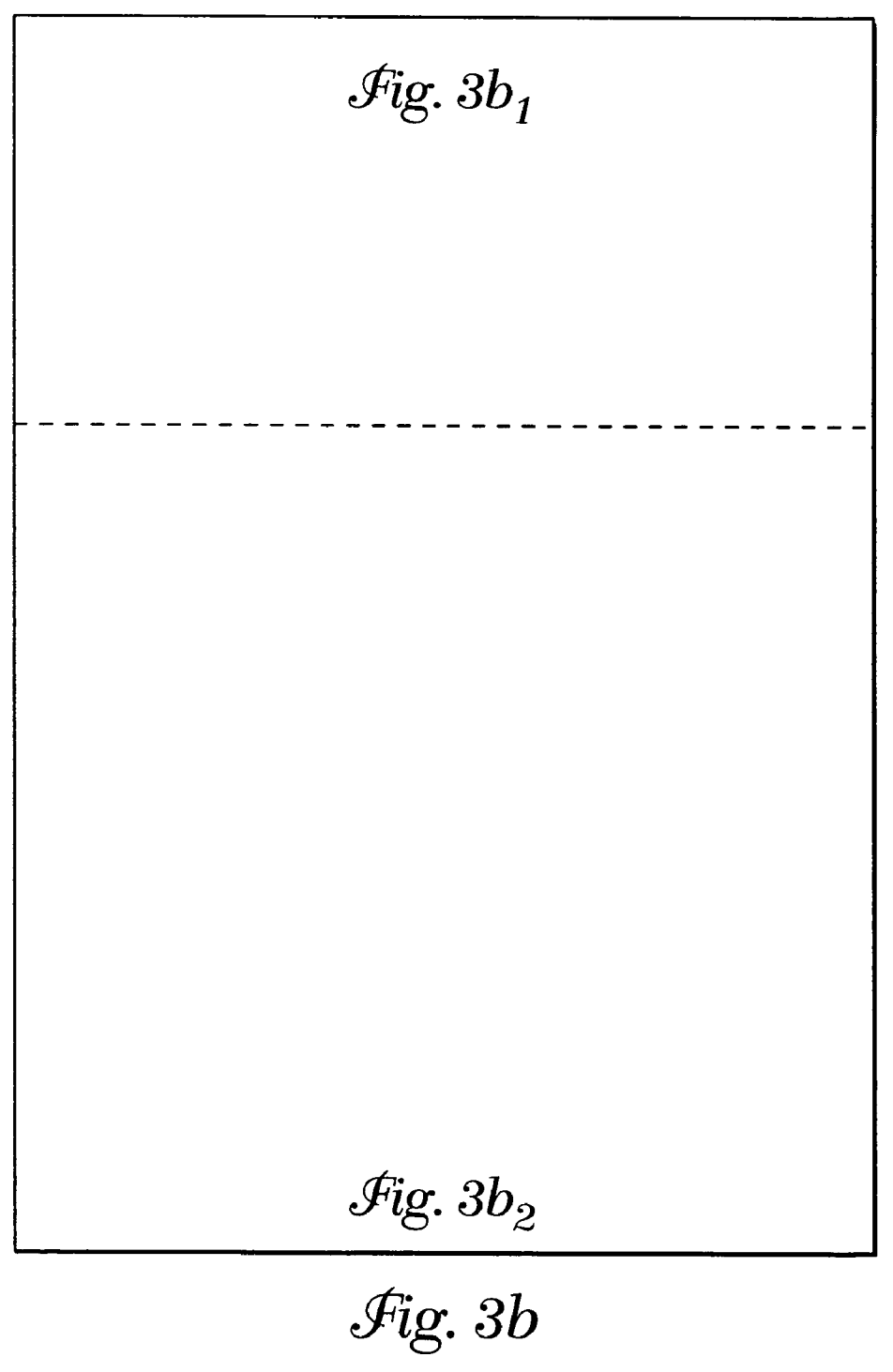

Also provided by the invention is a novel i-antigen protein. In a further aspect of the invention, therefore, the i-antigen protein is encoded by a nucleotide sequence derived from *I. multifiliis* (G1 isolate), and has a molecular weight of about 48 kD. In a particularly preferred embodiment of this aspect of the invention, the i-antigen protein is encoded by the nucleotide sequence as shown in FIG. 3(b), nucleotides 1 through 1326 (SEQ ID NO:1), representing the coding region of the IAG48[G1]gene of *I. multifiliis*, and has the amino acid sequence SEQ ID NO:6 (FIG. 1). In another aspect of the invention, the i-antigen protein is encoded by a nucleotide sequence derived from *I. multifiliis* (G5 isolate), and has a molecular weight of about 55 kD. In a particularly preferred embodiment of this aspect of the invention, the i-antigen is encoded by the nucleotide sequence as shown in FIG. 2(a), nucleotides 1 through 1404 (SEQ ID NO:3), representing the coding region of the IAG55[G5] gene, and has the amino acid sequence SEQ ID NO:7 (FIG. 4).

The i-antigen polypeptide of the invention includes an i-antigen polypeptide having SEQ ID NO:6; an i-antigen polypeptide having SEQ ID NO:7; an analog or modification of an i-antigen polypeptide having SEQ ID NO:6; a fragment of an i-antigen polypeptide having SEQ ID NO:6 having at least a C-terminal portion of SEQ ID NO:6; an antigenic analog, fragment, or modification of an i-antigen polypeptide having SEQ ID NO:7; and an analog, fragment, or modification of an i-antigen polypeptide having SEQ ID NO:7 wherein said analog, fragment or modification has at least one terminal portion of SEQ ID NO:7.

An antigenic analog, fragment, or modification of a polypeptide having SEQ ID NOs:6 or 7 is one that generates an immune response in fish against *I. multifiliis*. Antigenicity of an polypeptide can be evaluated in vitro by performing a Western blot on the purified polypeptide (for example, an affinity purified polypeptide) using polyclonal antisera from a rabbit that was vaccinated with at least an antigenic portion of a native *I. multifiliis* i-antigen protein, preferably with a complete *I. multifiliis* i-antigen protein (e.g., SEQ ID NO:6 or SEQ ID NO:7).

Antigenic analogs of polypeptide having SEQ ID NO:6, SEQ ID NO:7 include i-antigen polypeptides having amino acid substitutions that do not eliminate polypeptide antigenicity in fish. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Fragments of an i-antigen polypeptide of the invention include i-antigen polypeptides containing deletions or additions of one or more contiguous or noncontiguous amino acids that do not eliminate the antigenicity of the i-antigen in fish are also contemplated. Fragments of an i-antigen polypeptide contain at least about six amino acids, preferably at least about 10 amino acids, more preferably at least about 60 amino acids. Modified i-antigens include i-antigens that are chemically and enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

The invention further includes an antigenic polypeptide that shares a significant level of primary structure with either or both of SEQ ID NO:6 or SEQ ID NO:7. Preferably, the antigenic polypeptide of this aspect of the invention is a synthetic polypeptide. A synthetic polypeptide is one that does not have the amino acid sequence of a polypeptide that is isolated from an organism; i.e., it is not a naturally occurring polypeptide. An antigenic polypeptide shares a significant level of primary structure with either or both of SEQ ID NO:6 or SEQ ID NO:7 if it has a plurality of amino acid sequence domains, each domain having about 60 to about 100 amino acids, of which six are cysteines that fall into register when the sequence domains are aligned with the amino acid sequence domains of SEQ ID NOs:6 or 7, as exemplified in FIG. 5. The predominant primary structure motif in an antigenic polypeptide of the invention is -Cys-$Xaa_{2,3}$-Cys- (SEQ ID NOs:31, 32), where Xaa is any amino acid, and where $Xaa_{2,3}$ means $Xaa_2$ or $Xaa_3$, that is, where pairs of cysteines are separated by two or three amino acids. Preferably, the antigenic polypeptide of the invention has larger scale repeating motifs characterized by -Cys-Xaa$_2$-Cys-Xaa$_m$-Cys-Xaa$_3$-Cys-Xaa$_n$-Cys-Xaa$_2$-Cys- where m=15–25, preferably 20–22, and n=15–25, preferably 19–20 (e.g., SEQ ID NO:33 where m=20, n=20). More preferably, the larger scale repeating motifs are characterized by -Cys-Xaa$_2$-Cys-Xaa$_m$-Cys-Xaa$_3$-Cys-Pro-Xaa$_p$-Cys-Xaa$_2$-Cys- where m=15–25, preferably 20–22 and p=14–24, preferably 18–19 (e.g., SEQ ID NO:88 where m=20, p=18). In a particularly preferred embodiment, the larger scale repeating motifs are characterized by -Cys-Xaa$_2$-Cys-Xaa$_q$-Gln-Cys-Xaa$_3$-Cys-Pro-Xaa-Gly-Thr-Xaa$_r$-Cys-Xaa$_2$-Cys-, where q=14–24, preferably 19–21, and r=11–21, preferably 15–16 (e.g., SEQ ID NO:89 where q=20, r=20). In a particularly preferred embodiment of the invention, each amino acid sequence domain of an antigenic polypeptide of the invention has at least 90% amino acid identity with at least one of SEQ ID NOs:8–12 (FIG. 5(a)) and 55–60 (FIG. 5(b)); most preferably, each amino acid sequence domain of an antigenic polypeptide of the invention has at least 95% amino acid identity with at least one of SEQ ID NOs:8–12 and 55–60 (FIG. 5).

The location and level of amino acid sequence identity between two amino acid sequences can be readily determined using CLUSTALW multiple sequence alignment software. Alternatively, the two amino acid sequences (i.e., the amino acid sequence of the candidate domain sequence of the antigenic polypeptide and the reference amino acid sequence selected from SEQ ID NOs:8–12 and 55–60) are aligned such that the cysteines are in register, then further aligned to maximize the number of amino acids that they have in common along the lengths of their sequences; gaps in either or both sequences are permitted in making the alignment in order to place the cysteines in register and to maximize the number of shared amino acids, although the amino acids in each sequence must nonetheless remain in their proper order. The percentage amino acid identity is the higher of the following two numbers: (a) the number of amino acids that the two sequences have in common within the alignment, divided by the number of amino acids in the reference sequence, multiplied by 100; or (b) the number of amino acids that the two sequences have in common within the alignment, divided by the number of amino acids in the candidate polypeptide, multiplied by 100.

The invention further includes a polypeptide having a membrane targeting sequence selected from a C-terminal portion of SEQ ID NO:6, an N-terminal portion of SEQ ID NO:7, and a C-terminal portion of SEQ ID NO:7, as described above.

The present invention further provides a vaccine for use in preventing or controlling disease in fish caused by *I. multifiliis*. The polynucleotide vaccine comprises a polynucleotide fragment, preferably a DNA fragment, having a nucleotide sequence encoding an antigenic polypeptide comprising at least an antigenic portion of an i-antigen protein derived from *I. multifiliis*. The polynucleotide vaccine optionally further comprises a promoter, preferably the CMV promoter, operably linked to the coding sequence for the i-antigen polypeptide (e.g., U.S. Pat. No. 5,780,448, Davis). There are numerous plasmids known to those of ordinary skill in the art useful for the production of polynucleotide vaccines. A specific embodiment employs constructs using the plasmid pcDNA3.1 as the vector (InVitrogen Corporation, Carlsbad, Calif.). In addition, the vector construct can contain immunostimulatory sequences (ISS), such as unmethylated dCpG motifs, that stimulate the animal's immune system. Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to affect the animal's reproductive system. The polynucleotide vaccine can also encode a fusion product containing the antigenic polypeptide and a molecule, such as CTLA-4, that directs the fusion product to antigen-presenting cells inside the host. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell. An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella, Edwardsiella ictaluri*, and *Yersinia ruckeri*. Preferably, the polynucleotide is a vector, such as a plasmid, that is capable of autologous expression of the nucleotide sequence encoding an i-antigen.

In a particularly preferred embodiment, the vaccine is a DNA vaccine comprising a DNA fragment having a nucleotide sequence that encodes a polypeptide having amino acid sequence SEQ ID NO:6 or SEQ ID NO:7, an antigenic analog, fragment, or modification of a polypeptide having SEQ ID NO:7, an antigenic analog or modification of a polypeptide having SEQ ID NO:6, or an antigenic fragment of a polypeptide having SEQ ID NO:6 provided that the fragment includes at least a C-terminal portion of SEQ ID NO:6. An antigenic analog, fragment, or modification of an i-antigen polypeptide is one that generates an immune response in fish against *I. multifiliis*. For example, a preferred DNA vaccine comprises a DNA fragment having a nucleotide sequence encoding an amino acid sequence selected from the group consisting of SEQ ID NOs:8–12 and 55–60; these eleven amino acid sequences represent tandemly repeated amino acid sequence domains found in the deduced amino acid sequence SEQ ID NO:6 and are expected to be antigenic. More preferably, the DNA vaccine comprises all or a portion of nucleotide sequence SEQ ID NO:1, SEQ ID NO:3 or SEQ ID NO:5, provided that the portion of SEQ ID NO:1, SEQ ID NO:3 or SEQ ID NO:5 encodes an antigenic polypeptide and further provided that, in SEQ ID NO:1 and SEQ ID NO:3 codons TAA and TAG that code for glutamine in *I. multifiliis* are changed to CAG or CAA. Most preferably, the DNA vaccine includes a synthetic DNA fragment having a nucleotide sequence that encodes a polypeptide SEQ ID NOs:6 or 7 using codons that are biased in favor of the host's codon usage.

Polynucleotide-based immunization induces an immune response to an antigen expressed in vivo from a heterologous polynucleotide fragment introduced into the fish. This method can be advantageous over other methods because heterologous nucleic acid expression may continue for a length of time sufficient to induce a relatively strong and sustained immune response without the need for subsequent "booster" vaccinations, as is common when portions of the protein antigen itself have been injected into the animal. A polynucleotide vaccine comprising a polynucleotide fragment having a nucleotide sequence encoding an i-antigen protein can be administered to a fish using biolistic bombardment, bath immersion, ingestion or direct injection, as described in U.S. Pat. No. 5,780,448 (Davis), preferably intraperitoneal or intramuscular injection. A preferred method of administration is biolistic bombardment, as with a "gene gun." A polynucleotide vaccine formulated for oral administration preferably contains DNA encapsulated in a biodegradable polymer. Examples of a suitable biodegradable polymer include chitosan and homo- or co-polymers of polylactic acid and polyglycolic acid. The invention thus further provides a method for immunizing freshwater fish against *I. multifiliis* by administering to the fish a polynucleotide vaccine of the invention, preferably a DNA vaccine.

The amount of polynucleotide vaccine to be administered to an animal depends on the type and size of animal, the condition being treated, and the nature of the polynucleotide, and can be readily determined by one of skill in the art. In fish, for example, if the polynucleotide vaccine is to be injected, the amount per injection is preferably at least about 10 ng; at most it is preferably about 50 µg, more preferably it is less than about 1 µg. If the polynucleotide vaccine is to be administered using a gene gun, the amount per dose is preferably at least about 1 ng; at most it is preferably about 10 µg, more preferably it is less than about 1 µg. For administration by immersion, the concentration of the polynucleotide in the aquatic medium is preferably at least about 10 ng/mL; at most it is preferably about 50 µg/mL, preferably it is less than about 1 µg/mL. For oral administration the amount per dose is preferably at least about 10 µg; at most it is preferably about 10 µg, preferably less than about 1 µg. In some applications, one or more booster administrations of the vaccine at time periods subsequent to the initial administration are useful to create a higher level of immune response in the animal.

In another aspect, the vaccine of the invention comprises an i-antigen polypeptide having amino acid sequence SEQ ID NO:6 or SEQ ID NO:7, an antigenic analog, fragment, or modification of a polypeptide having SEQ ID NO:7, an antigenic analog or modification of a polypeptide having SEQ ID NO:6, or an antigenic fragment of a polypeptide having SEQ ID NO:6 provided that the fragment includes at least a C-terminal portion of SEQ ID NO:6. This type of vaccine is referred to herein as a "protein subunit vaccine" even if it contains the entire i-antigen sequence. The i-antigen or antigenic analog, fragment, or modification thereof for use in the protein subunit vaccine of the invention can be naturally occurring (i.e., isolated from *I. multifiliis*) or recombinant. A protein subunit vaccine of the invention are conveniently administered to fish using bath immersion, ingestion, topical administration, or direct injection, preferably intraperitoneal or intramuscular injection. A protein subunit vaccine formulated for oral administration preferably contains polypeptide encapsulated in a biodegradable polymer as described above in connection with the polynucleotide vaccine of the invention. In addition, the protein subunit vaccine can be administered to an animal via a live vector, such as recombinant *Tetrahymena*. *Tetrahymena* can be transformed such that it expresses the i-antigen or antigenic analog, fragment, or modification thereof, either in the cytosol, as a transmembrane protein, as a GPI-anchored protein or as a secreted protein. Recombinant *Tetrahymena* can be injected into the animal or, in the case of an aquatic animal such as a fish, can be administered via immersion. Oral administration of *Tetrahymena* if also envisioned. The invention thus further provides a method for immunizing freshwater fish against *I. multifiliis* by administering to the fish a protein subunit vaccine of the invention.

The amount of protein subunit vaccine to be administered to an animal depends on the type and size of animal, the condition being treated, and the nature of the protein, and can be readily determined by one of skill in the art. In fish, for example, if the protein subunit vaccine is to be injected, the amount per injection is preferably between about 0.1 µg and about 1000 µg per 10 g fish; more preferably it is between about 1 µg and about 100 µg per 10 g of fish. For administration by immersion, the concentration of the protein in the aquatic medium is preferably at least about 10 ng/mL; at most it is preferably about 50 µg/mL, preferably it is less than about 1 µg/mL. For oral administration the amount per dose is preferably between about 0.1 µg and about 100 µg per 10 g fish; more preferably it is between about 1 µg and about 10 µg per 10 g of fish. Preferably, the protein subunit vaccine also includes an adjuvant. Further, one or more boosters are preferably administered at time periods subsequent to the initial administration to create a higher level of immune response in the animal.

In yet another aspect, the vaccine of the invention comprises a fusion protein comprising a carrier polypeptide and an i-antigen polypeptide of the invention or an analog, fragment, or modification thereof. An i-antigen analog, fragment, or modified i-antigen for use in this aspect of the invention can itself be antigenic or nonantigenic; in embodiments wherein the i-antigen analog, fragment or modified i-antigen is nonantigenic, the carrier polypeptide provides the necessary antigenicity by stimulating the fish's immune system to react to the fusion protein thereby generating an immune response in fish against *I. multifiliis*. A nonantigenic analog, fragment, or modification of the i-antigen thus function as a hapten. An example of an antigenic carrier polypeptide is KLH. Conventional fusion constructs between carriers such as glutathione sulfotransferase (GST) and i-antigens of the invention or antigenic analog, fragment, or modifications thereof are also included as protein subunit vaccines according to the invention, as are fusions of the i-antigen and an affinity tag such as a polyhistidine sequence. A fusion construct may be preferred for use as a protein subunit vaccine when the antigenic i-antigen analog, fragment, or modification thereof is small. The invention further provides a method for immunizing freshwater fish against *I. multifiliis* by administering to the fish a fusion protein vaccine of the invention.

Monoclonal antibodies that recognize immobilizing epitopes on i-antigens are protective in passive immunization experiments, but their activity is serotype-specific. On the other hand, fish that are actively immune following exposure to one serotype are cross-protected against heterologous strains. Thus, in one embodiment, the vaccine of the invention (whether in the form of a protein vaccine or a polynucleotide vaccine) is monovalent in that it is derived from a particular i-antigen from a particular serotype of *I. multifiliis* and effective to treat or prevent infection of the vaccinated animal by that serotype. Preferably, the monovalent vaccine contains at least one antigenic determinant that is shared by i-antigens of different serotypes, such that it also prevents infection by other *I. multifiliis* of other serotypes, thus offering broad protection. In another embodiment, the vaccine of the invention (whether in the form of a protein vaccine or a polynucleotide vaccine) is a combined vaccine or a multivalent vaccine that prevents infection by other *I. multifiliis* of more than one serotype. The combined or multivalent vaccine can contain or encode, for example, a plurality of serotype-specific i-antigen polypeptides or antigenic portions thereof, derived from multiple serotypes of *I. multifiliis*, or can contain or encode a synthetic or fusion i-antigen polypeptide containing multiple antigenic determinants that together generate an immune response against multiple serotypes of *I. multifiliis*.

In a preferred embodiment of the vaccine of the invention, i-antigen or an antigenic portion thereof is linked at its carboxy-terminus to at least two molecules of the C3d component of complement, using molecular cloning techniques. Preferably, the i-antigen or antigenic portion thereof is linked to about three molecules of the C3d component of complement. The C3d molecule can be either homologous or heterologous with respect to the species to be vaccinated. Complement genes have been cloned and characterized in salmonids (J. Lambris et al., *J. Immunol.* 151:6123 6134 (1993); J. Sunyer et al., *Proc. Natl. Acad. Sci USA* 93:8546 8551 (1996)). For vaccinations of fish, the i-antigen or antigenic portion thereof is preferably linked to a salmonid C3d, such as trout C3d or catfish C3d. In the case of a protein subunit vaccine, the recombinant protein is conveniently expressed in bacteria, then administered to fish. This technique has been shown to generate in increase in the immune response in mice (P. Dempsey et al., *Science* 271:348–350 (1996)). The receptor for C3d, namely CD21, is expressed primarily on B cells and the follicular dendritic cells of lymphoid tissues. In the case of a polynucleotide vaccine, a plasmid encoding a fusion protein that incorporates an i-antigen or antigenic portion thereof, linked at its carboxy-terminus to at least two molecules of the C3d component, is administered to the fish.

The active immune-stimulating ingredients are optionally mixed with excipients or diluents that are pharmaceutically acceptable as carriers and compatible with the active ingredient. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the immune-stimulating composition (including vaccine) may contain minor amounts of auxiliary substances such as wetting or emulsifying agents, pH buffering agents, and/or adjuvants which enhance the effectiveness of the immune-stimulating composition.

Fish that can be vaccinated against Ich infection include freshwater teleosts, preferably fish that are widely farmed in aquaculture including channel catfish, trout, salmon, tilapia and eels. The goal of vaccination against Ich infection is to elicit a population of lymphocytes, which upon subsequent exposure to the parasite proliferate and produce antibodies and/or effector cells specific to the parasite, resulting in protection against lethal infections. A vaccine effective for the prevention of Ich infection in freshwater fish is thus one which elicits the production of protective antibodies in a fish exposed to said vaccine. Those protective antibodies will prevent lethal infection of the vaccinated fish upon challenge with *I. multifiliis*. In the present invention, protective antibodies generated in the fish are specific for *I. multifiliis* i-antigens. Fish that can be immunized include ornamental and food fish.

The present invention further includes monoclonal or polyclonal antibodies, whether derived from fish, rodents, mammals, avians, or other organisms, that bind to the i-antigen proteins described herein, including antigenic analogs, fragments and modifications thereof. Production and isolation of monoclonal and polyclonal antibodies to a selected polypeptide sequence is routine in the art.

Sera from immune fish is known to confer passive immunity against both viral and bacterial pathogens when injected into non-immune fish (Hedrick et al. *Trans. Amer. Fish Soc.* 116:277 281 (1987); Viele et al. *J. Fish Biol.* 17:379 386 (1980)). We have carried out similar experiments in which mouse monoclonal antibodies specific for Ich i-antigen(s) of the A and D serotypes were transferred into non-immune 10–15 g catfish fingerlings. Monoclonal antibodies which have the ability to immobilize these serotypes in vitro conferred passive protection against the parasite in vivo. Fish weighing 10–15 g were injected intraperitoneally with 20–200 µg of purified mouse monoclonal antibody (MAb) and challenged with infective theronts after 24 hours. A serotype (G1-specific) MAbs included 10H3, 3H12, 8E11, 6A11 and 5A8; D serotype (G5 and G3-specific) MAbs included G3-27 and G3-61. Animals injected with immobilizing MAbs survived lethal infection while controls were completely overwhelmed. The passive protection achieved in the channel catfish model supports the use of i-antigen protein(s) as vaccines for eliciting active immunity (Lin et al., Inf. Immun. 64:4085–4090 (1996); see also He et al. (*Aquaculture* 158:1–10 (1997)).

Comparison of newly discovered amino acid sequences SEQ ID NO:6 (the G1 *I. multifiliis* isolate) and SEQ ID NO:7 (the G5 *I. multifiliis* isolate) shows regions of amino acid identity that were heretofore unknown and unpredictable, because the sequence of only one *I. multifiliis* i-antigen (i.e., the sequence encoded by the cDNA for the 48 kD protein, Clark et al. (*Proc. Nat. Acad. Sci. USA*, 89:6363–6367 (1992) was known. FIG. 3(*a*) shows regions of identity or high homology, which are boxed. It is expected that an oligonucleotide probe or primer having a sequence that encodes a conserved region of the i-antigens as identified herein will be useful for identifying additional i-antigens in *I. multifiliis* having other serotypes; molecular methods for constructing these probes and primers and using them to screen genomic libraries are routine in the art. For example, amino acid sequences at the N and C-termini are highly conserved (see FIG. 3(*a*)). The corresponding regions of the genes would likely serve as sites for the design of diagnostic PCR primers that could be used to amplify i-antigen sequences from any parasite isolate. Moreover, using mouse monoclonal antibodies against the i-antigens, we have been able to define differences between parasite isolates, and have shown that protection following passive antibody transfer is strain (i.e., isolate) specific. Thus, the identification of additional i-antigens using nucleotide probes and primers derived from conserved regions as described herein will likely provide amino acid and nucleotide sequence information that allows the production of additional serotype-specific i-antigen DNA and protein subunit vaccines.

Accordingly, the invention further provides for an oligonucleotide probe or primer (including its complement) having a nucleotide sequence encoding at least a portion of an i-antigen conserved region as shown in FIG. 3(*a*) (boxed regions). Preferably, the oligonucleotide probes or primers are represented by nucleotide sequences that encode conserved *I. multifiliis* i-antigen regions of at least about eight amino acids in length, which conserved regions are selected from portions of SEQ ID NOs:90–100 (FIG. 3(*a*)) that contain at least about eight amino acids. More preferably, the oligonucleotide probes or primers are represented by the sequences MKYNILLT (SEQ ID NO:36), FLSISLLF (SEQ ID NO:38), GTALDDGV (SEQ ID NO:46), AGTDTCT (SEQ ID NO:48), CTKKLTSGA (SEQ ID NO:50) and FAKFLSISL (SEQ ID NO:52). Further, the invention provides a method for identifying i-antigens in *I. multifiliis* by using the oligonucleotide probe or primer of the invention to identify and isolate novel nucleotide sequences encoding other i-antigens, for example by probing a genomic DNA or cDNA library of an isolate of *I. multifiliis* or by conducting polymerase chain reaction. Vaccines that utilize the nucleotide and amino acid sequences of the i-antigens so discovered, which as a result are effective against other serotypic variants of *I. multifiliis*, are also provided.

Knowledge of the i-antigen nucleotide and amino acid sequences set forth herein also opens up new possibilities for detecting, diagnosing and characterizing *Ichthyophthirius* in fish populations. For example, an oligonucleotide probe or primer based on a conserved region of the i-antigen protein can be used to detect the presence of *Ichthyophthirius* in a fish or in water, and an oligonucleotide probe or primer based on a less conserved region can be used to identify a specific *Ichthyophthirius* serotype. The invention therefore includes methods for detecting and characterizing *Ichthyophthirius*, for example in aquaculture facilities.

Recombinant Expression of I-antigens

As already noted, the principal difficulty associated with making a vaccine against *I. multifiliis* is the fact that this obligate parasite cannot be easily cultured. Thus, production of i-antigen in an recombinant system is highly desirable. Ciliated protozoans, however, including *Ichthyophthirius*, utilize TAA and TAG as codons for the amino acid glutamine, while most other organisms recognize those as termination codons. Therefore, according to the invention, either the native nucleotide sequence is expressed in a ciliated protozoan, or the native nucleotide sequence is altered to use a universal glutamine codon (either CAG or CAA) in place of any TAA and TAG triplets used in the native sequence.

Bacterial expression systems. Selection of a vector or plasmid backbone depends upon a variety of desired characteristics in the resulting construct, such as a selection marker, plasmid reproduction rate, and the like. Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK223-3 pKK233-2 and pTrc99A can be obtained from Pharmacia Biotech. pET-(X) vectors can be obtained from Promega (Madison, Wis.) Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

The expression vector optionally includes a promoter sequence operably linked to the nucleotide sequence encoding i-antigen protein. A promoter is a DNA fragment which causes transcription of genetic material. Transcription is the formation of an RNA chain in accordance with the genetic information contained in the DNA. The invention is not limited by the use of any particular promoter, and a wide variety are known. Promoters act as regulatory signals that bind RNA polymerase in a cell to initiate transcription of a downstream (3' direction) coding sequence. A promoter is "operably linked" to a nucleic acid sequence if it does, or can be used to, control or regulate transcription of that nucleic acid sequence. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

The nucleotide sequence encoding the i-antigen protein can advantageously be fused, at either the 5' or 3' end, to a nucleotide sequence encoding an affinity tag, such as a polyhistidine amino acid sequence. The resulting fusion construct can be conveniently purified using the affinity tag for subsequent use. Affinity tags and methods for protein purification using affinity tags are well-known in the art. Optionally, a cleavage site, such as a Factor X cleavage site, can be introduced between the affinity tag and the amino acid sequence of the i-antigen to facilitate large-scale preparation of the i-antigen protein free of the carrier polypeptide.

The expression vector optionally includes a Shine Dalgarno site (i.e., a ribosome binding site), and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The nucleic acid fragment used to transform the host cell can optionally further include a transcription termination sequence. The rrnB terminators, which is a stretch of DNA that contains two terminators, T1 and T2, is the most commonly used terminator that is incorporated into bacterial expression systems (J. Brosius et al., *J. Mol. Biol.* 148: 107–127 (1981)).

The TAA and TAG codons in the native coding sequence of the i-antigen can be substituted with conventional glutamine codons either by site-directed mutagenesis (see e.g., Sambrook et al. (1989) *Molecular Cloning*, Second Edition, Cold Spring Harbor Laboratory Press, Plainview, N.Y.) or by creating a synthetic coding sequence using chemical synthesis of the desired coding sequence. Manual DNA synthetic techniques are well known (see, e.g., Caruthers (1983) *Methods in of DNA and RNA Sequencing*, Weissman (ed.), Praeger Publishers, New York, Chapter 1), as is automated DNA synthesis using any of several commercially available systems.

An alternative strategy is to express the i-antigen coding sequence with the UAA and UAG glutamine codons in a suppressor strain of *E. coli*. Cohen et al. (*J. Molec. Biol.* 216:189–194 (1990)) has reported a plasmid vector (pAD205) which provides an inducible suppressor tRNA which recognizes UAA and UAG codons and which is charged with glutamic acid. The plasmid pAD205 contains the gene encoding the artificial suppressor tRNA$^{glu}$ su oc205, previously described by Raftery et al. (EMBO J. 6:1499–1506 (1987)) which gene is expressed in pAD205 under the regulatory control of an isopropyl-β-D-thiogalactopyranoside (IPTG)-inducible tac promoter. IPTG induces the expression of the tRNAs and thus allows the readthrough of UAG and UAA stop codons. Basal levels of the suppressor tRNAs are kept low by the presence of a leaky transcription termination signal between the promoter and the tRNA gene to minimize potentially lethal effects on the cells. J. Cohen et al. (*J. Mol. Biol.* 216:189 194 (1990)) reported the expression of a *Paramecium* tubulin gene in *E. coli* using this vector.

Eukaryotic expression systems. The insect baculovirus vector, *Autographa californica*, is capable of high level expression of foreign gene inserts and posttranslational modifications (see, e.g., International Patent Publication WO 90/14428). In terms of qualitative considerations, posttranslational modifications, including glycosylation, may be crucial in stimulating appropriate antigenic responses in vaccinated animals. In this regard yeast vectors can be useful since both glycosylation and secretion of foreign proteins are possible (Innis et al., *Science* 228:21 26 (1985)). A commercially available system (Immunex Corp., Seattle, Wash.) which is advantageous from both qualitative and quantitative standpoints has recently been described (Hopp et al., *Biotechnology* 6:1204 1210 (1988)). This system allows both the detection and simplified purification of fusion proteins from yeast supernatants or *E. coli* extracts.

Protozoan expression systems. *Tetrahymena* is a ciliated protozoan which is taxonomically related to *I. multifiliis*. *T. thermophila* recognizes UAA and UAG codons as glutamine codons as does *I. multifiliis*. In addition, posttranslational modifications, particularly glycosylation, are expected to occur more normally in organisms related to *Ichthyophthirius* (for example, *Tetrahymena*) than in procaryotes such as *E. coli*, or more distantly related eucaryotes. Because such modifications can play a critical role in immune recognition, *Tetrahymena* can have an advantage on this level as well. Vectors for and gene expression in *Tetrahymena thermophila* have been reported. For example, *T. thermophila* has been successfully transformed using self-replicating palindromic ribosomal DNA (rDNA) purified from macronuclei (Brunk et al., *Exp. Cell Res.* 162:390–400 (1986), Lovlie et al., *Proc. Natl. Acad. Sci. USA* 85:5156 5160 (1988); Tondravi et al., *Proc. Natl. Acad. Sci. USA* 83:4369 4373 (1986)). A selectable paromomycin resistance marker has been isolated and characterized; the resistant phenotype is due to a point mutation in the 17S rRNA gene. Resistance to hydromycin is conferred by this mutation as well (Spangler et al., *J. Biol. Chem.* 260:6334 6340, (1985)). Subsequently shuttle vectors capable of autonomously replicating as plasmids in *Tetrahymena* as well as in *E. coli* have been developed (Yu et al., *Proc. Natl. Acad. Sci USA* 86:8487 8491 (1989)); Yu et al., *Proc. Natl. Acad. Sci. USA* 85:5151 5155, (1988)). Such plasmids have been stably maintained at high copy number for more than 65 generations, and there has been at least one homologous gene expressed from a *Tetrahymena* shuttle vector.

Successful expression of an Ich gene in *T. thermophila* allows the production of relatively large amounts of antigen in a purified form, at relatively low cost. In addition to its use in the production of purified antigens, transformed *T. thermophila* can also be used as a live vector in the animal host, as described above. This second approach provides the most efficient means of exposing fish to *I. multifiliis* surface antigens (short of infecting them with the live parasite itself). Up to 500,000 *T. thermophila* cells can be injected into the peritoneal cavity of 15 g channel catfish, where they survive for several days without causing adverse effects.

EXAMPLES

The present invention is illustrated by the following examples. It is to be understood that the particular examples, materials, amounts, and procedures are to be interpreted broadly in accordance with the scope and spirit of the invention as set forth herein.

Example 1

Isolation and Characterization of the *I. multifiliis* (G1 Isolate) Gene Encoding the 48 kD I-antigen Parasite culture. *Ichthyophthirius multifiliis* (isolate G1) was maintained on juvenile channel catfish (*Ictalurus punctatus*) as previously described (H. Dickerson et al., *J. Euk. Microbiol.*, 40:816–820(1993)). Briefly, the infection is passsaged on fingerling channel catfish by incubation of one infected fish with five uninfected fish in a 10 gallon aquarium. Fish were gently rubbed and host-associated trophonts that were released from the skin were allowed to adhere to the sides of collecting dishes. Cells were then washed once in carbon-filtered tap water and permitted to divide to form infective theronts (18–24 hours at 23° C.). After filtration through 0.0015 inch wire mesh (Fisher Scientific, Pittsburgh, Pa.) cells were used for DNA isolation.

Genomic DNA isolation. Total DNA was obtained using a modification of procedures described by Kavenoff et al. (*Chromosoma,* 41:1–27 (1973)). Theronts were harvested by centrifugation at 1,000×g for 2 minutes and the resulting cell pellet lysed in 2 volumes HET buffer (0.5 M EDTA, 0.01 M Tris-HCl, pH 9.5) containing 1% SDS at 65° C. After 30 minutes, samples were cooled to 50° C. and additional HET containing pronase (2 mg/ml) was added to bring the final volume to 4 times that of the original cell pellet. Lysates were incubated 4–6 hours, diluted with 0.5 vol 0.1×SSC (0.1×SSC: 15 mM NaCl/1.5 mM sodium citrate, pH 7.0) and then extracted with an equal volume of phenol:chloroform: isoamyl alcohol (25:24:1). After separation from the aqueous layer, the organic phase was back-extracted with 0.5 volume of 10 mM Tris-HCl, 1 mM EDTA, pH 8.0 (TE) and the aqueous layers combined. Samples were re-extracted with phenol:chloroform:isoamyl alcohol (25:24:1) and chloroform:isoamyl alcohol (24:1), and nucleic acids were precipitated by addition of 2 volumes ethanol. The precipitate was collected by centrifugation at 10,000×g for 15 minutes (4° C.), washed in cold 70% ethanol and air dried. The pellet was dissolved in 2×SSC containing 1 mM EDTA, and contaminating RNA was removed by digestion with 100 μg/ml RNase A (Promega) at 37° C. for 1 hour. DNA was precipitated by addition of 2 volumes ethanol and collected by centrifugation as above. The pellet was washed for several hours in cold 70% ethanol and the DNA dissolved in TE to a final concentration of 50–250 μg/ml.

Genomic library construction. Total DNA (20 μg) was digested overnight at 37° C. with the restriction endonuclease Swa I (4.2 units enzyme/μg DNA) (Boehringer-Mannheim Biochemicals, Indianapolis, Ind.). This enzyme has an 8 base pair recognition sequence containing all As and Ts. Because the non-coding regions of ciliate DNA are extremely A-T rich, Swa I cuts preferentially and relatively often in intergenic regions yielding roughly gene-sized pieces of DNA. After phenol extraction, restriction fragments were ethanol precipitated and dissolved in TE (10 mM Tris/1 mM EDTA pH 8.0. Potential staggered ends were repaired by incubation with T4 DNA polymerase (0.2 unit/μl for 30 minutes at 37° C.) (Promega, Madison, Wis.), and small fragments (<271 base pairs (bp)) removed by chromatography on Sephacryl 400 (Amersham Pharmacia Biochemical, Piscataway N.J.). Genomic DNA (average size ~1.5–3 kb) was combined with a 20-fold molar excess of $10_{mer}$ EcoR I adaptors (e.g., Cat. No. C-1291, Promega) and the mixture incubated for 18 hours at 15° C. in the presence of T4 DNA ligase (0.25 unit/μl) (Promega). T4 polynucleotide kinase (to 0.25 unit/μl; Promega) and ATP (to 10 nM) were added and the reactions incubated an additional 30 minutes at 37° C. to phosphorylate adaptor ends. Fragments were phenol extracted and ethanol precipitated as above, and again fractionated on Sephacryl 400 to remove excess adaptors. Resulting DNA was then ligated with λZAP II arms (Stratagene, La Jolla, Calif.) which had been EcoR I digested and dephosphorylated. Ratios of insert to vector DNA were varied according to the recommendations of the manufacturer. Individual ligation reactions were packaged using Gigapack II packaging extracts (Stratagene) and libraries titered on *E. coli* XL1-Blue MRF' in the presence of X-gal and IPTG. A library containing $4 \times 10^5$ phage plaques (>90% white) was amplified and used for gene isolation.

Library Screening. The amplified library was plated at $5 \times 10^4$ plaques/150 mm plate and the resulting phage particles lifted onto nylon filters (Micron Separations Inc., Westborough, Mass.) as described by Sambrook et al., (1989). A total of 8 filters were hybridized under conditions of high stringency (5×SSC at 68 C overnight in 2% blocking reagent (Boehringer Mannheim Biochemicals, Indianapolis, Ind.), followed by two 5 minute washes in 2×SSC, 0.1% SDS, followed by two 15 minute washes in 0.5×SSC, 0.1% SDS at 68 C) with a 1.2 kb cDNA probe against the 48 kD i-antigen (Clark et al. *Proc. Nat. Acad. Sci. USA*, 89:6363–6367 (1992)) labeled with digoxigenin (Genius System; Boehringer-Mannheim Biochemicals). This probe was previously shown to encode most of the 48 kD i-antigen of parasite isolate G1. Filters were reacted with an alkaline phosphatase-tagged anti-digoxigenin antibody (Boehringer-Mannheim Biochemicals) and developed with CSPD chemiluminescent substrate (Tropix). Twelve positive clones were isolated and subjected to two rounds of plaque purification, wherein a positive clone is selected, diluted, replated and rescreened. Inserts were then subcloned into pBluescript SK(–) by in vivo excision in the presence R408 helper phage (Stratagene). Plasmid DNA was purified from bacterial cultures by alkaline lysis and anion-exchange chromatography using modified silicagel resins (Qiagen, Valencia, Calif.). Cloned inserts were mapped by digestion with appropriate restriction enzymes using techniques known to one of skill in the art (see, for instance, Sambrook et al., (1989). All positive recombinants contained a 3.3 kb Swa I fragment. A restriction map of the cloned insert from one recombinant (GL3–8) is shown in FIG. 6. Both strands of the region extending from the left end through the distal EcoR I site of the insert were subjected to nucleotide sequencing. DNA sequencing was performed with a Perkin Elmer/Applied Biosystems Division 377 automated DNA sequencer using dye terminator chemistry and AmpliTaq-FS DNA polymerase (Perkin Elmer, Norwalk, Conn.). Sequence analysis showed that the insert encoded the entire 48 kD i-antigen.

Transcript Mapping. The 5' end of i-antigen transcripts were mapped by primer-extension analysis. Briefly, 10 pM of antisense primer H4 (AGCAGCACCTACATCAGT-CAATCC, SEQ ID NO:21) complimentary to a sequence near the putative ATG start codon of the 48 kD i-antigen gene (nucleotides +94–117), was end-labeled with $\gamma^{32}p$ (Amersham, Arlington Heights, Ill.) in the presence of T4 polynucleotide kinase (10 units; Promega) (Sambrook et al., (1989)) The labeled primer (2 pM) was hybridized with 10 µg total RNA from *I. multifiliis* theronts (G1 isolate) and extended at 42° for 1.5 hours in the presence of AMV reverse transcriptase (26 Units; Boehringer-Mannheim). Mussel glycogen was added as a carrier (200 µg/ml; Boehringer-Mannheim) and the extension product was precipitated by addition of 0.5 volume 7.5 M ammonium acetate and 2.5 volumes ethanol. Following centrifugation (14,000×g for 10 minutes), the pellet was air dried and dissolved in $H_2O$. The size of primer extension products was determined relative to a $^{32}P$-labeled sequencing ladder run on parallel lanes of a 6% polyacrylamide/urea sequencing gel. The ladder was prepared in a dideoxy sequencing reaction (Sequenase kit; United Sates Biochemicals) using single-stranded M13 mp18 DNA as a template, and M13 universal primer GTAAAACGACGGCCAGT (SEQ ID NO:22) labeled with $^{32}P$. After electrophoresis, gels were fixed, dried and autoradiographed for visualization of labeled DNA fragments (Sambrook et al., (1989).

The 3' ends of i-antigen transcripts were mapped using the RACE (rapid amplification of cDNA ends) protocol (M. Frohman "RACE: Rapid Amplification of cDNA ends," In: *PCR Protocols: A Guide to Methods and Applications*, Innis, M. A., et al., (eds.) Academic Press, San Diego, pp. 28–38 (1990)). Total RNA was prepared from *I. multifiliis* (G1) theronts by lysis in guanidine thiocyanate, and poly(A)$^+$ mRNA was purified by two rounds of chromatography on oligo(dT)-cellulose (Clark et al. *Proc. Nat. Acad. Sci. USA*, 89:6363–6367 (1992)). First-strand cDNA was then prepared from 1 µg poly(A)$^+$ RNA, using 25 pmol of primer EPBdT$_{18}$ (GCGAATTCTGCAGGATCCAAACT$_{18}$, SEQ ID NO:23); kindly provided by Dr. Royal McGraw, University of Georgia), and AMV reverse transcriptase (0.25 unit/µl; Boehringer-Mannheim) (Sambrook et al., (1989). Following incubation at 42° C. for 2 hours, a fraction of the first-strand product was used as template in a second-round PCR reaction containing either of two forward primers, namely, ICH5 (GTGTCGACAGCAGGTACTGATACATG, SEQ ID NO:24) or H5 (CGAAAACAGTGGTGGTAGTACCTT, SEQ ID NO:25) in combination with the reverse primer, EPB (GCGAATTCTGCAGGATCCAAAC, SEQ ID NO:26). The ICH5 primer corresponded to a region of the gene that lay proximal to the breakpoint between the gene and 1.2 kb cDNA sequence, while H5 corresponded to a region of the 1.2 kb cDNA that lay distal to that site. PCR was carried out under standard conditions using 20 pmol primer/100 µl reaction and 5 U Taq DNA polymerase (Promega) (1 minute at 94° C., 1 minute at 52° C., 1 minute at 72° C.; 30 cycles). The ICH5/EPB product was electrophoresed on a 1.4% agarose gel and ran as a broad band of ~295–375 bp. DNA was eluted from the gel, digested with Sal I and EcoR I, and then directionally cloned into pBluescript SK(–) for subsequent sequence analysis.

cDNA Clones. A λZAP II cDNA library prepared from *I. multifiliis* trophont RNA was screened with a $^{32}P$-labeled 24$_{mer}$ oligonucleotide (5'-AGCAGCACCA ACATCAGTCA AACC, SEQ ID NO:27) encoding eight amino acids near the N-terminus of the 48 kD i-antigen, as previously described (Clark et al. *Proc. Nat. Acad. Sci. USA*, 89:6363–6367 (1992)). In addition to a clone that provided the 1.2 kb i-antigen cDNA (designated 2-3), the library screen yielded several additional positive recombinants. Two such clones (designated 1-1 and 1-3) were chosen for sequence analysis. cDNA inserts were subcloned into pBluescript SK(–), and plasmid DNA sequenced on the positive strand using the ICH5 primer.

Southern blotting analysis. 5' and 3'-specific probes were generated using the polymerase chain reaction. The 5'-specific probe was a 475 bp fragment spanning nucleotides +188–662 of the gene and was amplified using the 1.2 kb cDNA as a template in conjunction with the forward and reverse primers, ATGGTAATTAACCTTTCGCAG-CAAATAA (SEQ ID NO:28) and GGTCTGCATTTAACA-CATAA (SEQ ID NO:29), respectively. The 3'-specific probe was a 495 bp fragment amplified from genomic DNA using H5 as the forward primer, and the reverse primer AGATACATCAGTATACGAAA (SEQ ID NO:30). The later sequence was derived from the H5/EPB RACE product. Probes were purified by agarose gel electrophoresis, and labeled using random oligonucleotide synthesis (High Prime DNA labelling kit™; Boehringer-Mannheim) in the presence of $\alpha^{32}$P-dCTP (Amersham). Genomic DNA (5 μg) from *I. multifiliis* theronts (G1 isolate) was digested with either EcoR I, Hind III or Swa I, fractionated on a 0.7% agarose gel and transferred to nylon. The filter was then hybridized with probes specific for either the 5' or 3' ends of the 1.2 kb cDNA in separate reactions. The probes were radiolabeled to $10^9$ cpm/μg and used at $10^6$ cpm/mL. Hybridization was carried out under conditions of high stringency (washed overnight in 6×SSC, 10× Denhardt's reagent, 0.1% SDS, 10 μg/mL denatured herring sperm DNA at 65 C; followed by one 15 minute wash at room temperature in 2×SSC, 0.1% SDS, followed by one 15 minute wash at 65 C in 2×SSC, 0.1% SDS, followed by one 15 minute wash at 65 C in 0.5×SSC, 0.1% SDS, followed by one 15 minute wash at 65 C in 0.2×SSC, 0.1% SDS) as previously described (Clark et al. *Proc. Nat. Acad. Sci. USA*, 89:6363–6367 (1992)).

Comparisons between gene and cDNA sequences. Results of nucleotide sequencing reactions were complied and analyzed using DNASIS software (version 2.0; Hitachi Software Engineering, Yokahama, Japan). When the nucleotide sequence of the 1.2 kb cDNA used as a probe in this study was compared with the coding region of the 48 kD i-antigen gene, a number of differences were observed. These included two single-base substitutions (nucleotides +781 and 952), as well as complete divergence in the region distal to nucleotide +1227 (nucleotide 1172 of the cDNA). To determine whether these differences were real, the 1.2 kb i-antigen cDNA was resequenced and found an error at position +781 (position 726 of the cDNA should read A rather than C as originally reported) (GenBank accession no. M92907 updated). The transversion at nucleotide 952, and the divergent sequence at the 3' end of the cDNA were, nevertheless, confirmed.

Figure 7A:
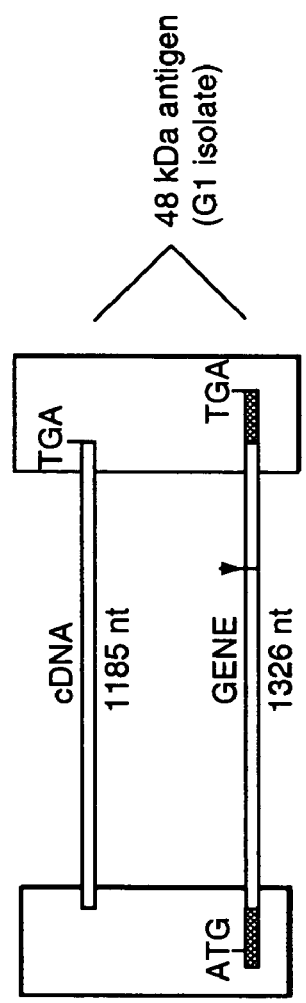
FIG. 7 shows a comparison between the IAG48[G1] gene sequence and 1.2 kb cDNA sequence. Panel (A) is a schematic illustrating the basic differences between the gene and cDNA sequences (boxed); the filled regions of the gene sequence are not present in the 1.2 kb cDNA sequence; ATG, start codon; TGA, stop codon; nt, nucleotides; inverted triangle indicates the site of the observed C/T transversion. Panel (B) diagrams equivalent regions of the 1.2 kb cDNA (nucleotides 1–1172) and IAG48 [G1] gene (nucleotides 56–1227); the C/T transversion is indicated at nucleotide 897 (cDNA) and 952 (genomic DNA). Panel (C) shows the nucleotide sequences specified by the 3' ends of the 1.2 kb cDNA (SEQ ID NO:64), the IAG48 [G1] gene (SEQ ID NO:66), the ICH5/EPB 3' RACE product (SEQ ID NO:67), and two additional cDNAs designated 1-3 (SEQ ID NO: 68) and 1-1 (SEQ ID NO:69); also shown are the corresponding deduced amino acid sequences of the 1.2 kb cDNA (SEQ ID NO:63) and the IAG48 [G1] gene (SEQ ID NO:65); a point mutation in the RACE product is boxed and is most likely attributable to the use of a low fidelity thermostable DNA polymerase during synthesis; the bracket covering nucleotides +1409 through +1413 in the IAG48[G1] transcript indicates a putative polyadenylation site.
Figures 7B, 7C:
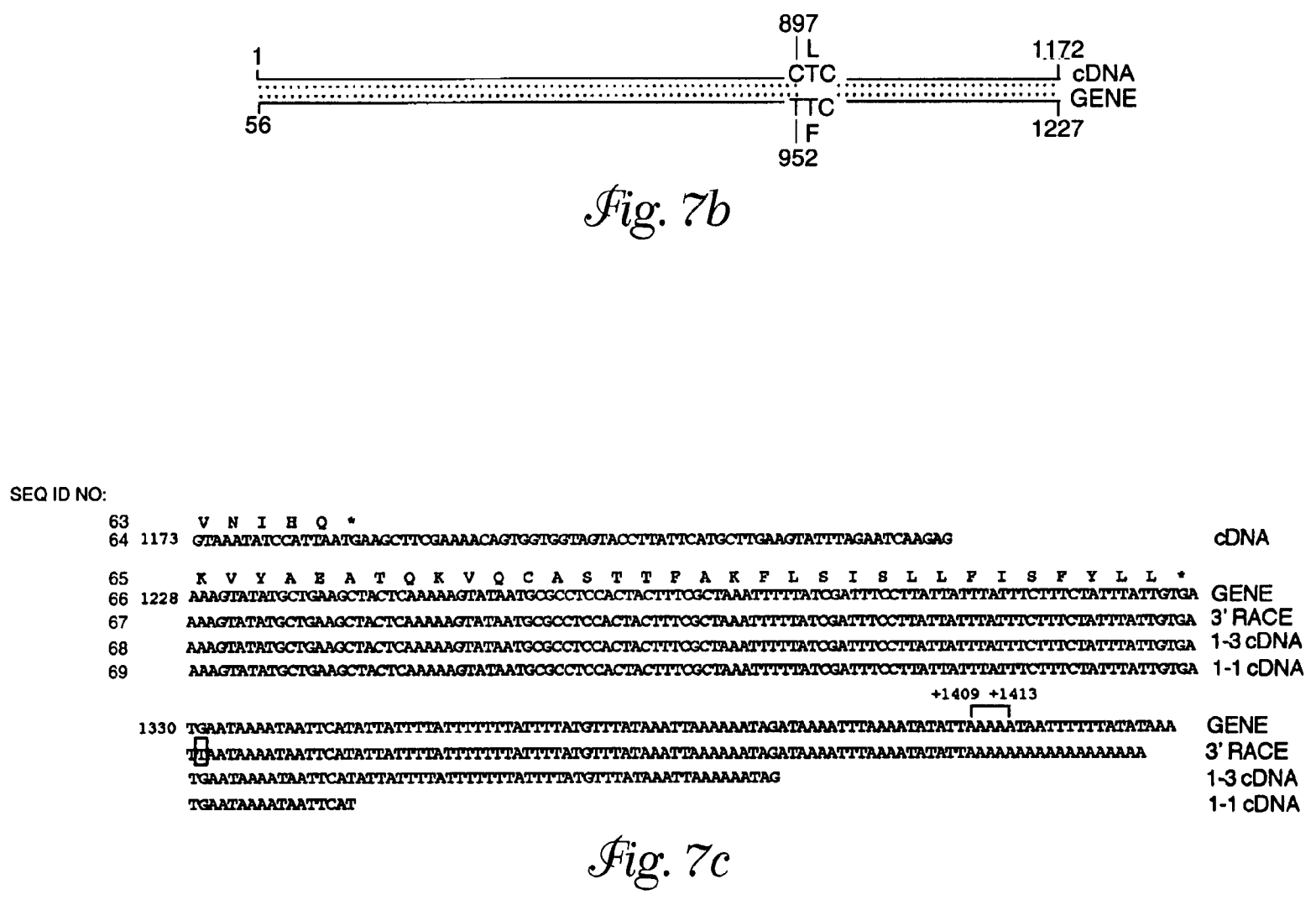

As indicated in FIG. 7, these differences would result in an amino acid substitution at position 318 (phenylalanine for leucine), and an entirely different sequence at the carboxy-terminus of the gene product. Specifically, the cDNA product would lack the C-terminal hydrophobic amino acid residues specified by the gene. Hydrophobic domains at the C-termini of GPI-anchored proteins are necessary for covalent attachment of glycosylphosphatidylinositol moieties (P. Englund, *Annu. Rev. Biochem.*, 62:121–138 (1993)), and the deletion of relevant coding sequences from transgenes that encode such proteins usually results in secretion rather than membrane binding. Furthermore, there are a number of instances in which alternative splicing of endogenous mRNAs gives rise to transcripts that either specify, or fail to encode hydrophobic C-terminal peptides (I. Caras et al., *Nature* 325:545–548 549 (1987); H. Gower et al., *Cell*, 55:955–964(1988)). In the first case, such products are retained at the plasma membrane (as GPI-anchored proteins), while in the second, they are exported from the cell. Both secreted and membrane bound forms of a 48 kDa i-antigen have been described in *I. multifiliis* (C. Xu et al., *J. Euk. Microbiol.*, 42:558–564 (1995)). It should also be noted that the parasite isolate designated G1 contains a second i-antigen gene believed to encode an antigenically related 60 kDa protein (T. Clark et al., *Annu. Rev. Fish Dis.*, 5:113–131 (1995)); this gene is recognized by the 5'-specific probe used in this study and appears as a 5 kb fragment in the Swa I digest as discussed below. The 3'-specific probe fails to recognize this fragment indicating that the 1.2 kb cDNA is not a product of this gene.

Interestingly, when the 3'-end of i-antigen transcripts were mapped by RACE using a sense primer upstream of nucleotide +1227 (primer ICH5), the resulting PCR product had essentially the same sequence as the gene (FIG. 6). Consistent with this observation, two independent i-antigen cDNAs were isolated from the same library used to prepare the 1.2 kb probe and found that these contained the same sequence as the gene at their 3' ends (FIG. 6). By contrast, when a sense primer corresponding to the 1.2 kb cDNA downstream of nucleotide 1172 (primer H5; see herein) was used, the RACE product that was generated was much larger than expected (~600 bp) and had a sequence entirely different from that of the gene. Furthermore, it was not possible to generate PCR products with genomic DNA as a template in standard reactions using sense and antisense primer pairs that flanked nucleotide 1172 of the 1.2 kb cDNA.

Since this suggested that the sequences on either side of nucleotide 1172 were discontinuous within the genome, Southern hybridization analysis was carried out using probes described above corresponding to 5' and 3' regions of the 1.2 cDNA. The restriction fragments recognized by the two probes were different. A 3.3 kb band recognized by the 5'-specific probe in the Swa I digest corresponded to the genomic DNA fragment described herein. A larger (5 kb) band was also observed, which may represent the gene for a related 60 kD i-antigen expressed by the G1 isolate (Clark et al., *Proc. Nat. Acad. Sci. USA*, 89:6363–6367 (1992); T. Clark et al., *Annu. Rev. Fish Dis.*, 5:113–131 (1995)).

Example 2

Identification of the Open Reading Frame and Analysis of the Deduced 48 kD I-antigen Sequence from *I. multifiliis* (G1 Isolate)

Computer-based sequence analysis. Homology searches were performed at the ISREC World Wide Web server (Swiss Institute for Experimental Cancer Research) using the BLAST network service (BLAST, basic local alignment search tool; WU-BLAST server version 2.0a13) and the SwissProt+Trembl+TrUpdates peptide sequence databases. Predictions of potential signal peptides and their cleavage sites were made using the Signalp World Wide Web server (http://www.cbs.dtu.dk/services/SignalP/) version 1.0. Peptide mass was determined using the PEPTIDE MASS tool accessed through the ExPASy molecular biology World Wide Web server of the Swiss Institute of Bioinformatics (http://expasy.hcuge.ch/sprot/peptide-mass.html). Amino acid sequence alignment was carried out using the CLUSTALW (1.74) multiple sequence alignment program accessed through the ExPASy web server.

Identification of the open reading frame. The cDNA used to screen the genomic library in Example 1 begins with a 5'-terminal G that lies several nucleotides upstream of a valine codon (GTT) marking the N-terminus of the mature 48 kD i-antigen (Clark et al., *Proc. Nat. Acad. Sci. USA*, 89:6363–6367 (1992)). This G residue corresponds to nucleotide +56 of the genomic DNA sequence shown in FIG. 1. Translating downstream from this nucleotide (and in-frame with the original cDNA), the gene was found to contain a single, uninterrupted reading frame extending through nucleotide +1326, followed by two adjacent TGA stop codons. *I. multifiliis*, along with other hymenostomatid ciliates, utilize TGA as the only stop codon; the standard TAA and TAG triplets specify glutamine instead.

Translating in the opposite direction, the region immediately upstream of the 5'-terminus of the cDNA was found to encode a methionine (predicted by the ATG triplet at nucleotides +1–3), followed by a stretch of 19 mostly hydrophobic amino acids. The hydrophobic nature of these amino acids (along with the fact that the i-antigens are membrane polypeptides) would suggest that this region specifies a signal peptide that targets the protein to the plasma membrane. To investigate this further, neural network algorithms trained on signal peptides and their cleavage sites (H. Nielsen et al., *Prot. Engin.*, 101 1–15 (1996)) were used to examine the first 50 amino acids of the deduced protein sequence beginning with the methionine residue cited above. Such algorithms identified the first 20 amino acids as a signal peptide (S mean=0.839), and predicted a cleavage site between the alanine and valine residues (amino acids 20 and 21, respectively) of the deduced amino acid sequence. The N-terminal amino acid of the 48 kD antigen protein corresponds to the valine residue predicted above (Clark et al., *Proc. Nat. Acad. Sci. USA*, 89:6363–6367 (1992)). Taken together, these observations argue strongly that amino acids 1–20 of the deduced protein constitute a signal peptide.

Assignment of the methionine residue (amino acid position 1) as the start site of the 48 kD protein is also supported by the results of primer extension analysis on polyA+RNA from the infective theronts. I-antigen transcripts appear to initiate at two sites located −33 and −34 nucleotides upstream of the A nucleotide of the methionine codon. Because no other ATG triplets are predicted within this region, the methionine residue at position 1 almost certainly represents the translational start site of the protein itself. Based on these considerations, the coding region of the gene extends 1326 nucleotides and specifies a protein precursor of 442 amino acids having a theoretical $MW_r$ (molecular mass) of 45,025 daltons. The gene is designated IAG48[G1]. A total of 23 UAA and UAG triplets (encoding glutamine in *I. multifiliis* but functioning as stop codons in most other eukaryotes and prokaryotes) are present within IAG48[G1].

Curiously, the third position of the codons shared a strong preference for either A or T (84.9%). While the significance of this is not understood, such bias appears to be a common feature of i-antigen genes (D. Martindale, *J. Protozool.*, 36:29–34 (1989); J. Deak et al., *Gene*, 164:163–166 (1995)) and may reflect important constraints on RNA structure. The polyA tract at the 3' end of the RACE product, shown in FIG. 7, most likely represents the site at which polyadenylation of IAG48[G1] mRNA occurs. Based on this (and assuming an average length of 100–200 nt for the polyA tail), the predicted size of RNA transcripts from this gene would be in the range of 1,543–1643 nt.

Amino acid sequence motifs. Analysis of the deduced protein sequence of the gene revealed a minor discrepancy between the predicted mass of the preprocessed protein (45 kDa), and the size of the mature i-antigen based on SDS-PAGE (48 kDa) (T. Clark et al., *Annu. Rev. Fish Dis.*, 5:113–131 (1995)). Potential secondary modifications could appreciably alter the electrophoretic mobility of the processed protein. Furthermore, structural anomalies associated with repetitive sequence motifs could lead to incorrect estimates of size based on SDS-PAGE.

This aside, the most interesting structural features of the deduced protein are hydrophobic regions at the N- and C-terminus, a consensus P-loop domain, and tandemly repetitive cysteine-rich motifs. A stretch of 14 mostly hydrophobic amino acids separated from a short spacer from three small amino acids (-Cys-Ala-Ser-) was predicted at the extreme carboxy-terminus of the protein (FIG. 1). This type of sequence is highly characteristic of an addition site for a glycosylphosphatidylinositol (GPI) anchor (P. Englund, *Annu. Rev. Biochem.*, 62:121–138 (1993)). Other evidence shows that the 48 kD i-antigen is, in fact, GPI-anchored. The hydrophobic region at the amino-terminus of the protein is consistent with i-antigens being membrane associated proteins; presumably, the N-terminus targets the protein to the endoplasmic reticulum. The P-loop domain at position 316–323 [Gly-[$Xaa_4$]-Gly-Lys-Ser] (SEQ ID NO:34) may or may not be significant. While this type of structure is generally associated with proteins that bind ATP or GTP, the presence of such motifs does not insure a role in nucleotide binding (M. Saraste et al., *Trends Biochem. Sci.*, 15:430–434 (1990)). Indeed, proteins with closest similarity to the 48 kDa i-antigen in terms of primary structure (i.e., the Lembadion L-factor, *Tetrahymena* SerH, and *Giardia* VSP surface antigens) all lack a consensus phosphate-binding loop. Instead, these proteins, like the deduced 48 kD i-antigen, have numerous Cys-$Xaa_{2,3}$-Cys (SEQ ID NO:31, 32) motifs embedded within higher order tandemly repeated amino acid sequence domains.

Repetitive sequence domains. Beginning with a cysteine residue at position 23, five homologous segments with an average of 80 amino acids each were identified within the deduced 48 kD i-antigen protein sequence (FIG. 5(*a*)). Adjacent repeats had the greatest degree of homology, with the second and third being ~90% identical. As shown in FIGS. 5(*a*) and (*b*), the repeats are characterized by 6 invariant cysteines that fall into register when the segments are aligned. The predominant spacing between cysteines has the order Cys-$Xaa_{2,3}$-Cys (SEQ ID NO:31, 32). There are 14 such motifs in the 48 kD i-antigen protein sequence, as well as 4 larger elements having the order, Cys-$Xaa_2$-Cys-$Xaa_{20}$-Cys-$Xaa_3$-Cys-$Xaa_{20}$-Cys-$Xaa_2$-Cys (SEQ ID NO:34). The spacing between the last cysteine of each repeat, and the first cysteine of the next repeat is Cys-$Xaa_3$-Cys (SEQ ID NO:32).

Cysteine motifs with the order Cys-$Xaa_{2,3}$-Cys (SEQ ID NO:31, 32) are common to a large and diverse family of proteins that bind zinc and other metal ions (J. Berg et al., *Science*, 271:1081–1085 (1996)). A search of the SWISS-PROT/TrEMBL database showed similarities (smallest sum probability level$\geq$2.8e-06) between the 48 kD i-antigen and several other entries, five of which were protozoan membrane proteins. These included the SerH immobilization antigen of the free-living ciliate *Tetrahymena thermophila* (accession no. Q27197), a putative membrane protein (L-factor) from the predatory ciliate *Lembadion bullinum* (accession no. Q94589), and three variant-specific surface proteins (VSPs) of the mammalian gut parasite, *Giardia lamblia* (accession nos. Q24977; Q24970; P21849). Homologies with two additional entries (an antifreeze protein from Arctic cod [accession no. Q13028], and the product of an unidentified gene from *Caenorhabditis elegans* [accession no. Q17084]) were considered less significant because of unusual bias in the amino acid composition of these proteins. With regard to the protozoan membrane proteins, all contained numerous Cys-$Xaa_{2,3}$-Cys (SEQ ID NO:31, 32) motifs. The product of the *Giardia* vspA6-S1 gene (accession no. Q24970) showed the greatest similarity to the 48 kD i-antigen in terms of the overall spacing of these motifs, with 29 of a possible 30 cysteine residues in the *I. multifiliis* protein overlapping with the identical amino acid in the vspA6-S1 gene product (FIG. 8). This region has eight Cys-$Xaa_{2,3}$-Cys (SEQ ID NO:31, 32) motifs that do not align with similar domains in the *I. multifiliis* polypeptide.

Example 3

Identification of an *I. multifiliis* (G5 Isolate) Gene Encoding a 55 kD I-antigen Construction of G5 cDNA library. A G5 cDNA library was made as follows. First-strand cDNA synthesis was primed with a 20-fold molar excess of oligodT$_{18}$ in a reaction containing 5 µg of polyA$^+$ RNA from *I. multifiliis* theronts (strain G5) and AMV reverse transcriptase as described by Krug et al. (*Meth. Enzymol.* 152:316–325 (1987)). Second-strand synthesis was carried out in the presence of DNA polymerase I and Rnase H, followed by hairpin loop cleavage with mung bean nuclease as described by Gubler (*Meth. Enzymol.*152:330–335 (1987)). The second-strand product was size-fractionated and adaptors were added as in construction of the G1 genomic DNA library (Example 1). After removal of excess adaptors, material >500 bp was cloned into the lambda phage vector λZAPII™ as for G1 genomic DNA.

Screening of the G5 cDNA library. The G5 cDNA library was first screened under conditions of reduced stringency with a digoxigenin-labelled probe corresponding to the coding region of the 48 kD i-antigen gene of parasite isolate G1. No positive clones were identified. Previous attempts to screen a custom-made genomic DNA library from another parasite isolate (G1.1) with the same probe had also resulted on no positive clones.

Figure 9:
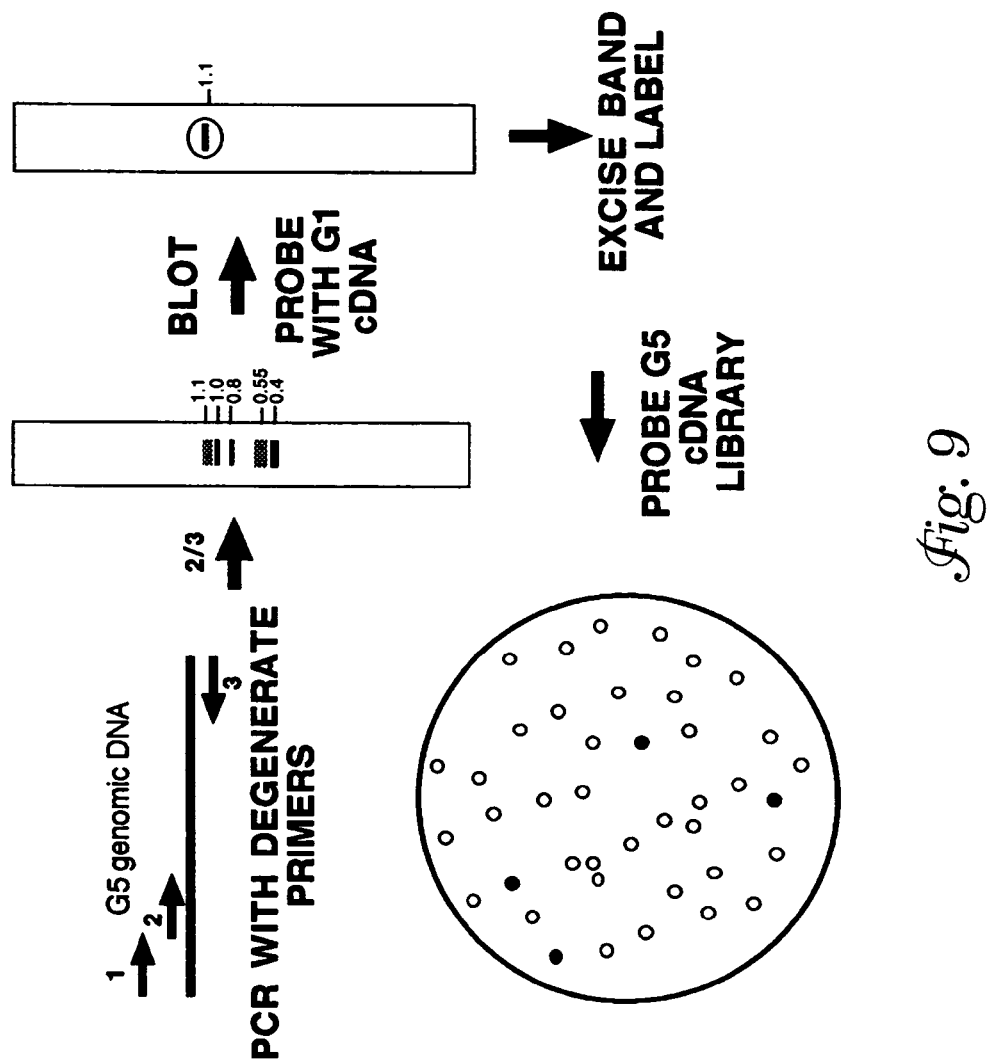
FIG. 9 is a schematic illustrating the method used to isolate the 1 kb cDNA encoding a portion of the G5 55 kD i-antigen sequence.

Degenerate PCR primers were then produced against the 5' and 3' ends of the 48 kD i-antigen gene. These primers, designated #35 and #37, corresponded to the 5' and 3' regions of the coding sequence of IAG48[G1], and the primer sequences were as follows: #35: ATGAAATA(C/T)AA(C/T)ATTTTATTAATT (SEQ ID NO:35), which is a 4-fold degenerate sense primer corresponding to all or part of the amino acid sequence MKYNILLT (SEQ ID NO:36) at the N-terminus of the IAG48[G1]gene product; and #37: AAATAATAA(G/A)GAAAT(A/C)GATAAAAA (SEQ ID NO:37), which is a 4-fold degenerate antisense primer corresponding to all or part of the amino acid sequence FLSISLLF (SEQ ID NO:38) at the C-terminus of the IAG48[G1]gene product. PCR conditions were 30 cycles of 94° C. for 1 minute, 52° C. for 1 minute, 72° C., for 1 minute. A single band corresponding to an amplified i-antigen coding region (55 kD) was expected. However, this reaction yielded several bands on agarose gels visible by ethidium staining, none of which had the expected size of a product from a gene encoding a 55 kD protein (FIG. 9).

To determine which band, if any, corresponded to an amplified i-antigen coding region, the amplification products were Southern blotted and probed under conditions of reduced stringency with a radiolabelled cDNA probe corresponding to the 48 kD i-antigen of isolate, i.e., radiolabelled IAG48[G1]. Hybridization conditions were 6×SSC (Denhardt's, SDS, herring sperm DNA) at 55° C. overnight. Blots were washed in 2×SSC at RT (2×15 minutes), followed by 2×SSC at 55° C. (2×15 minutes). The IAG48[G1] probe revealed a band of about 1.1 kb on the blot.

The amplification products were again resolved by agarose gel electrophoresis, the region of the gel corresponding to DNA fragments of approximately 1.1 kb was excised, and the fragment was labeled with $^{32}$P-dCTP. The radiolabelled fragment was used to probe the G5 cDNA library under high stringency conditions as for the G1 genomic DNA library (Example 1). A single positive clone containing a 1 kb cDNA insert was identified. On sequencing, this cDNA predicted a protein with all the hallmarks of an i-antigen, viz. tandemly repetitive amino acid sequence domains (approximately 80 amino acids each) containing 6 periodic cysteine residues (C-X$_{2,3}$-C motifs), in addition to a stretch of hydrophobic amino acids at the C-terminus virtually identical to those predicted by the gene for the 48 kD antigen. The 1 kb cDNA was nevertheless truncated and lacked the region coding for the N-terminal part of the protein.

RACE (Rapid Amplification of cDNA Ends) was carried out in an attempt to determine the missing 5' sequence. An antisense primer designated G5-11 (TGCTCGAGAATCT-GTTGCTCCACCTG, SEQ ID NO:39) was used for first-strand cDNA synthesis, then a polyG tail was added and the resulting cDNA was amplified with the forward and reverse primers Q$_o$ (CCAGTGAGCAGAGTGACGAGGACTC-GAGCTCAAGCCCCCCCCCCCC CCCCCC, SEQ ID NO:40) and, G5-11 (TGCTCGAGAATCTGTTGCTCCAC-CTG, (SEQ ID NO:39) respectively (PCR conditions: 1 cycle of 94° C. for 3 minutes, 30° C. for 2 minutes, 72° C. for 40 minutes, then 30 cycles of 94° C. for 45 seconds, 53° C. for 45 seconds, 72° C. for 90 seconds (e.g., Frohman, *Meth. Enzymol.* 218:340–356 (1993)). This was followed by a second round of (nested) PCR using the forward and reverse primers Q$_1$ (GAGGACTCGAGCTCAAGC, SEQ ID NO:41) and G5-12 (AACTCGAGTACCAG-CAGGGCATTTAAC, SEQ ID NO:42), respectively (PCR conditions: 30 cycles of 94° C. for 45 seconds, 53° C. for 45 seconds, 72° C. for 2 minutes). This produced a RACE product that approached the extreme 5' end of the coding region of the G5 gene (IAG55(G5)), but still failed to reach it; no ATG start codon was observed.

Figure 10:
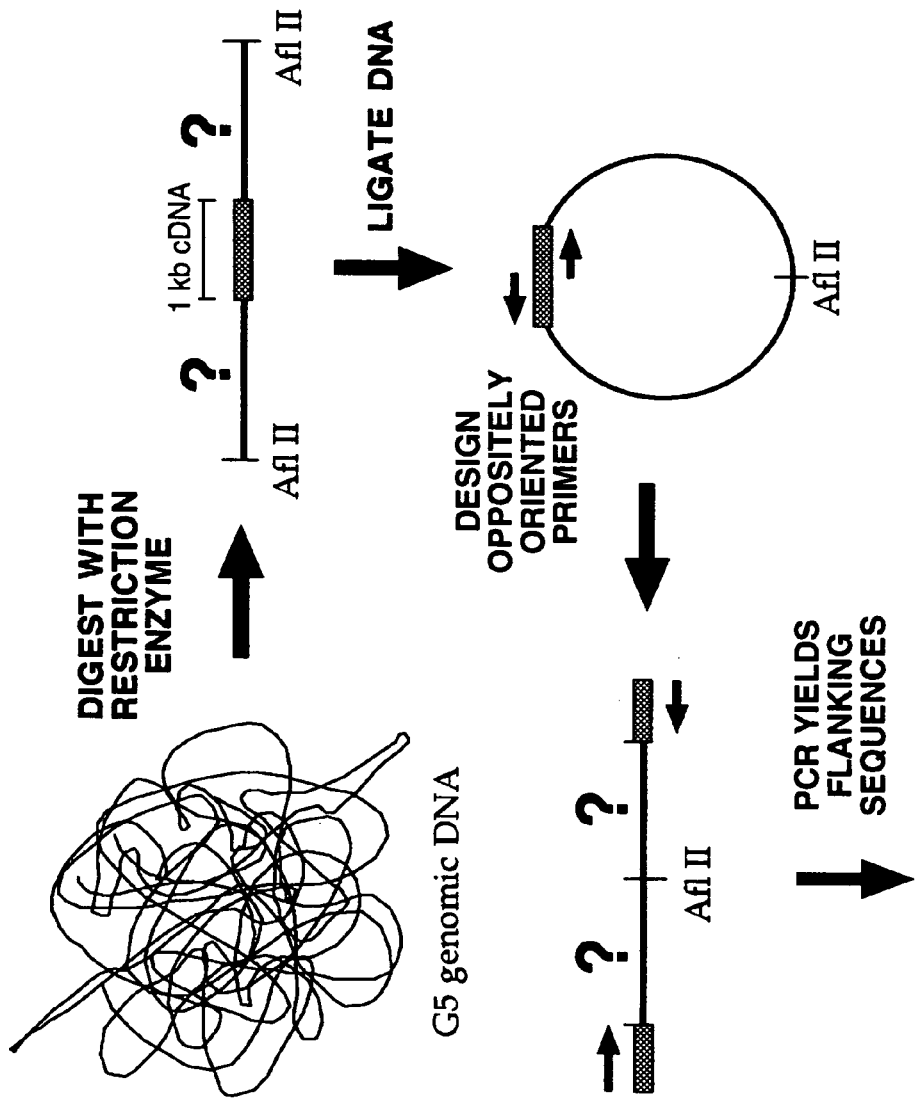
FIG. 10 is a schematic illustrating a method utilizing inverse PCR that was used to obtain the nucleotide sequences flanking the 1 kb cDNA sequence in the gene encoding the G5 55 kD i-antigen.

We then resorted to a procedure referred to as inverse PCR (see FIG. 10). Based on the known sequence of the 1 kb cDNA (the shaded bar in FIG. 10), two oppositely oriented primers, G5-11 (SEQ ID NO:39) and G5-4 (CA-CACCTTGTCCGGCAATTAAAC, SEQ ID NO:43) were designed and used to amplify the regions flanking the 5'- and 3'-ends of the 1 kb cDNA. Genomic DNA (1 µg) from the G5 parasite isolate was incubated with a variety of different restriction enzymes (including Afl II and Swa I) in separate 20 µl reactions for 6 hours. DNA fragments were brought to a volume of 200 µl in 1×DNA ligation buffer (Gibco-BRL Life Technologies, Gaithersburg, Md.), then chloroform extracted and allowed to self-anneal at 22° C. for 12 hours in the presence of T4 DNA ligase (40 U) (Gibco-BRL). DNA was ethanol precipitated and amplified using the forward and reverse primer pair G5-11 and G5-4 under the following conditions: 10 cycles of 94° C. for 10 seconds, 60° C. for 30 seconds, 68° C. for 4 minutes, followed by 20 cycles of 94° C. for 10 seconds, 60° C. for 30 seconds, 68° C. for 4 minutes (+20 seconds for each cycle). DNA fragments of about 1.6 and about 1.9 kb were produced in the samples generated by the restriction enzymes Afl II and Swa I, respectively. The amplified products were cloned into the pCR-Script™ plasmid vector (Stratagene) and sequenced. Both clones contained the 5' end of the coding sequence of the 55 kDa i-antigen gene, along with additional sequences flanking the 5' and 3' ends of the coding regions.

New forward and reverse primers were constructed based upon nucleotide sequences of the 5' and 3' regions flanking the 55 kD coding region, and these primers were used to amplify the entire coding region of the gene using G5 genomic DNA as a template. A comparison between the deduced amino acid sequence encoded by the 48 kD i-antigen gene and the deduced amino acid sequence encoded by the 55 kD i-antigen gene, and of the coding regions of the two genes, is shown in FIG. 3.

Example 4

Figure 11:
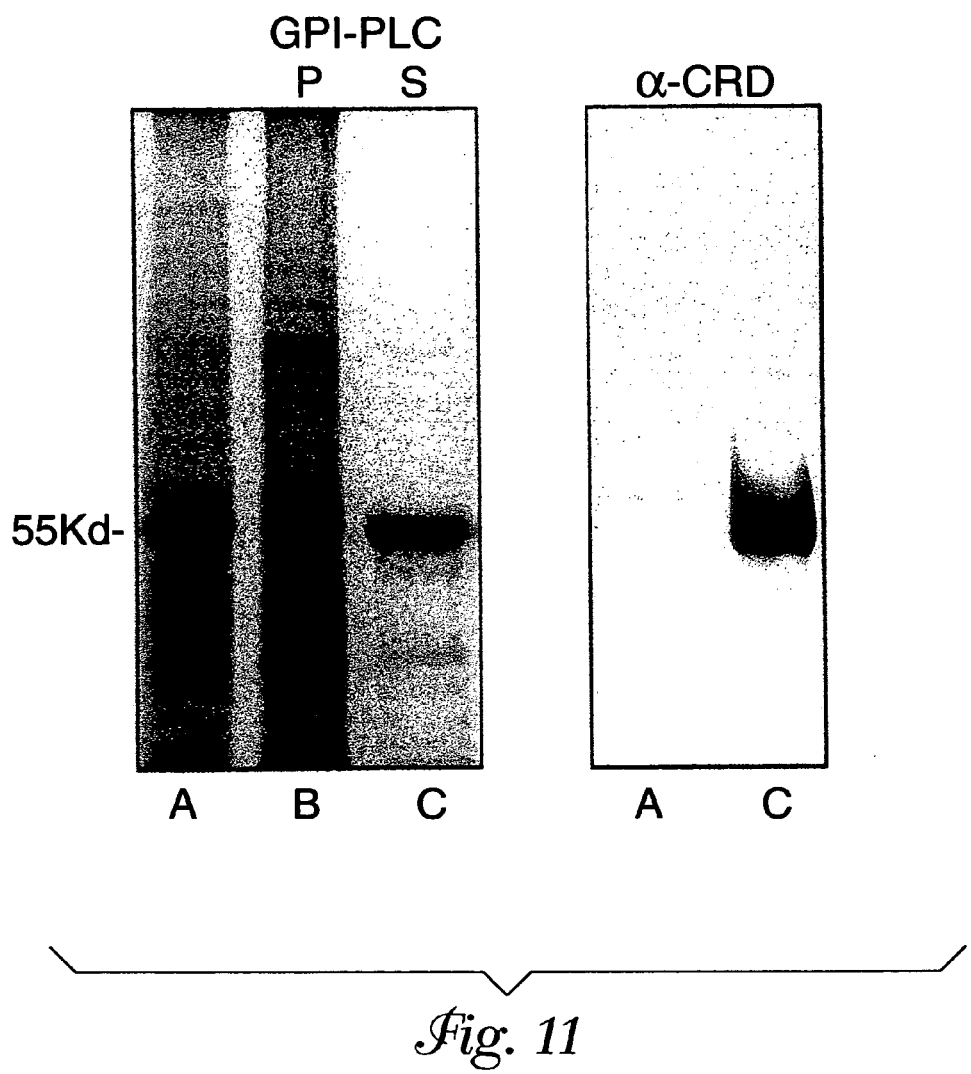
FIG. 11 shows an SDS-PAGE gel and a Western blot of solubilized and GPI-phospholipase C treated membrane proteins from *I. multifiliis* (strain G5).

Glycolipid Anchoring of *I. multifiliis* (G5 Isolate) 55 kD I-antigen Protein Membrane proteins from *I. multifiliis* (strain G5) were extracted with the non-ionic detergent Triton X-114. Following Triton extraction, detergent micelles (containing amphipathic proteins) were treated with a recombinant GPI-phospholipase C (GPI-PLC) from African trypanosomes which cleaves the lipid anchor from GPI-linked membrane proteins. FIG. 11, left panel, shows a Coomassie blue stained gel of theront membrane proteins fractionated by SDS-PAGE. Lane (A) contains total detergent soluble membrane proteins. The prominent band at 55 kD represents the i-antigens of the G5 strain. Lane (B) shows the detergent soluble membrane protein fraction after cleavage with GPI-PLC. Lane (C) contains proteins liberated into the aqueous phase afer enzyme treatment. Note the transfer of the 55 kD band from the detergent to the aqueous phase. FIG. 11, right panel, shows a Western Blot of fractions (A) and (C) reacted with an antibody conjugate that recognizes a cross-reacting determinant on the cleaved portion of the GPI-anchor that becomes exposed following enzyme treatment. Positive staining of a 55 kD band in lane (C) (but not A) argues strongly for GPI-linkage of *Ichthyophthirius* i-antigens with the plasma membrane.

Example 5

Recombinant Production of a 55 kD I-antigen Protein in *E. coli*

Synthesis of a synthetic gene. A synthetic G5 i-antigen gene sequence (SEQ ID NO:102, FIG. 2(*b*)) was constructed using a method known as DNA shuffling essentially as described by Stemmer, et al. (*Gene* 164:49–53 (1995)). Eighteen overlapping primers (primers 3201–3218, FIG. 12) spanning the entire length of the G5 i-antigen coding sequence were combined in a single tube at a final concentration of 5 µM and allowed to assemble in a cycling reaction carried out 30 times at 94° C. for 15 seconds, 52° C. for 30 seconds and 70° C. for 30 seconds (plus 10 additional seconds in each cycle). Following the assembly reaction, 2.5 µl of the product was amplified with the original flanking primers (3201 and 3218) to produce a full-length synthetic gene. The resulting product was cloned and sequenced. Mutations arising from error-prone synthesis PCR were corrected by site-directed mutagenesis (Transformer Site-Directed Mutagenesis kit, Clontech Laboratories, Inc., Palo Alto, Calif.).

Synthesis of modified versions of the synthetic gene. Based on its deduced sequence, the 55 kD protein contains hydrophobic sequences at its N- and C-terminus that are presumed to target the protein to the plasma membrane (the N-terminal sequence acting as a signal peptide for ER localization, and the C-terminal sequence acting as a GPI-anchor cleavage and addition site). To determine whether different gene products might be processed differentially by the immune system following their expression in fish, we made two modified versions of the gene, one lacking the GPI-anchor addition sequence and the other lacking the N-terminal signal peptide. Specifically, we wanted to determine whether the product of the C-terminal deletion might give rise to a stronger humoral immune response since it was expected be secreted from cells rather than be bound to the plasma membrane through a glycolipid anchor. Therefore, having made the synthetic gene for the 55 kD protein, we used PCR to construct the modified versions of the full-length gene. The first lacked the coding region for the signal peptide at the N-terminus (residues 1–20), and the second lacked the hydrophobic stretch at the extreme C-terminus of the protein (amino acids 453–468).

Figures 13, 13A, 13B:
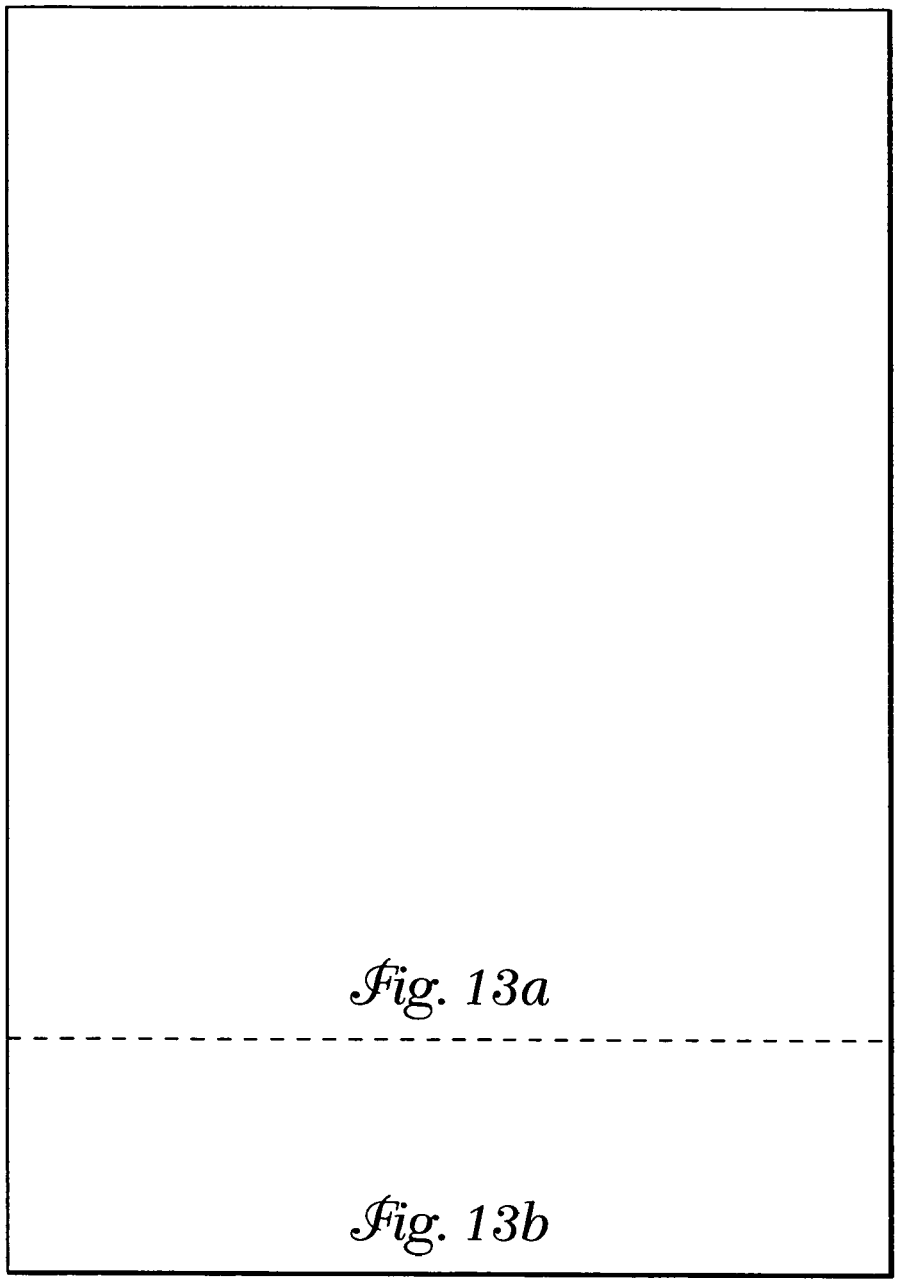
FIG. 13 shows the nucleotide sequence encoding the synthetic G5 proline mutant i-antigen protein (L6P) (SEQ ID NO:53); the arrow indicates the mutation position.
Figure 15:
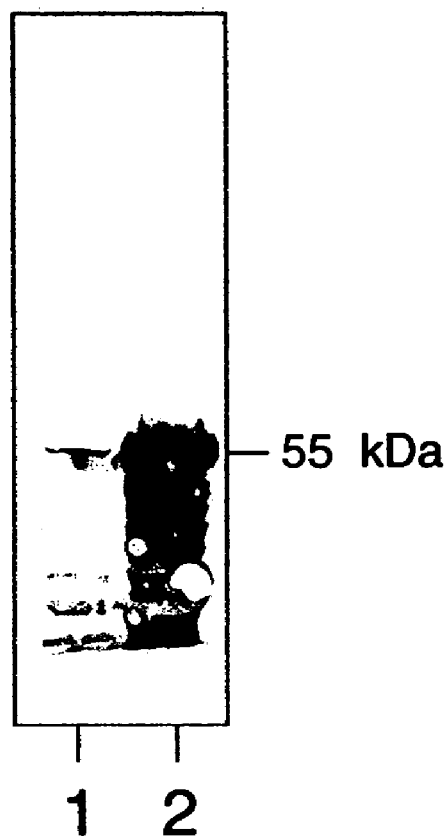
FIG. 15 is a Western blot showing expression of a recombinant synthetic 55 kD i-antigen protein in *E. coli*.

I-antigen protein production in *E. coli*. A recombinant version of the 55 kD *I. multifiliis* i-antigen protein of parasite isolate G5 (SEQ ID NO:7) was produced in *E. coli* strain XL-1 Blue using the plasmid expression vector pProEX™-1 (Gibco-BRL LifeSciences) into which a version (SEQ ID NO:53) of the synthetic gene (SEQ ID NO:5) had been inserted. This version (SEQ ID NO:53) was identical to SEQ ID NO:5 except that it contained a point mutation at nucleotide position 17 in the coding sequence (FIG. 13), resulting in the substitution of a proline for a leucine at amino acid position 6 in the i-antigen protein sequence (L6P) (SEQ ID NO:54) (FIG. 14). Logarithmic cultures were incubated in IPTG to induce expression of the 55 kD antigen fused to a 6×-histidine tag and rTEV protease cleavage signal. FIG. 15 shows a Western blot of a 10% SDS-polyacrylamide gel on which equivalent amounts of bacterial protein from cells taken before (1) and above (2) induction with IPTG were run. The blot was reacted with monospecific rabbit antibodies against the 55 kD i-antigen of the G5 strain followed by goat anti-rabbit IgG couples to alkaline phosphatase. Color substrates were NBT an BCIP. Note the strong band at about 55 kD in the induced sample.

The modified versions of the synthetic gene that lacked membrane targeting sequences at their 5'- or 3'-ends were cloned into several procaryotic expression vectors containing IPTG-inducible promoters (pProEX-1 (Gibco), pET22b (+) (Novagen), pQE-16 (Qiagen) and pGEX-4P-I (Pharmacia)). Recombinant proteins of the expected size that reacted strongly on Western blots with monospecific polyclonal antibodies against the 55 kDa antigen were produced in all bacterial transformants following the addition of IPTG.

Example 6

Figure 16:
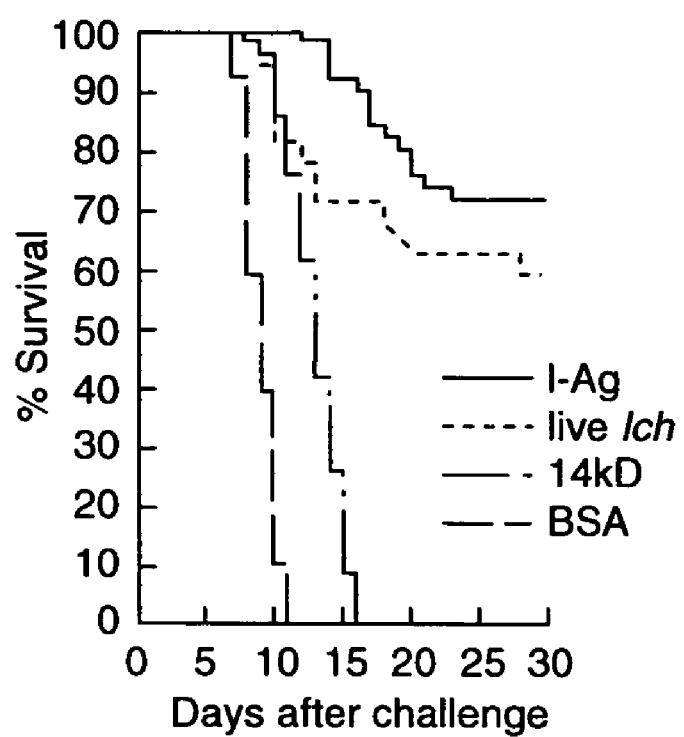
FIG. 16 sh for use in ciliate expression systems, can be determined using the modified genetic code for ciliates, as described herein.

Immune Response of Catfish to Vaccination with *I. multifiliis* (G5 Isolate) 55 kD I-antigen Protein It is known that naive fish are completely protected against infection by *I. multifiliis* following passive transfer of immobilizing murine monoclonal antibodies (mAbs). To test whether *I. multifiliis* i-antigens themselves can elicit protective immunity, vaccination trials were carried out with channel catfish (*Ictalurus punctatus*) immunized with 55 kD i-antigen purified by mAb affinity chromatography from *I. multifiliis* serotype D. Fifty channel catfish (each weighing 10–15 g) were immunized by two intraperitoneal (i.p.) injections (two weeks apart) consisting of 10 µg of purified 55 kD i-antigen of the *I. multifiliis* G5 isolate (i-Ag) in Freund's complete or incomplete adjuvant. The same number of negative control animals were immunized similarly with either an irrelevant 14 kDa *I. multifiliis* G5 protein (14 kD) or bovine serum albumin (BSA). A fourth group of positive control fish was vaccinated by two i.p. injections of 8000 and 10,000 live G5 parasites (live Ich) without adjuvant (this treatment has previously been shown to elicit protective immunity). All groups were challenged with infective G5 theronts (15,000/fish) 8 weeks after the last injection. Seventy-two percent (72%) of fish immunized with the i-antigen and 59.2% of fish immunized with live parasites survived challenge (FIG. 16). All of the negative control animals died. In addition, there were significant differences (P>0.001, Kruskal-Wallis one way ANOVA) between the median days to death of controls and the fish that died following immunization with i-antigen or live theronts.

In a separate trial, single i.p. injections of 10 μg of i-antigen mixed with either a CpG oligodeoxynucleotide (19-mer) adjuvant or Freunds complete adjuvant provided 33% and 40% protection, respectively. Control fish immunized with i-antigen given with a non-CpG oligonucleotide or BSA with a CpG oligodeoxynucleotide all died following challenge.

Serum and mucus antibody production in vaccinated fishes corresponded with protection. These results demonstrate the efficacy of purified i-antigen with adjuvant in eliciting protective immunity following vaccination.

Example 7

Figure 17:
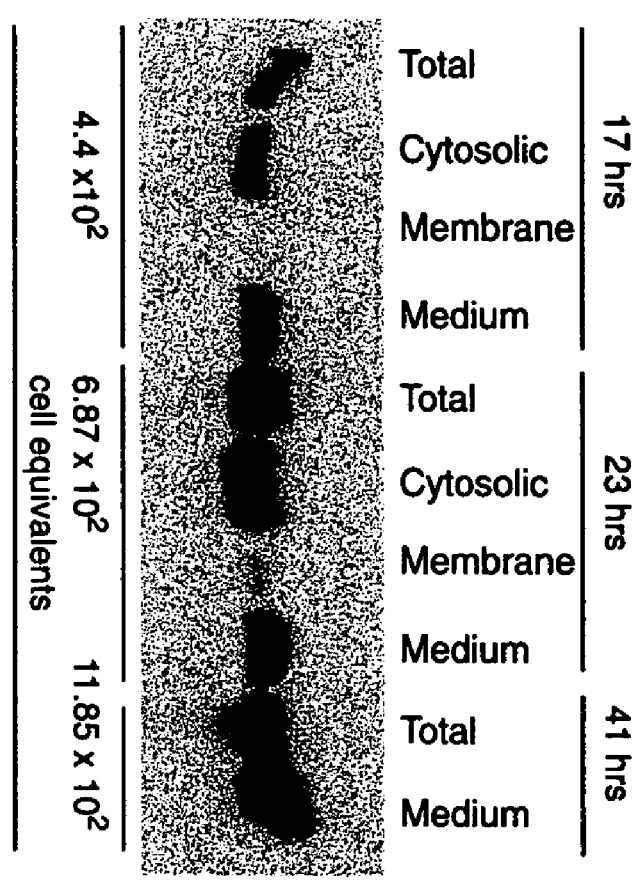

Immune Response of Channel Catfish to Vaccination with *I. multifiliis* (G5 Isolate) 55 kD I-antigen Plasmid Vaccine Truncated versions of the 55 kD i-antigen from *I. multifiliis* (G5 isolate) containing N-terminal and C-terminal deletions (Example 5), along with the full-length sequence, were cloned into the eucaryotic expression vector pcDNA3.1 for use fish vaccine trials. Although we have not yet determined how the respective gene products localize in cultured fish cells, an equivalent C-terminal deletion in the gene for the 48 kD i-antigen from serotype A resulted in secretion of the corresponding protein following transformation of *T. thermophila* (Example 9, FIG. 17).

Groups of 10 fish were vaccinated by intramuscular injection with either 10, 1 or 0.1 μg of plasmid DNA (pcDNA3.1) containing either the full-length, N-terminal or C-terminal deletion of the synthetic 55 kDa i-antigen gene. A positive control group vaccinated with the purified antigen in Freund's complete adjuvant (see Example 6), and a negative control group injected with the pcDNA3.1 containing the lacZ gene were included in the study. Sera were withdrawn from fish at two week intervals beginning 14 days after injection and antibody levels were determined by Western blotting and ELISA.

Figure 18:
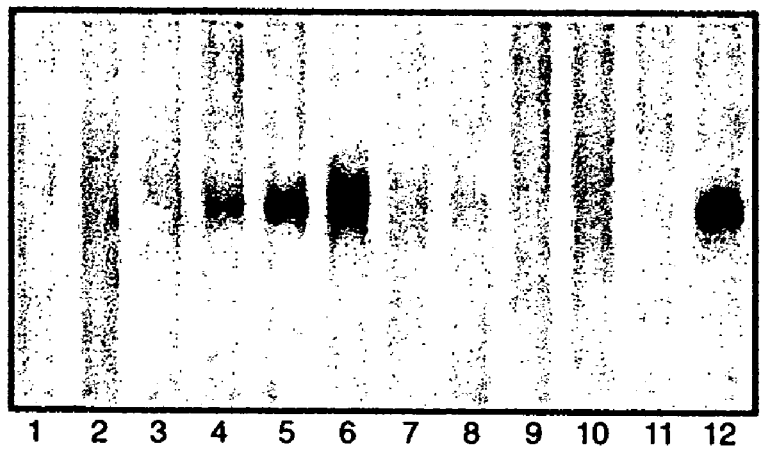

SDS-PAGE was carried out under both reducing and non-reducing conditions, and Western blots were probed with pooled antisera from the different groups of fish. The 55 kD i-antigen from parasite isolate G5 was affinity purified and fractionated by SDS-PAGE under non-reducing conditions (50 ng/lane). Protein was then transferred to PVDF membrane and reacted sequentially with pooled sera from fish vaccinated with pcDNA3.1 DNA vaccine constructs followed by a monoclonal antibody conjugate (alkaline phosphatase) against the heavy chain of channel catfish Ig. The Western blot is shown in FIG. 18. Lanes were probed with sera from fish immunized as follows: Lanes 1–3, 10, 1, and 0.1 μg full length gene construct, respectively; lanes, 4–6: 10, 1, and 0.1 μg C-terminal deletion construct, respectively; lanes 7–9: 10, 1, and 0.1 μg N-terminal deletion construct, respectively; lane 10, 10 μg LacZ construct (negative control); lane 11, naive fish serum; lane 12, fish vaccinated with 20 μg affinity purified 55 kDa i-antigen (positive control). Sera from fish vaccinated with constructs harboring the C-terminal deletion (lanes 4–6) reacted positively with the 55 kD protein run under non-reducing conditions, as did sera from fish injected with the purified antigen itself (lane 12). In contrast, only weak signals were seen in equivalent blots of protein separated under reducing conditions, the one exception being with sera from fish injected with 10 μg of the full-length construct. These results suggest that antibodies against the product of the C-terminal deletion (and against the i-antigen itself) are directed primarily towards conformational epitopes, while those against the full-length protein are directed towards linear epitopes. Of further interest was the fact that the antibody response to the vector encoded antigens decreased over time and was not detectable by ELISA 6 weeks after vaccination.

The animals were challenged with lethal numbers of parasites (15,000 theronts per fish) 9 weeks after immunization. The percent survival in all groups injected with the i-antigen constructs was higher than that in the negative control (LacZ). Still, not all fish died in the LacZ control group, and because the number of fish injected was small, the relative differences between groups were statistically significant in only one case (Table 1). This experiment did not include a group of fish injected with PBS alone.

TABLE 1

| Immunogen | LacZ | F10 | F1 | F0.1 | C10 | C1 | C0.1 | N10 | N1 | N0.1 | GSiAg |
|---|---|---|---|---|---|---|---|---|---|---|---|
| No- of fish challenged | 9 | 9 | 10 | 10 | 9 | 10 | 10 | 9 | 10 | 10 | 10 |
| No. of fish survived | 4 | 8 | 8 | 9 | 6 | 7 | 8 | 7 | 10 | 8 | 10 |
| Survival % | 44.4 | 88.9 | 80 | 90 | 66.7 | 70 | 80 | 77.8 | 100 | 80 | 100 |
| RSP | N.A. | 50 | 44.5 | 50.1 | 33.4 | 57.7 | 44.5 | 42.9 | 55.6 | 44.5 | 55.6 |
| *MDD ± SD | 14.0 ± 4.5 | 17.0 | 14.5 ± 13A | 16.0 ± 1.5 | 20.3 ± 5.5 | 12.3 ± 57 | 21.0 ± 6.4 | 10.5 | | 21.0 ± 7.1 | |

*Mean days to death +/− Standard Deviation: no significant difference between groups by One Way Anova,
**A significant difference in percent survival was seen between the negative control group (LacZ) and the test groups NI and G5 i-Ag (P < 0.5).

Groups of fish were injected with 10, 1 or 0.1 μg pcDNA3.1 DNA containing the sequence for either the full-length 55 kD i-antigen (F10, F1, F0.1), the C-terminal deletion (C10, C11, C0.1), or the N-terminal deletion (N10, N1, N0.1). Two additional groups of fish were injected with plasmid DNA containing a LacZ insert (LacZ), and 20 μg the affinity purified 55 kD protein (i-Ag). Fish were challenged 9 weeks after vaccination with 15,000 theronts per fish.

Because animals were exposed to what should have been a lethal challenge, the fact that some fish survived in the group injected with the lacZ constructs might be interesting in light of recent evidence that methylated CpG motifs in bacterial DNA can stimulate both cytokine production and B-cell proliferation, and in some cases, can protect animals non-specifically against microbial pathogens.

Example 8

Construction of a Multivalent *I. multifiliis* Vaccine

A multivalent vaccine vector is constructed based on the i-antigens of *I. multifiliis* serotype A or serotype D. The gene for the 48 kD i-antigen of serotype A has been isolated and the parasite itself is currently available for vaccine trials. If the 48 kD i-antigen is used, a synthetic copy of the gene equivalent to the one made for the 55 kD antigen (Example 5) is constructed. The construction is straightforward and involves the design and synthesis of overlapping oligonucleotides (~100 bp each) that span the coding region of the gene. The oligonucleotides are mixed at equimolar concentrations in a single reaction and allowed to assemble into the full-length sequence using a thermostable DNA polymerase (High Fidelity Expand enzyme, Roche). A fraction of the assembled product is then used as a template for amplification of the gene in a standard PCR reaction using flanking primers to drive the reaction. The resulting full-length product is gel-purified, cloned into pcDNA3.1 and sequenced. Errors in the sequence are corrected by in vitro mutagenesis according to the method of Deng et al. (*Anal. Biochem.* 200:81 88 (1992)) and the final version is tested as a DNA vaccine. A combined vaccine containing plasmid vectors for both the 48 and 55 kD i-antigens is also tested on fish challenged with serotype A and D.

Example 9

Immune Response of Channel Catfish to Live Vaccine: Transformed *Tetrahymena* Expressing Full-length or Truncated *I. multifiliis* (Serotype A) 48 kD I-antigen Protein and Heterologous Challenge with *I. multifiliis* (Serotype D)

The IAG48[G1] gene of *Ichthyophthirius multifiliis* G1 encodes the GPI anchored 48-kDa i-antigen. The extreme 3' region of the gene encodes a stretch of 14 mostly hydrophobic amino acids separated by a short spacer from three small amino acids (CAS). This sequence encodes the protein's GPI anchor addition site. *Tetrahymena thermophila* cells transformed with the entire IAG48[G1]gene produce an intact i-antigen anchored to the cells' surface. *Tetrahymena* cells transformed with a modified IAG48[G1]gene construct lacking the 3' sequence which includes the GPI addition site would be expected to produce a truncated protein lacking the GPI anchor.

*Tetrahymena* cells were transformed with either the gene encoding the full-length *Ichthyophthirius* G1 48-kDa i-antigen protein, or a truncated version of the gene that encodes the i-antigen protein lacking 19 amino acids at the carboxy terminus. Transformants encoding the intact or C-terminal truncated i-antigen were grown in standard *Tetrahymena* growth medium. Cell pellets and supernatant fluids were collected at the time points indicated. I-antigen was detected in cell cytosol, cell membrane or cell culture supernatants by Western blots using rabbit antisera against affinity purified *Ichthyophthirius* G5 i-antigen (see FIG. 17). It is clearly seen that the truncated protein is secreted into the culture medium.

Groups of channel catfish (6 fish per group) were immunized by bath exposure ($10^6$ or $10^5$ cells/fish) or intraperitoneal injection with *T. thermophila* transformants ($10^6$, $10^5$, or $10^4$ cells/fish) producing intact or truncated i-antigen. A third group of fish was immunized with membrane protein extracts (1 mg or 0.1 mg/fish) from *T. thermophila* producing the full length protein.

Immunization by bath exposure to *Tetrahymena* transformants. Two groups of fish (6 fish in each group) were immunized by bath exposure. The fish were exposed to either $10^6$ or $10^5$ cells/fish for a period of 24 hours. Two immunogens were used: 1) transformed *Tetrahymena* cells expressing the entire *Ichthyophthirius* G1 48-kDa protein, and 2) transformed cells secreting a truncated form of the i-antigen lacking the GPI anchor. Fish in the control group were exposed to *Tetrahymena* transformants expressing the neo 1 gene product. Fish were exposed twice at a 30 day interval and challenged 30–60 days after the last immunization with the G5 *Ichthyophthirius* isolate. There were no significant differences (z test) between test and control groups (see Table 2). Immunized fish were challenged with a heterologous strain (G5 isolate) of *Ichthyophthirius* expressing a different i-antigen than that produced by the recombinant *Tetrahymena* used for vaccination. It is expected that challenge with a strain of *Ichthyophthirius* producing an i-antigen homologous to the G1 48 i-antigen would show increased levels of protection.

TABLE 2

Vaccination by bath exposure

| Immunogen | Dose (cells/fish) | Number of fish challenged | Number of fish surviving | % survival | RSP[3] | MDD[4] ± SD[5] |
|---|---|---|---|---|---|---|
| Neo control | $10^6$ | 5 | 2 | 40 | N.A. | 17.0 ± 1.0 |
| TG1[1] | $10^5$ | 5 | 3 | 60 | 33.3 | 18.5 ± 2.1 |
| TG1 | $10^6$ | 6 | 3 | 50 | 25.0 | 13.3 ± 4.9 |
| sTG1[2] | $10^5$ | 6 | 3 | 50 | 25.0 | 21.0 ± 4.6 |
| sTG1 | $10^6$ | 6 | 4 | 66.7 | 40.0 | 17.0 ± 1.4 |

[1]*Tetrahymena* expressing intact membrane form of *Ichthyophthirius* G1 i-antigen.
[2]*Tetrahymena* secreting truncated form of G1 i-antigen.
[3]Relative Survival Percent = 1 − (number of dead fish in test group/number of dead fish in control group) × 100%
[4]Mean days to death
[5]Standard deviation Immunization by injection of *Tetrahymena* transformants. Fish in each group were injected intraperitoneally with $10^6$, $10^5$, or $10^4$ live transformed *Tetrahymena* cells/fish. The same immunogens and controls were tested as in the immersion vaccinations. Fish were injected two times at a 30 day interval, and challenged 21 days after the last immunization with G5 *Ichthyophthirius*. A greater degree of protection was elicited in immunized fish compared to controls (Table 3).

TABLE 3

Vaccination by injection

| Immunogen | Dose (cells/fish) | Number of fish challenged | Number of fish surviving | % survival | RSP[3] | MDD[4] ± SD[5] |
|---|---|---|---|---|---|---|
| Neo control | $10^5$ | 6 | 2 | 33.3 | N.A. | 15.3 ± 3.6 |
| TG1[1] | $10^6$ | 5 | 3 | 60 | 44.5 | 19.0 ± 2.8 |
| TG1 | $10^5$ | 5 | 4 | 80 | 58.4 | 15.0 ± 0.0 |
| TG1 | $10^4$ | 6 | 2 | 33.3 | 0 | 14.0 ± 1.4 |

TABLE 3-continued

Vaccination by injection

| Immu-nogen | Dose (cells/fish) | Number of fish challenged | Number of fish surviving | % sur-vival | RSP[3] | MDD[4] ± SD[5] |
|---|---|---|---|---|---|---|
| sTG1[2] | $10^6$ | 6 | 5 | 83.3 | 50.0 | 21.0 ± 4.6 |
| sTG1 | $10^5$ | 6 | 3 | 50.0 | 25.0 | 20.0 ± 5.7 |

[1]*Tetrahymena* expressing intact membrane form of *Ichthyophthirius* G1 i-antigen.
[2]*Tetrahymena* secreting truncated form of G1 i-antigen.
[3]Relative Survival Percent = 1 – (number of dead fish in test group/number of dead fish in control group) × 100%
[4]Mean days to death
[5]Standard deviation Serum antibody production. Fish serum antibody responses against recombinant G1 *Ichthyophthirius* i-antigen were determined by ELISA at 2, 4, and 6 weeks after immunization. Serum antibodies from immunized fish were detected with a sandwich ELISA technique that used wells coated with a cross-reactive rabbit antibody against *Ichthyophthirius* G5 i-antigen to capture recombinant G1 i-antigen produced in transformed *Tetrahymena*. Sera from test and control fish were added to wells and antibodies that bound to the captured i-antigen were detected using an alkaline phosphatase labeled mouse mAb against the immunoglobulin heavy chain of channel catfish. ELISA controls consisted of antibody-coated wells reacted with membrane protein from *Tetrahymena* cells transformed with the neo1 gene.

Figure 19A:
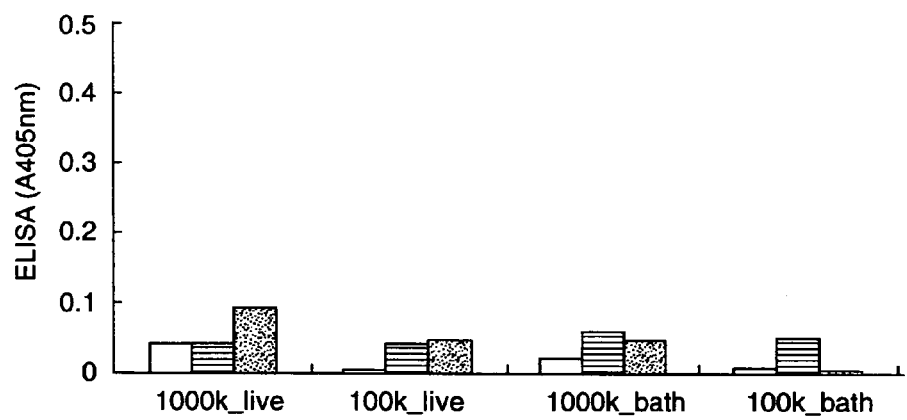
Figure 19B:
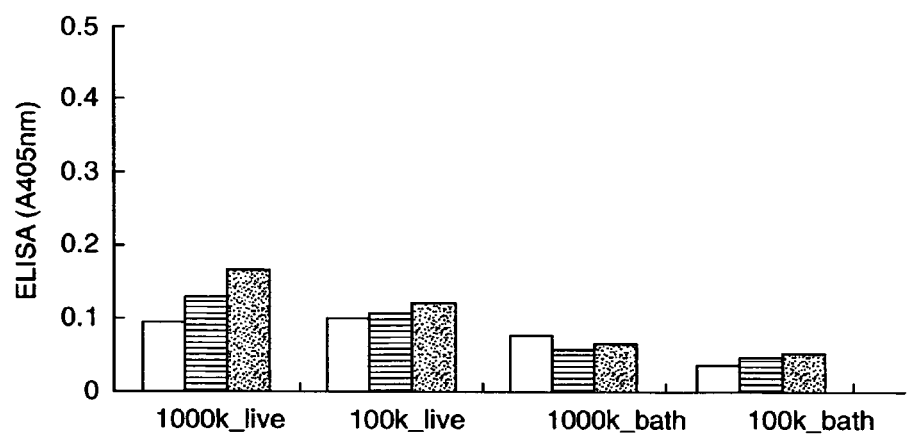

Fish injected with *Tetrahymena* membrane protein produced high levels of serum antibody against the recombinant i-antigen. The antibody response elicited by fish immunized with live cells was almost an order of magnitude lower. The antibody response of fish immunized by bath or i.p. injection with live cells secreting recombinant i-antigen was approximately two-fold greater than the antibody response of fish immunized with *Tetrahymena* producing the membrane-bound, intact i-antigen. In FIG. 19, the differences in antibody production between fish immunized with the (a) membrane associated or (b) secreted form of the i-antigen are shown. These results suggest that live cells secreting antigen are more efficatious in eliciting the production of serum antibodies. The mucosal antibody response was not determined in these experiments.

Example 10

Immune Response of Channel Catfish to Live Vaccine: Transformed *Tetrahymena* Expressing Full-length or Truncated *I. multifiliis* (Serotype A) 48 kD I-antigen Protein and Homologous Challenge with *I. multifiliis* (Serotype A)

*Tetrahymena* cells were transformed with either the entire *Ichthyophthirius* G1 48-kDa i-antigen protein, or a truncated gene sequence which encodes the i-antigen protein lacking 19 amino acids at the carboxy terminus as in Example 9.

Groups of channel catfish (70 fish per group) were vaccinated by intraperitoneal injection with $10^6$ *T. thermophila* transformants producing intact or truncated i-antigen. A third group of fish (control group) was vaccinated with *T. thermophila* transformants expressing neo. No adjuvant was used in any of the vaccinations. The fish were boosted 2 weeks following the initial injection and bled at 3 weeks following the initial injection. Sera from 3 fish per group were pooled.

Figure 20B:
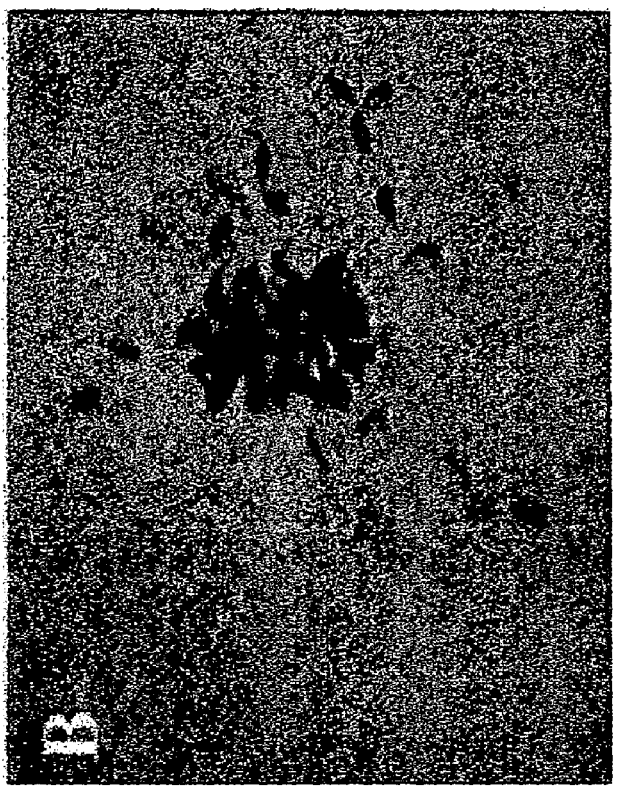
Figure 20A:
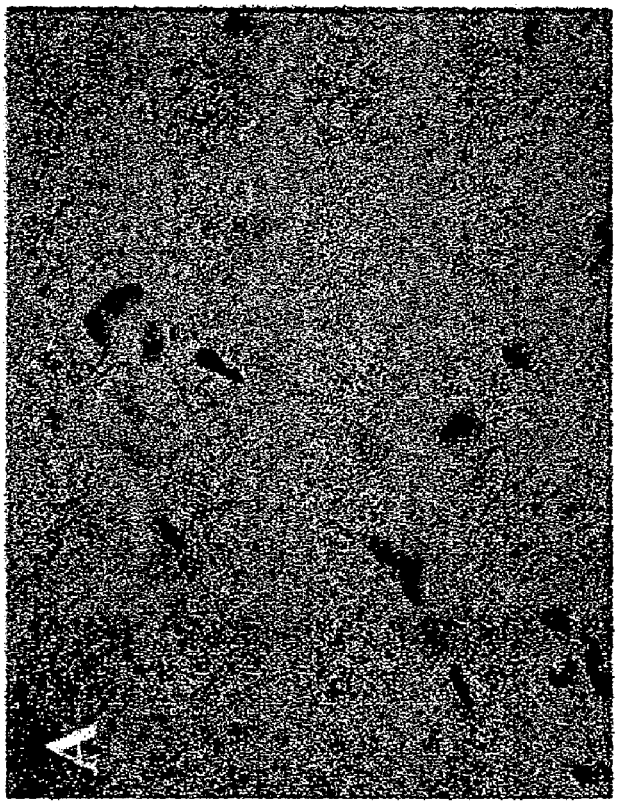

A 96 well ELISA plate was seeded with a homologous strain (i.e., serotype A) of *I. multifiliis* (strain NY1, a G1 isolate), 200 cells per well. Fish sera were serially diluted and added to the wells, and the effect on the motility of *I. multifiliis* was observed. Immobilization of *I. multifiliis* was immediately evident at serum dilutions of 1:20, and at higher concentrations the organisms exhibited clumping (FIG. 20). Sera from the control group did not cause any change in motility of *I. multifiliis*.

As another control, additional wells were seeded with a heterologous strain of *I. multifiliis* (a G5 isolate). The motility of these organisms was not affected by sera from any of the groups of vaccinated fish, confirming that the immobilization epitopes on *I. multifiliis* i-antigens are highly specific.

For comparison, two other groups of fish were vaccinated with purified subunit proteins produced from recombinant *Tetrahymena* (either the full-length 48 kD i-antigen protein or the C-terminal truncated version). The subunit proteins were adjuvanted with Freund's Complete Adjuvant. In a plate assay similar to the one described above using the homologous strain of *I. multifiliis*, some immobilization was observed but not to the degree caused by the "live vaccine." This observation lends support to the expectation that the "live vaccine" will prove to be more efficacious than the analogous protein subunit vaccine.

Example 11

Degenerate Primers for Amplification of I-antigen Genes from Other Serotypes

Forward and reverse primers for amplifying i-antigen gene sequences from different parasite isolates were designed based on regions of homology discovered between the 48 kDa (G1 strain) and 55 kDa i-antigens (G5 strain) of *I. multifiliis*. Forward primer P2 was successfully used to amplify sequences from a variety of different parasite isolates in combination with the reverse primers P3, P4 and P5. Primer sequences are as follows: P2: CCGAATTCTCTGG(C/T)ACTGCACTTGATGATGGAG (SEQ ID NO:45), which is 2-fold degenerate and corresponds to all or part of the amino acid sequence GTALDDGV (SEQ ID NO:46); it contains an EcoR I restriction site for cloning purposes; P3: GTGGATCCAGTACATGTTACA(A/G)TACCTGC (SEQ ID NO:47), which is 2-fold degenerate and corresponds to all or part of the amino acid sequence AGTDTCT (SEQ ID NO:48); it contains a BamH I restriction site for cloning purposes; P4: GTGGATCC(A/G)CCAGAAGT-TAATTTTTTA(T/G)TAC (SEQ ID NO:49), which is 4-fold degenerate and corresponds to all or part of the amino acid sequence CTKKLTSGA (SEQ ID NO:50); it contains a BamH I site; and P5: GTGGATCCAAGGAAAT(C/T)GATAAAAA(T/A)TTAGCG (SEQ ID NO:51), which is 4-fold degenerate and corresponds to all or part of amino acid sequence FAKFLSISL (SEQ ID NO:52); it contains a BamH I restriction site. PCR amplification of i-antigen gene sequences was carried out under standard conditions (30 cycles at 94° C. for 1 minute, 52° C. for 1 minute, 72° C. for 1 minute).

Figure 21:
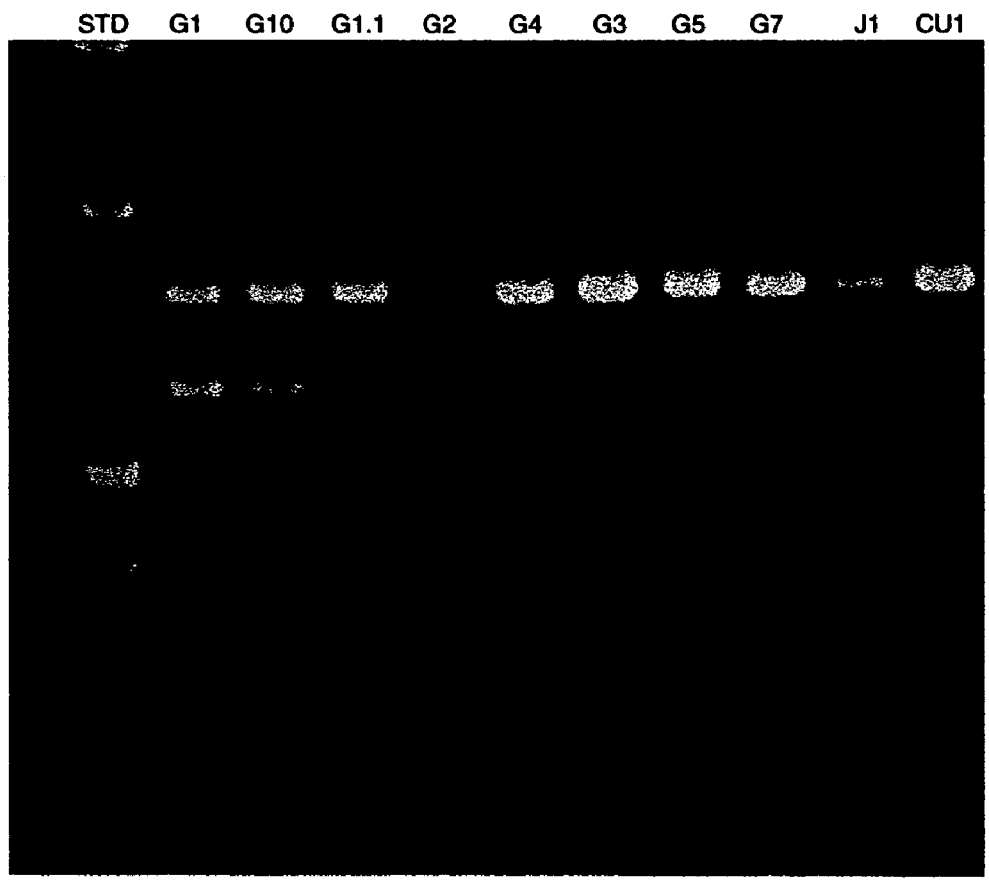

FIG. 21 shows PCR amplification of genomic DNA from several serotypic variants using the P2/P4 primer pair. Amplification products were run on 1.5% agarose gel and stained with ethidium bromide. Multiple bands seen in some of the lanes may be due to amplification from more than a single i-antigen gene (serotype A, for example, has two i-antigen genes) or to mispriming from closely related sequences within tandem repeats of the same gene. The major band in the lane containing G5 isolate DNA is precisely the expected size (~800 bp) based on the sequence of the 55 kD i-antigen gene. Among the ten isolates represented in FIG. 21, two belong to serotype A (G1 and G10) and four to serotype D (G3, US, G7, and JI). Isolates G1.1, G2 and 04 correspond to serotypes B, C and E, respectively (the CUI isolate has not yet been typed).

Example 12

Construction of an I-antigen/C3d DNA Vaccine

Several distinct genes for the third component of trout complement have been identified. Although unique from one another, they share the same coding region for C3d (J. Sunyer et al., *Proc. Natl. Acad. Sci USA* 93, 8546 8551, (1996)). Preparation of the hybrid i-antigen/C3d construct is carried out as follows. Three separate PCR reactions are performed to synthesize the basic elements of the construct. The first reaction involves amplification of the 55 kDa i-antigen gene using a forward primer that encodes restriction endonuclease cloning sites and replaces the existing N-terminal signal peptide of the i-antigen with the signal peptide of trout Ig. The reverse primer in this case contains restriction sites as well, and omits the coding sequence for the last 15 amino acids at the C-terminus of the protein (ordinarily, the C-terminus acts as a GPI-anchor addition site). The second PCR reaction involves synthesis of the C3d fragment containing appropriate restriction sites at its ends. The forward primer in this case mutates the first cysteine in the C3d fragment to a serine (thereby assuring correct disulfide bridging between cysteine residues within C3d. The final PCR reaction involves synthesis of a second C3d fragment containing a short linker sequence (G5[G$_4$S]$_2$) (SEQ ID NO:101) at its C-terminus along with appropriate restriction sites that allow cloning between the i-antigen sequence and the first C3d PCR product. The template for synthesis of the C3d fragments is trout genomic DNA. The entire construct is assembled by first cloning the PCR product for the i-antigen gene into pcDNA3.1. The C3d products are inserted at the 3' end of the i-antigen gene using restriction sites built into the fragments. Following transformation of bacteria with the resulting construct, the vector is directly sequenced to determine the number of C3d fragments in the hybrid, as well as the accuracy of the overall sequence. The same basic strategy is employed in the construction of a HEL (hen egg-white lysozyme)/C3d hybrid control vaccine. The rationale for including the model antigen (HEL) in these studies relates to the uncertainty associated with correct folding of the i-antigen/C 3d hybrid (and consequently the likelihood that it will induce the expected result). After correcting nucleotide sequence errors, groups of fish (in this case 20–50 g rainbow trout) are injected with varying amounts of either the i-antigen or HEL hybrid constructs and the antibody response is determined in plate ELISAs (as described in other Examples) using secondary antibody conjugates against trout Ig. Trout immunized with the i-antigen/C3d hybrid vaccine are also challenged with parasites of the G5 isolate to determine levels of protection.

Example 13

Oral Delivery of a DNA Vaccine

Oral delivery represents an extremely attractive alternative for administration of DNA vaccines, particularly in aquaculture species. Based on recent experiments in mice (D. Jones et al., *Dev. Biol. Stand.* 92:149 155 (1998); K. Roy et al., *Nature Med.* 5:387–391-(1999)) it may now be possible to administer genetic vaccines orally using biodegradable polymers. Fish are expected to be capable of developing cutaneous mucosal antibody responses against *Ichthyophthirius* following oral vaccination with vector-encoded antigens.

Juvenile channel catfish are vaccinated orally using i-antigen based DNA vaccines complexed with chitosan. Encapsulation is performed substantially in accordance with the method of K. Leong et al., (*J. Controlled Release* 53:183 193, (1998)). Briefly, chitosan (MW 390,000) is dissolved at a concentration of 0.02% in 25 mM sodium acetate, pH 5–7. After prewarming to 55° C., 100 µl aliquots are added to an equivalent volume of vector DNA (1 µg/ml) in sodium sulfate buffer at 55° C., and the mixture is vortexed rapidly for 20 seconds. Nanoparticles formed by complex coacervation are examined by scanning electron microscopy and the resulting preparations stored at room temperature. Preparations are combined with fish food and animals are fed the equivalent of 10–100 µg plasmid. DNA. Antigen-specific antibody responses are determined in cutaneous mucus and serum by ELISA, and positive fish are challenged with live theronts.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. An isolated nucleic acid molecule comprising a polynucleotide fragment having a nucleotide sequence that encodes a polypeptide comprising amino acids 21–452 of SEQ ID NO:7, wherein the polypeptide is capable of generating an immune response in fish against *Ichthyophthirius multifiliis*.

2. An isolated nucleic acid molecule comprising a polynucleotide fragment having a nucleotide sequence that encodes a polypeptide comprising an N-terminus encoded by SEQ ID NO:19 or a C-terminus encoded by SEQ ID NO:20, or both.

3. An isolated nucleic acid molecule comprising a polynucleotide fragment having a nucleic acid sequence that encodes SEQ ID NO:7.

4. The nucleic acid molecule of claim 3 comprising at least one nucleotide sequence selected from the group consisting of SEQ ID NO:3, SEQ ID NO:5, SEQ ID NO:44 and SEQ ID NO:102.

5. The nucleic acid molecule of any of claims 1–3 or 4 that is a vector capable of expressing the polypeptide encoded by the nucleic acid sequence in a *Tetrahymena* host cell.

6. An isolated nucleic acid molecule comprising at least 50 nucleotides that hybridizes with any of the nucleic acid molecules of claims 1–3 or 4 under conditions exemplified by about 150 mM NaCl, 15 mM trisodium citrate, and pH 7.6 at 55° C., wherein the nucleic acid molecule encodes a polypeptide which is capable of generating an immune response in fish against *Ichthylphthirius multifilis*.

7. An isolated nucleic acid molecule comprising a polynucleotide fragment comprising at least 50 nucleotides that hybridizes to the complement of SEQ ID NO:3, SEQ ID NO:5, SEQ ID NO:44, SEQ ID NO:19, SEQ ID NO:20 or SEQ ID NO:102 under conditions comprising about 150 mM NaCl, 15 mM trisodium citrate, and pH 7.6 at 55° C., wherein the nucleic acid molecule encodes a polypeptide which is capable of generating an immune response in fish against *Ichthylphthirius multifilis*.

8. A composition for inducing an immune response in a fish, said composition comprising at least one nucleic acid molecule of any of claims 1–5, 6, 7 or 4.

9. The composition of claim 8 wherein administration of the composition to fish prevents or controls *I. multifiliis* infection.

10. The composition of claim 8 wherein the polypeptide encoded by the nucleotide sequence is linked at its carboxy-terminus to a plurality of molecules of the C3d component of complement.

11. The composition of claim 8 formulated for oral administration.

12. The composition of claim 11 wherein the nucleic acid molecule is encapsulated in a biodegradable polymer.

13. A Tetrahymena host cell transformed with the nucleic acid molecule of claim 5.

14. Transformed *Tetrahymena* comprising the nucleic acid molecule of any of claims 1–5, 6, 7 or 4.

15. An isolated nucleic acid molecule which is complementary to any of the nucleic acid molecules of claims 1–3 or 4.

* * * * *